US00RE48622E

(19) United States
(12) Reissued Patent
Ford et al.

(10) Patent Number: US RE48,622 E
(45) Date of Reissued Patent: Jul. 6, 2021

(54) THERAPEUTICALLY ACTIVE PYRAZOLO-PYRIMIDINE DERIVATIVES

(71) Applicants: UCB Biopharma SPRL, Brussels (BE); KATHOLIEKE UNIVERSITEIT LEUVEN, K.U.Leuven R&D, Leuven (BE)

(72) Inventors: Daniel James Ford, Slough (GB); Richard Jeremy Franklin, Slough (GB); Anant Ramrao Ghawalkar, Hyderabad (IN); Helen Tracey Horsley, Slough (GB); Qiuya Huang, Leuven (BE); James Thomas Reuberson, Slough (GB); Bart Vanderhoydonck, Diest (BE)

(73) Assignees: UCB Biopharma SRL, Brussels (BE); Katholieke Universiteit Leuven, K.U. Leuven R&D, Leuven (BE)

(21) Appl. No.: 16/517,969

(22) Filed: Jul. 22, 2019

Related U.S. Patent Documents

Reissue of:
(64) Patent No.: 9,714,248
Issued: Jul. 25, 2017
Appl. No.: 14/650,771
Filed: Jun. 9, 2015

(30) Foreign Application Priority Data

Dec. 20, 2012 (GB) ..... 1223021
Feb. 4, 2013 (GB) ..... 1301935

(51) Int. Cl.
*C07D 487/04* (2006.01)
*A61K 31/519* (2006.01)
*C07D 471/04* (2006.01)

(52) U.S. Cl.
CPC ..... *C07D 487/04* (2013.01); *A61K 31/519* (2013.01); *C07D 471/04* (2013.01)

(58) Field of Classification Search
CPC .. C07D 487/04; C07D 471/04; A61K 31/519; A61P 43/00; A61P 37/06; A61P 37/02; A61P 35/00; A61P 33/06; A61P 31/12; A61P 29/00
See application file for complete search history.

(56) References Cited

U.S. PATENT DOCUMENTS

| | | | | |
|---|---|---|---|---|
| 6,423,716 | B1 | 7/2002 | Matsuno et al. | |
| 8,076,338 | B2 * | 12/2011 | Anand | A61P 9/10 514/252.02 |
| 2004/0204400 | A1 | 10/2004 | Chern et al. | |
| 2005/0054651 | A1 | 3/2005 | Natarajan et al. | |

FOREIGN PATENT DOCUMENTS

| | | | | |
|---|---|---|---|---|
| DE | 1110649 | * | 11/1958 | |
| DE | 11 10 649 | B | 7/1961 | |
| EP | 1 772 454 | A1 | 4/2007 | |
| WO | 2005/117909 | A2 | 12/2005 | |
| WO | WO2005117909 | * | 12/2005 | A61K 31/7176 |
| WO | WO-2005117909 | A2 * | 12/2005 | A61P 19/02 |
| WO | 2006/071819 | A1 | 7/2006 | |
| WO | WO-2006071819 | A1 * | 7/2006 | A61P 27/02 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Trilleras et al., "Anhydrous versus hydrated N4-substituted 1H-pyrazolo[3,4-d]pyrimidine-4,6-diamines: hydrogen bonding in two and three dimensions", Acta Crystallographica Section B Structural Science, 2008, 64(5), 610-622.
Quintela et al., "6-Dimethylamino 1H-Pyrazolo[3,4-d]pyrimidine Derivatives as New Inhibitors of Inflammatory Mediators in Intact Cells", Bioorganic & Medicinal Chemistry, 2003, vol. 11, 863-868.
Quintela et al., "Pyrazolopyrimidines: synthesis, effect on histamine release from rat peritoneal mast cells and cytotoxic activity", European Journal of Medicinal Chemistry, 2001, 36(4), 321-332.
Quintela et al., "Pyridopyrimidines, pyrazolopyrimidines, pyridothienopyrimidines and pyridothienotriazines. Synthesis and biological activity", Trends in Heterocyclic Chemistry, 2005, vol. 10, 97-114.

* cited by examiner

*Primary Examiner* — Jerry D Johnson
(74) *Attorney, Agent, or Firm* — McDonnell Boehnen Hulbert & Berghoff LLP

(57) ABSTRACT

A series of pyrazolo[3,4-d]pyrimidine derivatives that are substituted at the 4-position by a diaza monocyclic, bridged bicyclic or spirocyclic moiety, are beneficial in the treatment and/or prevention of various human ailments, including inflammatory, autoimmune and oncological disorders; viral diseases and malaria; and organ and cell transplant rejection.

12 Claims, No Drawings

THERAPEUTICALLY ACTIVE PYRAZOLO-PYRIMIDINE DERIVATIVES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a US national phase of International Application No. PCT/EP2013/077846 filed on Dec. 20, 2013, which claims priority to Great Britain Patent Application No. 1223021.5 filed on Dec. 20, 2012 and Great Britain Patent Application No. 1301935.1 filed on Feb. 4, 2013.

The present invention relates to a class of fused pyrimidine derivatives, and to their use in therapy. More particularly, the present invention provides pyrazolo[3,4-d]-pyrimidine derivatives that are substituted at the 4-position by a diaza monocyclic, bridged bicyclic or spirocyclic moiety. These compounds are selective inhibitors of phosphatidylinositol-4-kinase IIIβ (PI4KIIIβ) activity, and are accordingly of benefit as pharmaceutical agents, especially in the treatment of adverse inflammatory, autoimmune and oncological disorders, in the treatment of viral diseases and malaria, and in the management of organ and cell transplant rejection.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/034738 discloses that inhibitors of PI4KIIIβ activity are useful as medicaments for the treatment of autoimmune and inflammatory disorders, and organ and cell transplant rejection.

WO 2010/103130 describes a family of oxazolo[5,4-d] pyrimidine, thiazolo[5,4-d]-pyrimidine, thieno[2,3-d]pyrimidine and purine derivatives that are active in a range of assays, including the Mixed Lymphocyte Reaction (MLR) test, and are stated to be effective for the treatment of immune and auto-immune disorders, and organ and cell transplant rejection. WO 2011/147753 discloses the same family of compounds as having significant antiviral activity. Furthermore, WO 2012/035423 discloses the same family of compounds as having significant anticancer activity.

Copending international patent applications PCT/GB2012/051992 (published on 21 Feb. 2013 as WO 2013/024291), PCT/EP2012/072130 (published on 16 May 2013 as WO 2013/068458) and PCT/EP2013/070600 (claiming priority from UK patent application 1217704.4) describe various series of fused pyrimidine derivatives that are stated to be of benefit as pharmaceutical agents, especially in the treatment of adverse inflammatory, autoimmune and oncological disorders, in the treatment of viral diseases, and in the management of organ and cell transplant rejection.

Inhibitors of PI4KIIIβ have been identified as molecules with an ideal activity profile for the prevention, treatment and elimination of malaria (cf. C. W. McNamara et al., Nature, 2013, 504, 248-253).

WO 99/51582 describes a class of nitrogen-containing heterocyclic compounds that are stated to have an activity of inhibiting phosphorylation of a platelet-derived growth factor (PDGF) receptor.

None of the prior art available to date, however, discloses or suggests the precise structural class of pyrazolo[3,4-d] pyrimidine derivatives as provided by the present invention as having activity as PI4KIIIβ inhibitors.

The compounds of the present invention are potent and selective inhibitors of PI4KIIIβ activity, inhibiting the kinase affinity of human PI4KIIIβ ($IC_{50}$) at concentrations of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for human PI4KIIIβ relative to other human kinases.

Certain compounds in accordance with the present invention are active as inhibitors when subjected to the Mixed Lymphocyte Reaction (MLR) test. The MLR test is predictive of immunosuppression or immunomodulation. Thus, when subjected to the MLR test, certain compounds of the present invention display an $IC_{50}$ value of 10 μM or less, generally of 5 μM or less, usually of 2 μM or less, typically of 1 μM or less, suitably of 500 nM or less, ideally of 100 nM or less, and preferably of 20 nM or less (again, the skilled person will appreciate that a lower $IC_{50}$ figure denotes a more active compound).

The compounds of the invention possess notable advantages in terms of their high potency, demonstrable efficacy at lower doses, and valuable pharmacokinetic and pharmacodynamic properties (including clearance and bioavailability).

The present invention provides a compound of formula (I) or an N-oxide thereof, or a pharmaceutically acceptable salt or solvate thereof:

(I)

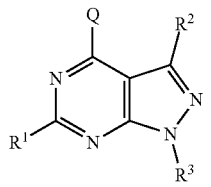

wherein

Q represents a group of formula (Qa), (Qb), (Qc), (Qd) or (Qe):

(Qa)

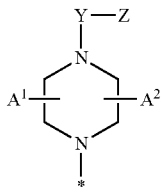

(Qb)

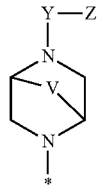

-continued (Qc)

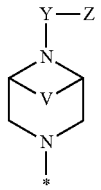

(Qd)

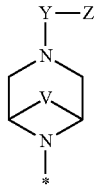

(Qe)

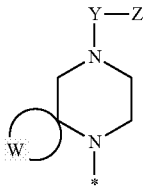

in which the asterisk (*) represents the point of attachment to the remainder of the molecule;

V represents —$CH_2$—, —$C(CH_3)_2$—, —$CH_2CH_2$—, —$CH_2CH_2CH_2$—, —$CH_2OCH_2$—, —$CH_2SCH_2$—, —$CH_2S(O)CH_2$—, —$CH_2S(O)_2CH_2$— or —$CH_2N(R^4)CH_2$—;

W represents the residue of a $C_{3-7}$cycloalkyl or $C_{3-7}$ heterocycloalkyl group;

Y represents a covalent bond, or a linker group selected from —C(O)—, —S(O)—, —$S(O)_2$—, —C(O)O—, —C(O)N($R^4$)—, —C(O)C(O)— and —$S(O)_2N(R^4)$—, or a linker group of formula (Ya):

(Ya)

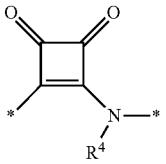

in which the asterisk (*) represents the point of attachment to the remainder of the molecule;

Z represents hydrogen; or Z represents $C_{1-6}$ alkyl, $C_{2-6}$ alkenyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents;

$A^1$ represents hydrogen, cyano or trifluoromethyl; or $A^1$ represents $C_{1-6}$ alkyl, optionally substituted by one or more substituents independently selected from fluoro, —$OR^a$, trifluoromethoxy, —$NR^bR^c$, —$CO_2R^d$ and —$CONR^bR^c$; or $A^1$ represents $C_{3-7}$ cycloalkyl;

$A^2$ represents hydrogen or $C_{1-6}$ alkyl;

$R^1$ and $R^2$ independently represent hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$N(SO_2R^e)_2$, —$NHSO_2NR^bR^c$, —$COR^d$, —$CO_2R^d$, —$CONR^bR^c$, —$CON(OR^a)R^b$ or —$SO_2NR^bR^c$; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, heteroaryl or heteroaryl($C_{1-6}$)alkyl, any of which groups may be optionally substituted by one or more substituents;

$R^3$ represents hydrogen; or $R^3$ represents $C_{1-6}$ alkyl, optionally substituted by one or more halogen atoms;

$R^4$ represents hydrogen; or $R^4$ represents $C_{1-6}$ alkyl, optionally substituted by one or more substituents independently selected from —$OR^a$ and —$NR^bR^c$;

$R^a$ represents hydrogen; or $R^a$ represents $C_{1-6}$ alkyl, aryl, aryl($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl ($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

$R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl, pentyl and hexyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable $C_{2-6}$ alkenyl groups include vinyl, allyl and prop-1-en-2-yl.

Suitable $C_{3-7}$ cycloalkyl groups, which may comprise benzo-fused analogues thereof, include cyclopropyl, cyclobutyl, cyclopentyl, indanyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include oxetanyl, azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Examples of suitable heterocycloalkenyl groups include oxazolinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, imidazo[2,1-b]thiazolyl, benzimidazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, benzothiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups. Additional examples include pyrazolo[4,3-c]pyridinyl and benzisoxazolyl.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C{=}O$)⇆enol ($CH{=}CHOH$) tautomers or amide ($NHC{=}O$)⇆hydroxyimine ($N{=}COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^{1}H$, $^{2}H$ (deuterium) or $^{3}H$ (tritium) atom, preferably $^{1}H$. Similarly, by way of example, each individual carbon atom present in formula (I), or in the formulae depicted hereinafter, may be present as a $^{12}C$, $^{13}C$ or $^{14}C$ atom, preferably $^{12}C$.

In a particular embodiment, Q represents a group of formula (Qa) as defined above. In a second embodiment, Q represents a group of formula (Qb) as defined above. In a third embodiment, Q represents a group of formula (Qc) as defined above. In a fourth embodiment, Q represents a group of formula (Qd) as defined above. In a fifth embodiment, Q represents a group of formula (Qe) as defined above.

Where Q represents a group of formula (Qa) as defined above, this may be a group of formula (Qa-1), (Qa-2), (Qa-3), (Qa-4), (Qa-5) or (Qa-6):

(Qa-1)

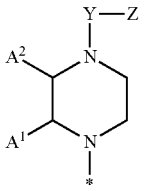

(Qa-2)

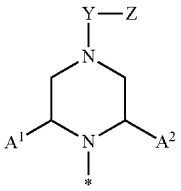

(Qa-3)

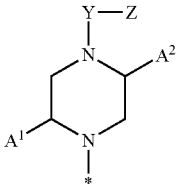

(Qa-4)

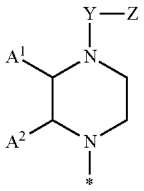

(Qa-5)

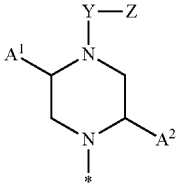

-continued (Qa-6)

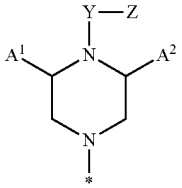

in which the asterisk (*) represents the point of attachment to the remainder of the molecule; and Y, Z, $A^1$ and $A^2$ are as defined above.

In a first embodiment, Q represents a group of formula (Qa-1) as defined above.

In a second embodiment, Q represents a group of formula (Qa-2) as defined above.

In a third embodiment, Q represents a group of formula (Qa-3) as defined above.

In a fourth embodiment, Q represents a group of formula (Qa-4) as defined above.

In a fifth embodiment, Q represents a group of formula (Qa-5) as defined above.

In a sixth embodiment, Q represents a group of formula (Qa-6) as defined above.

Generally, V represents —$CH_2$—, —$C(CH_3)_2$—, —$CH_2CH_2$— or —$CH_2CH_2CH_2$—.

In one embodiment, V represents —$CH_2$— or —$C(CH_3)_2$—. In a first aspect of that embodiment, V represents —$CH_2$—. In a second aspect of that embodiment, V represents —$C(CH_3)_2$—. Where Q represents a group of formula (Qb) and V represents —$CH_2$— or —$C(CH_3)_2$—, the bicyclic moiety containing the integer V is a 2,5-diazabicyclo[2.2.1]-heptane ring system. Where Q represents a group of formula (Qc) or (Qd) and V represents —$CH_2$— or —$C(CH_3)_2$—, the bicyclic moiety containing the integer V is a 3,6-diazabicyclo[3.1.1]heptane ring system.

In another embodiment, V represents —$CH_2CH_2$—. Where Q represents a group of formula (Qb) and V represents —$CH_2CH_2$—, the bicyclic moiety containing the integer V is a 2,5-diazabicyclo[2.2.2]octane ring system. Where Q represents a group of formula (Qc) or (Qd) and V represents —$CH_2CH_2$—, the bicyclic moiety containing the integer V is a 3,8-diazabicyclo[3.2.1]octane ring system.

In a further embodiment, V represents —$CH_2CH_2CH_2$—. Where Q represents a group of formula (Qb) and V represents —$CH_2CH_2CH_2$—, the bicyclic moiety containing the integer V is a 6,8-diazabicyclo[3.2.2]nonane ring system. Where Q represents a group of formula (Qc) or (Qd) and V represents —$CH_2CH_2CH_2$—, the bicyclic moiety containing the integer V is a 7,9-diazabicyclo[3.3.1]nonane ring system.

In further embodiments, V may represent: (i) —$CH_2OCH_2$—; (ii) —$CH_2SCH_2$—; (iii) —$CH_2S(O)CH_2$—; (iv) —$CH_2S(O)_2CH_2$—; or (v) —$CH_2N(R^4)CH_2$—.

Where Q represents a group of formula (Qe), the cyclic group of which W is the residue is spiro-fused to the adjacent six-membered ring containing two nitrogen atoms.

Generally, W represents the residue of a $C_{3-7}$ cycloalkyl group.

Where W represents the residue of a $C_{3-7}$ cycloalkyl group, the cyclic group of which W is the residue is selected from cyclopropyl, cyclobutyl, cyclopentyl, cyclohexyl and cycloheptyl. Suitably, the cyclic group of which W is the residue is a $C_{4-6}$ cycloalkyl group. In a particular embodiment, the cyclic group of which W is the residue is cyclobutyl.

Where W represents the residue of a $C_{3-7}$ heterocycloalkyl group, the cyclic group of which W is the residue suitably comprises at least one heteroatom selected from oxygen, sulphur and nitrogen. Suitably, the cyclic group of which W is the residue is a $C_{4-6}$ heterocycloalkyl group. Particular examples of the cyclic group of which W is the residue include oxetanyl, azetidinyl, tetrahydrofuranyl and pyrrolidinyl.

Generally, Y represents a covalent bond, or a linker group selected from —C(O)—, —S(O)—, —$S(O)_2$—, —C(O)O—, —C(O)N($R^4$)— and —$S(O)_2N(R^4)$—, or a linker group of formula (Ya) as defined above.

Typically, Y represents a covalent bond, or a linker group selected from —C(O)—, —C(O)O— and —C(O)N($R^4$)—, or a linker group of formula (Ya) as defined above.

Suitably, Y represents a covalent bond, or a linker group selected from —C(O)— and —C(O)N($R^4$)—.

Appositely, Y represents a covalent bond, or a linker group selected from —C(O)—, —S(O)—, —$S(O)_2$—, —C(O)O—, —C(O)N($R^4$)— and —$S(O)_2N(R^4)$—.

Suitable values of Y include —C(O)—, —S(O)—, —$S(O)_2$—, —C(O)O—, —C(O)N($R^4$)— and —$S(O)_2N(R^4)$—.

Typical values of Y include —C(O)—, —C(O)N($R^4$)— and —C(O)C(O)—.

Selected values of Y include —C(O)— and —C(O)N($R^4$)—.

In a first embodiment, Y represents a covalent bond. In a second embodiment, Y represents —C(O)—. In a third embodiment, Y represents —S(O)—. In a fourth embodiment, Y represents —$S(O)_2$—. In a fifth embodiment, Y represents —C(O)O—. In a sixth embodiment, Y represents —C(O)N($R^4$)—. In a seventh embodiment, Y represents —C(O)C(O)—. In an eighth embodiment, Y represents —$S(O)_2N(R^4)$—. In a ninth embodiment, Y represents a group of formula (Ya) as defined above.

Generally, Z represents hydrogen; or Z represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

Appositely, Z represents $C_{1-6}$ alkyl, $C_{2-6}$ alkenyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$) alkyl, heteroaryl or heteroaryl($C_{1-6}$)alkyl, any of which groups may be optionally substituted by one or more substituents.

Typically, Z represents $C_{1-6}$ alkyl, $C_{3-7}$ cycloalkyl, $C_{3-7}$ cycloalkyl($C_{1-6}$)alkyl, $C_{3-7}$ heterocycloalkyl, $C_{3-7}$ heterocycloalkyl($C_{1-6}$)alkyl, aryl, aryl($C_{1-6}$)alkyl, heteroaryl or heteroaryl($C_{1-6}$)alkyl, any of which groups may be optionally substituted by one or more substituents.

More typically, Z represents $C_{3-7}$ cycloalkyl, $C_{3-7}$ heterocycloalkyl, aryl or heteroaryl, any of which groups may be optionally substituted by one or more substituents.

Suitably, Z represents $C_{3-7}$ cycloalkyl or aryl, either of which groups may be optionally substituted by one or more substituents.

In a first embodiment, Z represents hydrogen. In a second embodiment, Z represents optionally substituted $C_{1-6}$ alkyl. In a third embodiment, Z represents optionally substituted $C_{2-6}$ alkenyl. In a fourth embodiment, Z represents optionally substituted $C_{3-7}$ cycloalkyl. In a fifth embodiment, Z represents optionally substituted $C_{3-7}$ cycloalkyl($C_{1-6}$)alkyl.

In a sixth embodiment, Z represents optionally substituted $C_{3-7}$ heterocycloalkyl. In a seventh embodiment, Z represents optionally substituted $C_{3-7}$ heterocycloalkyl($C_{1-6}$)alkyl. In an eighth embodiment, Z represents optionally substituted aryl. In a ninth embodiment, Z represents optionally substituted aryl($C_{1-6}$)alkyl. In a tenth embodiment, Z represents optionally substituted heteroaryl. In an eleventh embodiment, Z represents optionally substituted heteroaryl ($C_{1-6}$)alkyl.

In a particular embodiment, Z is other than hydrogen.

Typical values of Z include methyl, ethyl, isopropenyl, cyclopropyl, indanyl, cyclopropylmethyl, cyclopentylethyl, dihydrobenzofuranyl, pyrrolidinyl, indolinyl, dihydrobenzofuranylmethyl, morpholinylmethyl, morpholinylethyl, phenyl, benzyl, phenylethyl, furyl, thienyl, indolyl, pyrazolyl, indazolyl, isoxazolyl, thiazolyl, benzothiazolyl, imidazolyl, benzimidazolyl, imidazo[1,2-a]pyridinyl, pyridinyl, quinolinyl, isoquinolinyl, pyridazinyl, pyrimidinyl, pyrazinyl, quinoxalinyl, indolylmethyl, thiazolylmethyl, imidazo[2,1-b]thiazolylmethyl, pyridinylmethyl, furylethyl, benzimidazolylethyl and pyridinylethyl, any of which groups may be optionally substituted by one or more substituents. Additional values include benzofuryl and benzothiadiazolyl, either of which groups may be optionally substituted by one or more substituents. Additional values include pyrazolo[4,3-c]pyridinyl, benzisoxazolyl and benzotriazolyl, any of which groups may be optionally substituted by one or more substituents.

Selected values of Z include indanyl, dihydrobenzofuranyl, phenyl, benzofuryl, indolyl, pyrazolo[4,3-c]pyridinyl, indazolyl, isoxazolyl, benzisoxazolyl, benzimidazolyl, imidazo[1,2-a]pyridinyl, benzothiadiazolyl, benzotriazolyl, pyridinyl, pyrimidinyl and pyrazinyl, any of which groups may be optionally substituted by one or more substituents.

Illustrative values of Z include indanyl, dihydrobenzofuranyl, phenyl, benzofuryl, indolyl, indazolyl, benzimidazolyl, benzothiadiazolyl, pyridinyl and pyrimidinyl, any of which groups may be optionally substituted by one or more substituents.

Suitable values of Z include indanyl and phenyl, either of which groups may be optionally substituted by one or more substituents.

In one embodiment, Z is unsubstituted. In another embodiment, Z is substituted by one or more substituents, typically by one, two or three substituents, suitably by one or two substituents. In one aspect of that embodiment, Z is monosubstituted. In another aspect of that embodiment, Z is disubstituted. In a further aspect of that embodiment, Z is trisubstituted.

Typical examples of optional substituents on Z include one or more substituents independently selected from halogen, cyano, nitro, $C_{1-6}$ alkyl, trifluoromethyl, cyano-($C_{1-6}$)alkyl, ($C_{3-7}$)heterocycloalkyl, halo($C_{3-7}$)heterocycloalkyl, ($C_{1-6}$)alkyl($C_{3-7}$)heterocycloalkyl, ($C_{2-6}$)alkoxycarbonyl ($C_{3-7}$)heterocycloalkyl, dihalo($C_{3-7}$)heterocycloalkyl, ($C_{3-7}$) heterocycloalkyl($C_{1-6}$)alkyl, ($C_{1-6}$)alkyl($C_{3-7}$)heterocycloalkyl ($C_{1-6}$)alkyl, heteroaryl, hydroxy, oxo, $C_{1-6}$ alkoxy, difluoromethoxy, trifluoromethoxy, ($C_{3-7}$)heterocycloalkoxy, ($C_{2-6}$)alkoxycarbonyl($C_{3-7}$)heterocycloalkoxy, ($C_{3-7}$)heterocycloalkyl($C_{1-6}$)alkoxy, aryloxy, haloaryloxy, ($C_{1-6}$)alkoxyaryloxy, $C_{1-3}$alkylenedioxy, dihalo($C_{1-3}$)alkylenedioxy, arylcarbonyloxy, $C_{1-6}$ alkylthio, $C_{1-6}$ alkylsulfinyl, $C_{1-6}$alkylsulfonyl, amino, $C_{1-6}$ alkylamino, di($C_{1-6}$) alkylamino, di($C_{1-6}$)alkylamino($C_{1-6}$)alkyl, arylamino, $C_{2-6}$ alkylcarbonylamino, $C_{2-6}$alkoxycarbonylamino, $C_{1-6}$alkylsulfonylamino, formyl, $C_{2-6}$ alkylcarbonyl, $C_{3-6}$cycloalkylcarbonyl, $C_{3-6}$ heterocycloalkylcarbonyl, carboxy, $C_{2-6}$ alkoxycarbonyl, aryloxycarbonyl, aminocarbonyl, $C_{1-6}$alkylaminocarbonyl, di($C_{1-6}$)alkylaminocarbonyl, aminosulfonyl, $C_{1-6}$alkylaminosulfonyl and di($C_{1-6}$)alkylaminosulfonyl. An additional example is trifluoroethoxy.

Selected examples of optional substituents on Z include one or more substituents independently selected from halogen, cyano, $C_{1-6}$ alkyl, trifluoromethyl, ($C_{3-7}$)-heterocycloalkyl, dihalo($C_{3-7}$)heterocycloalkyl, hydroxy, oxo, $C_{1-6}$ alkoxy, difluoromethoxy, trifluoromethoxy, trifluoroethoxy, $C_{1-6}$alkylsulfonyl, $C_{1-6}$ alkylamino and di($C_{1-6}$)alkylamino.

Illustrative examples of optional substituents on Z include one or more substituents independently selected from $C_{1-6}$ alkyl, ($C_{3-7}$)heterocycloalkyl, dihalo-($C_{3-7}$)heterocycloalkyl, hydroxy, oxo, $C_{1-6}$ alkoxy, difluoromethoxy, trifluoroethoxy, $C_{1-6}$ alkylamino and di($C_{1-6}$)alkylamino.

Suitable examples of optional substituents on Z include one or more substituents independently selected from $C_{1-6}$ alkyl and $C_{1-6}$ alkoxy.

Typical examples of specific substituents on Z include fluoro, chloro, bromo, cyano, nitro, methyl, ethyl, isopropyl, tert-butyl, trifluoromethyl, cyanomethyl, azetidinyl, pyrrolidinyl, piperazinyl, morpholinyl, fluoroazetidinyl, fluoropyrrolidinyl, methylpiperazinyl, tert-butoxycarbonylpiperazinyl, difluoroazetidinyl, difluoropyrrolidinyl, difluoropiperidinyl, pyrrolidinylmethyl, piperidinylmethyl, morpholinylmethyl, methylpiperazinylmethyl, pyrazolyl, imidazolyl, hydroxy, oxo, methoxy, difluoromethoxy, trifluoromethoxy, oxetanyloxy, azetidinyloxy, tetrahydrofuranyloxy, pyrrolidinyloxy, tert-butoxycarbonylazetidinyloxy, tert-butoxycarbonylpyrrolidinyloxy, tetrahydrofuranylmethoxy, morpholinylethoxy, phenoxy, chlorophenoxy, methoxyphenoxy, methylenedioxy, ethylenedioxy, difluoromethylenedioxy, benzoyloxy, methylthio, methylsulfinyl, methylsulfonyl, amino, methylamino, tert-butylamino, dimethylamino, dimethylaminomethyl, phenylamino, acetylamino, methoxycarbonylamino, methylsulfonylamino, formyl, acetyl, cyclopropylcarbonyl, azetidinylcarbonyl, pyrrolidinylcarbonyl, piperidinylcarbonyl, piperazinylcarbonyl, morpholinylcarbonyl, carboxy, methoxycarbonyl, ethoxycarbonyl, tert-butoxycarbonyl, benzyloxycarbonyl aminocarbonyl, methylaminocarbonyl, dimethylaminocarbonyl, aminosulfonyl, methylaminosulfonyl and dimethylaminosulfonyl. An additional example is trifluoroethoxy. An additional example is ethoxy.

Selected examples of specific substituents on Z include fluoro, chloro, cyano, methyl, ethyl, trifluoromethyl, azetidinyl, difluoroazetidinyl, hydroxy, oxo, methoxy, ethoxy, difluoromethoxy, trifluoromethoxy, trifluoroethoxy, methylsulfonyl, methylamino and dimethylamino.

Illustrative examples of specific substituents on Z include methyl, azetidinyl, difluoroazetidinyl, hydroxy, oxo, methoxy, difluoromethoxy, trifluoroethoxy, methylamino and dimethylamino.

Suitable examples of specific substituents on Z include methyl and methoxy.

Selected values of Z include include phenoxymethyl, chlorophenoxymethyl, methoxyphenoxymethyl, tert-butoxycarbonylmethyl, benzyloxycarbonylmethyl, phenoxyethyl, isopropenyl, cyclopropyl, indanyl, cyclopropylmethyl, cyclopentylethyl, (methyl)(oxo)pyrrolidinyl, dihydrobenzofuranyl, methylindolinyl, dihydrobenzofuranylmethyl, morpholinylmethyl, morpholinylethyl, phenyl, nitrophenyl, methylphenyl, ethylphenyl, cyanomethylphenyl, morpholinylphenyl, pyrazolylphenyl, imidazolylphenyl, methoxyphenyl, difluoromethoxyphenyl, trifluoromethoxyphenyl, morpholinylethoxyphenyl, ethylenedioxyphenyl, difluoromethylenedioxyphenyl, benzoyloxyphenyl, dimethylaminophenyl, acetylaminophenyl, aminocarbonylphenyl, (chloro)(methyl)phenyl, dimethylphenyl, (methyl)(trifluoromethyl)phenyl, bis(trifluoromethyl)phenyl, (fluoropyrrolidinyl)(methyl)phenyl, (methyl)(pyrrolidinylmethyl)phenyl, (methyl)-(morpholinylmethyl)phenyl, (methyl)(methylpiperazinylmethyl)phenyl, (fluoro)-(methoxy)phenyl, (chloro)(methoxy)phenyl, (cyano)(methoxy)phenyl, (methoxy)-(methyl)phenyl, (methoxy)(trifluoromethyl)phenyl, dimethoxyphenyl, (difluoromethoxy)-(methyl)phenyl, (methyl)(oxetanyloxy) phenyl, (azetidinyloxy)(methyl)phenyl, (tert-butoxycarbonylazetidinyloxy)(methyl)phenyl, (methyl)(tetrahydrofuranylmethoxy)-phenyl, (methyl)(morpholinylethoxy)phenyl, (dimethylaminomethyl)(methyl)phenyl, trimethoxyphenyl, benzyl, cyanobenzyl, methylbenzyl, methoxybenzyl, methylenedioxybenzyl, dimethylaminobenzyl, dimethoxybenzyl, phenylethyl, fluorophenylethyl, methylphenylethyl, (hydroxy)(phenyl)ethyl, methoxyphenylethyl, methylfuryl, thienyl, methylindolyl, pyrazolyl, methylpyrazolyl, dimethylpyrazolyl, indazolyl, dimethylisoxazolyl, thiazolyl, methylthiazolyl, tert-butylthiazolyl, ethoxycarbonylthiazolyl, benzothiazolyl, methoxybenzothiazolyl, methylimidazolyl, benzimidazolyl, methylbenzimidazolyl, trifluoromethylbenzimidazolyl, piperidinylmethylbenzimidazolyl, morpholinylmethylbenzimidazolyl, imidazo[1,2-a]pyridinyl, pyridinyl, chloropyridinyl, methylpiperazinylpyridinyl, methoxypyridinyl, dimethylpyridinyl, (methyl)-(trifluoromethyl)pyridinyl, (azetidinyl)(methyl)pyridinyl, (methyl)(pyrrolidinyl)pyridinyl, (methyl)(piperazinyl)pyridinyl, (fluoroazetidinyl)(methyl)pyridinyl, (fluoropyrrolidinyl)-(methyl)pyridinyl, (methyl)(methylpiperazinyl)pyridinyl, (tert-butoxycarbonyl-piperazinyl)(methyl)pyridinyl, (difluoroazetidinyl)(methyl)pyridinyl, (difluoropyrrolidinyl)(methyl)pyridinyl, (difluoropiperidinyl)(methyl)pyridinyl, (methyl)-(pyrrolidinylmethyl)pyridinyl, (methyl)(morpholinylmethyl)pyridinyl, (methyl)-(methylpiperazinylmethyl)pyridinyl, (chloro)(methoxy)pyridinyl, (methoxy)(methyl)-pyridinyl, (methoxy)(trifluoromethyl)pyridinyl, dimethoxypyridinyl, (difluoromethoxy)-(methyl)pyridinyl, (methyl)(tetrahydrofuranyloxy)pyridinyl, (methyl)(pyrrolidinyloxy)-pyridinyl, (tert-butoxycarbonylazetidinyloxy) (methyl)pyridinyl, (tert-butoxycarbonyl-pyrrolidinyloxy) (methyl)pyridinyl, (dimethylamino)(methyl)pyridinyl, quinolinyl, isoquinolinyl, methoxypyridazinyl, pyrimidinyl, methoxypyrimidinyl, (methoxy)-(methyl)pyrimidinyl, pyrazinyl, methoxypyrazinyl, (methoxy)(methyl)pyrazinyl, quinoxalinyl, indolylmethyl, thiazolylmethyl, methylthiazolylmethyl, imidazo[2,1-b]-thiazolylmethyl, pyridinylmethyl, furylethyl, benzimidazolylethyl and pyridinylethyl. Additional values include methoxybenzofuryl, indolyl, methylindazolyl, benzothiadiazolyl, (hydroxy)(methyl) pyridinyl, (methyl)(trifluoroethoxy)pyridinyl, (methyl)(methylamino) pyridinyl, (dimethyl)(oxo)pyridinyl, (difluoroazetidinyl) (methyl)-pyrimidinyl and (dimethylamino) (methyl)pyrimidinyl. Additional values include dichlorophenyl, (cyano) (methyl)phenyl, (fluoro)(trifluoromethoxy)phenyl, (chloro)-(trifluoromethoxy)phenyl, (methyl)(trifluoromethoxy) phenyl, (methyl)(methylsulfonyl)-phenyl, (chloro)(fluoro) (methyl)phenyl, methylpyrazolo[4,3-c]pyridinyl, ethylindazolyl, (fluoro)(methyl)indazolyl, (methyl)(trifluoromethyl)indazolyl, methylisoxazolyl, benzisoxazolyl, methylbenzotriazolyl, (cyano)(methyl) pyridinyl, (fluoro) (methoxy)-pyridinyl, (ethoxy)(fluoro) pyridinyl, (ethyl) (methoxy)pyridinyl, (ethoxy)(methyl)-pyridinyl, (difluoromethoxy)(methyl)pyridinyl, (methyl) (trifluoromethoxy) pyridinyl and (dimethylamino)(methyl) pyrazinyl.

Particular values of Z include include indanyl, dihydrobenzofuranyl, phenyl, methoxyphenyl, dimethylaminophenyl, dichlorophenyl, (chloro)(methyl)phenyl, (cyano)-(methyl)phenyl, (chloro)(methoxy)phenyl, (methoxy) (methyl)phenyl, (methoxy)-(trifluoromethyl)phenyl, (difluoromethoxy)(methyl)phenyl, (fluoro)(trifluoromethoxy)-phenyl, (chloro)(trifluoromethoxy)phenyl, (methyl)(trifluoromethoxy)phenyl, (methyl)-(methylsulfonyl)phenyl, (chloro)(fluoro)(methyl)phenyl, methoxybenzofuryl, indolyl, methylindolyl, methylpyrazolo[4,3-c]pyridinyl, indazolyl, methylindazolyl, ethylindazolyl, (fluoro) (methyl)indazolyl, (methyl)(trifluoromethyl)indazolyl, methylisoxazolyl, benzisoxazolyl, methylbenzimidazolyl, imidazo[1,2-a]pyridinyl, benzothiadiazolyl, methylbenzotriazolyl, (cyano)(methyl)pyridinyl, (azetidinyl)(methyl)-pyridinyl, (difluoroazetidinyl)(methyl)pyridinyl, (hydroxy) (methyl)pyridinyl, (fluoro)-(methoxy)pyridinyl, (chloro) (methoxy)pyridinyl, (ethoxy)(fluoro)pyridinyl, (methoxy)-(methyl)pyridinyl, (ethyl)(methoxy)pyridinyl, (ethoxy) (methyl)pyridinyl, (methoxy)-(trifluoromethyl)pyridinyl, dimethoxypyridinyl, (difluoromethoxy)(methyl)pyridinyl, (methyl)(trifluoromethoxy)pyridinyl, (methyl)(trifluoroethoxy)pyridinyl, (methyl)-(methylamino)pyridinyl, (dimethylamino)(methyl)pyridinyl, (dimethyl)(oxo)pyridinyl, (difluoroazetidinyl)(methyl)pyrimidinyl, (dimethylamino) (methyl)pyrimidinyl and (dimethylamino)(methyl) pyrazinyl.

Typical values of Z include include indanyl, dihydrobenzofuranyl, phenyl, methoxyphenyl, dimethylaminophenyl, (methoxy)(methyl)phenyl, (difluoromethoxy)-(methyl)phenyl, methoxybenzofuryl, indolyl, indazolyl, methylindazolyl, methylbenzimidazolyl, benzothiadiazolyl, (azetidinyl)(methyl)pyridinyl, (difluoroazetidinyl)-(methyl) pyridinyl, (hydroxy)(methyl)pyridinyl, (methoxy)(methyl) pyridinyl, (methyl)-(trifluoroethoxy)pyridinyl, (methyl) (methylamino)pyridinyl, (dimethylamino)(methyl)-pyridinyl, (dimethyl)(oxo)pyridinyl, (difluoroazetidinyl) (methyl) pyrimidinyl and (dimethylamino)(methyl) pyrimidinyl.

Illustrative values of Z include include indanyl, methoxyphenyl and (methoxy)(methyl)phenyl.

One particular value of Z is methoxyphenyl, especially 4-methoxyphenyl.

Another particular value of Z is (methoxy)(methyl)phenyl, especially 4-methoxy-2-methylphenyl or 4-methoxy-3-methylphenyl. In a first embodiment of that value, Z is 4-methoxy-2-methylphenyl. In a second embodiment of that value, Z is 4-methoxy-3-methylphenyl.

Another particular value of Z is (methyl)(trifluoromethoxy)phenyl, especially 2-methyl-4-trifluoromethoxyphenyl.

Another particular value of Z is indanyl, especially indan-5-yl.

Another particular value of Z is (difluoroazetidinyl)(methyl)pyridinyl, especially 6-(3,3-difluoroazetidin-1-yl)-2-methylpyridin-3-yl.

Another particular value of Z is (methoxy)(methyl)pyridinyl, especially 6-methoxy-2-methylpyridin-3-yl.

Another particular value of Z is (ethyl)(methoxy)pyridinyl, especially 2-ethyl-6-methoxypyridin-3-yl.

Another particular value of Z is (ethoxy)(methyl)pyridinyl, especially 6-ethoxy-2-methylpyridin-3-yl.

Another particular value of Z is dimethoxypyridinyl, especially 2,6-dimethoxypyridin-3-yl.

Generally, $A^1$ represents hydrogen, cyano or trifluoromethyl; or $A^1$ represents $C_{1-6}$ alkyl, optionally substituted by one or more substituents independently selected from —$OR^a$, —$NR^bR^c$, —$CO_2R^d$ and —$CONR^bR^c$; or $A^1$ represents $C_{3-7}$ cycloalkyl.

Typically, $A^1$ represents hydrogen or cyano; or $A^1$ represents $C_{1-6}$ alkyl, optionally substituted by one or more substituents independently selected from —$OR^a$, —$CO_2R^d$ and —$CONR^bR^c$; or $A^1$ represents $C_{3-7}$ cycloalkyl.

More typically, $A^1$ represents hydrogen or trifluoromethyl; or $A^1$ represents $C_{1-6}$ alkyl, optionally substituted by one or more substituents independently selected from fluoro and —$OR^a$.

Appositely, $A^1$ represents hydrogen; or $A^1$ represents $C_{1-6}$ alkyl, optionally substituted by —$OR^a$.

Suitably, $A^1$ represents hydrogen or $C_{1-6}$ alkyl.

In a first embodiment, $A^1$ represents hydrogen. In a second embodiment, $A^1$ represents cyano. In a third embodiment, $A^1$ represents trifluoromethyl. In a fourth embodiment, $A^1$ represents $C_{1-6}$ alkyl, optionally substituted by one or more substituents independently selected from fluoro, —$OR^a$, trifluoromethoxy, —$NR^bR^c$, —$CO_2R^d$ and —$CONR^bR^c$. In a first aspect of that embodiment, $A^1$ represents $C_{1-6}$ alkyl, optionally substituted by one or more substituents independently selected from —$OR^a$, —$NR^bR^c$, —$CO_2R^d$ and —$CONR^bR^c$. In a second aspect of that embodiment, $A^1$ represents $C_{1-6}$ alkyl, optionally substituted by one or more substituents independently selected from —$OR^a$, —$CO_2R^d$ and —$CONR^bR^c$. In a third aspect of that embodiment, $A^1$ represents $C_{1-6}$ alkyl, optionally substituted by one or more substituents independently selected from —$OR^a$ and —$NR^bR^c$. In a fourth aspect of that embodiment, $A^1$ represents $C_{1-6}$ alkyl, optionally substituted by one or more substituents independently selected from fluoro and —$OR^a$. In a fifth aspect of that embodiment, $A^1$ represents unsubstituted $C_{1-6}$ alkyl, typically methyl, ethyl, isopropyl or isobutyl, especially methyl. In a sixth aspect of that embodiment, $A^1$ represents $C_{1-6}$ alkyl monosubstituted by —$OR^a$, —$CO_2R^d$ or —$CONR^bR^c$. In a seventh aspect of that embodiment, $A^1$ represents $C_{1-6}$ alkyl monosubstituted by —$OR^a$ or —$NR^bR^c$. In an eighth aspect of that embodiment, $A^1$ represents $C_{1-6}$ alkyl disubstituted by two substituents independently selected from —$OR^a$ and —$NR^bR^c$. In an ninth aspect of that embodiment, $A^1$ represents $C_{1-6}$ alkyl trisubstituted by fluoro. In a fifth embodiment, $A^1$ represents $C_{3-7}$ cycloalkyl, especially cyclopropyl.

Selected values of $A^1$ include hydrogen, cyano, methyl, ethyl, isopropyl, isobutyl, —$CH_2OR^a$, —$CH_2CH_2OR^a$, —$CH_2CO_2R^d$, —$CH_2CONR^bR^c$ and cyclopropyl. Additional values include trifluoromethyl and trifluoroethyl.

Typical values of $A^1$ include hydrogen, methyl, ethyl, isopropyl, isobutyl, trifluoromethyl, trifluoroethyl —$CH_2OR^a$ and —$CH_2CH_2OR^a$.

Apposite values of $A^1$ include hydrogen, methyl, ethyl, isopropyl, isobutyl, trifluoromethyl, trifluoroethyl, hydroxymethyl and hydroxyethyl.

Illustrative values of $A^1$ include hydrogen, methyl and —$CH_2OR^a$.

Particular values of $A^1$ include hydrogen, methyl and hydroxymethyl.

Suitable values of $A^1$ include hydrogen and methyl.

In a particular embodiment, $A^2$ represents hydrogen. In another embodiment, $A^2$ represents $C_{1-6}$ alkyl, especially methyl.

Selected values of $A^2$ include hydrogen and methyl.

Suitably, $R^1$ represents hydrogen, halogen, cyano, nitro, hydroxy, trifluoromethyl, trifluoromethoxy, —$OR^a$, —$SO_2R^c$, —$NR^bR^c$, —$CH_2NR^bR^c$, —$NR^cCOR^d$, —$CH_2NR^cCOR^d$, —$NR^cCO_2R^d$, —$NHCONR^bR^c$, —$NR^cSO_2R^e$, —$NHSO_2NR^bR^c$, —$COR^d$, —$CO_2R^d$, —$CONR^bR^c$, —$CON(OR^a)R^b$ or —$SO_2NR^bR^c$; or $R^1$ represents $C_{1-6}$ alkyl, aryl or heteroaryl, any of which groups may be optionally substituted by one or more substituents.

Typically, $R^1$ represents hydrogen, —$NR^bR^c$ or —$NR^cCOR^d$; or $R^1$ represents $C_{1-6}$ alkyl, which group may be optionally substituted by one or more substituents.

Typical values of $R^1$ include cyano, —$OR^a$, —$SR^a$, —$SO_2R^a$ and —$NR^bR^c$.

Suitable values of $R^1$ include hydrogen and —$NR^bR^c$, especially —$NR^bR^c$.

In a first embodiment, $R^1$ represents hydrogen. In a second embodiment, $R^1$ represents cyano. In a third embodiment, $R^1$ represents —$OR^a$. In a fourth embodiment, $R^1$ represents —$SR^a$. In a fifth embodiment, $R^1$ represents —$SO_2R^a$. In a sixth embodiment, $R^1$ represents —$NR^bR^c$. In a seventh embodiment, $R^1$ represents —$NR^cCOR^d$. In an eighth embodiment, $R^1$ represents optionally substituted $C_{1-6}$ alkyl. In one aspect of that embodiment, $R^1$ represents optionally substituted methyl.

Examples of typical substituents on $R^1$ include one or more substituents independently selected from halogen, cyano, nitro, $C_{1-6}$ alkyl, trifluoromethyl, aryl($C_{1-6}$)alkyl, hydroxy, $C_{1-6}$ alkoxy, difluoromethoxy, trifluoromethoxy, aryloxy, $C_{1-4}$ alkylenedioxy, $C_{1-6}$ alkoxy($C_{1-6}$)alkyl, $C_{1-6}$ alkylthio, $C_{1-6}$ alkylsulphonyl, oxo, amino, $C_{1-6}$ alkylamino, di($C_{1-6}$)alkylamino, $C_{2-6}$alkylcarbonylamino, $C_{2-6}$alkoxycarbonylamino, aryl($C_{1-6}$)alkoxycarbonylamino, $C_{1-6}$alkylaminocarbonylamino, arylaminocarbonylamino, $C_{1-6}$ alkylsulphonylamino, formyl, $C_{2-6}$alkylcarbonyl, carboxy, $C_{2-6}$alkoxycarbonyl, aminocarbonyl, $C_{1-6}$alkylaminocarbonyl, di($C_{1-6}$)alkylaminocarbonyl, aminosulphonyl, $C_{1-6}$ alkylaminosulphonyl and di($C_{1-6}$)alkylamino sulphonyl.

Specific examples of typical substituents on $R^1$ include one or more substituents independently selected from fluoro, chloro, bromo, cyano, nitro, methyl, ethyl, tert-butyl, trifluoromethyl, benzyl, hydroxy, methoxy, difluoromethoxy, trifluoromethoxy, phenoxy, methylenedioxy, ethylenedioxy, methoxymethyl, methylthio, methylsulphonyl, oxo, amino, methylamino, dimethylamino, acetylamino, methoxycarbonylamino, ethoxycarbonylamino, benzyloxycarbonylamino, ethylaminocarbonylamino, butylaminocarbonylamino, phenylaminocarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl.

Generally, $R^2$ represents hydrogen, cyano, hydroxy, trifluoromethyl, —$NR^cCO_2R^d$, —$COR^d$, —$CO_2R^d$, —$CONR^bR^c$ or —$CON(OR^a)R^b$; or $C_{1-6}$ alkyl, $C_{3-7}$ cycloalkyl, aryl, $C_{3-7}$ heterocycloalkyl, $C_{3-7}$ heterocycloalkenyl or heteroaryl, any of which groups may be optionally substituted by one or more substituents.

Appositely, $R^2$ represents hydrogen or trifluoromethyl; or $R^2$ represents $C_{1-6}$ alkyl, aryl or heteroaryl, any of which groups may be optionally substituted by one or more substituents.

In a first embodiment, $R^2$ represents hydrogen. In a second embodiment, $R^2$ represents cyano. In a third embodiment, $R^2$ represents hydroxy. In a fourth embodiment, $R^2$ represents trifluoromethyl. In a fifth embodiment, $R^2$ represents —$NR^cCO_2R^d$. In a sixth embodiment, $R^2$ represents —$COR^d$. In a seventh embodiment, $R^2$ represents —$CO_2R^d$. In an eighth embodiment, $R^2$ represents —$CONR^bR^c$. In a ninth embodiment, $R^2$ represents —$CON(OR^a)R^b$. In a tenth embodiment, $R^2$ represents optionally substituted $C_{1-6}$ alkyl. In a first aspect of that embodiment, $R^2$ represents unsubstituted $C_{1-6}$ alkyl. In a second aspect of that embodiment, $R^2$ represents monosubstituted $C_{1-6}$ alkyl. In a third aspect of that embodiment, $R^2$ represents disubstituted $C_{1-6}$ alkyl. In an eleventh embodiment, $R^2$ represents optionally substituted $C_{3-7}$ cycloalkyl. In a first aspect of that embodiment, $R^2$ represents unsubstituted $C_{3-7}$ cycloalkyl. In a second aspect of that embodiment, $R^2$ represents monosubstituted $C_{3-7}$ cycloalkyl. In a third aspect of that embodiment, $R^2$ represents disubstituted $C_{3-7}$ cycloalkyl. In a twelfth embodiment, $R^2$ represents optionally substituted aryl. In a first aspect of that embodiment, $R^2$ represents unsubstituted aryl. In a second aspect of that embodiment, $R^2$ represents monosubstituted aryl. In a third aspect of that embodiment, $R^2$ represents disubstituted aryl. In a thirteenth embodiment, $R^2$ represents optionally substituted $C_{3-7}$ heterocycloalkyl. In a first aspect of that embodiment, $R^2$ represents unsubstituted $C_{3-7}$ heterocycloalkyl. In a second aspect of that embodiment, $R^2$ represents monosubstituted $C_{3-7}$ heterocycloalkyl. In a third aspect of that embodiment, $R^2$ represents disubstituted $C_{3-7}$ heterocycloalkyl. In a fourteenth embodiment, $R^2$ represents optionally substituted $C_{3-7}$ heterocycloalkenyl. In a first aspect of that embodiment, $R^2$ represents unsubstituted $C_{3-7}$ heterocycloalkenyl. In a second aspect of that embodiment, $R^2$ represents monosubstituted $C_{3-7}$ heterocycloalkenyl. In a third aspect of that embodiment, $R^2$ represents disubstituted $C_{3-7}$ heterocycloalkenyl. In a fifteenth embodiment, $R^2$ represents optionally substituted heteroaryl. In a first aspect of that embodiment, $R^2$ represents unsubstituted heteroaryl. In a second aspect of that embodiment, $R^2$ represents monosubstituted heteroaryl. In a third aspect of that embodiment, $R^2$ represents disubstituted heteroaryl.

Where $R^2$ represents optionally substituted $C_{1-6}$ alkyl, suitable values include methyl, ethyl, n-propyl, isopropyl, n-butyl, isobutyl and tert-butyl, any of which groups may be optionally substituted by one or more substituents. Selected values include methyl, hydroxymethyl, chloropropyl and isobutyl. Particular values include methyl and isobutyl, especially methyl.

Where $R^2$ represents optionally substituted $C_{3-7}$ cycloalkyl, a suitable value is cyclohexyl, optionally substituted by one or more substituents.

Where $R^2$ represents optionally substituted aryl, a suitable value is phenyl, optionally substituted by one or more substituents. Selected values include phenyl, fluorophenyl, chlorophenyl and methoxyphenyl.

Where $R^2$ represents optionally substituted $C_{3-7}$ heterocycloalkyl, typical values include azetidinyl, pyrrolidinyl, piperidinyl, piperazinyl, morpholinyl and thiomorpholinyl, any of which groups may be optionally substituted by one or more substituents.

Where $R^2$ represents optionally substituted $C_{3-7}$ heterocycloalkenyl, a typical value is oxazolinyl, optionally substituted by one or more substituents. Suitable values include oxazolinyl, methyloxazolinyl, isopropyloxazolinyl and dimethyloxazolinyl.

Where $R^2$ represents optionally substituted heteroaryl, typical values include pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl and triazinyl, any of which groups may be optionally substituted by one or more substituents. Suitable values include oxadiazolyl and pyridinyl, either of which groups may be optionally substituted by one or more substituents. Selected values include methyloxadiazolyl, isopropyloxadiazolyl, tert-butyloxadiazolyl and pyridinyl.

In a selected embodiment, $R^2$ represents hydrogen, cyano, hydroxy, trifluoromethyl, $—NR^cCO_2R^d$, $—COR^d$, $—CO_2R^d$, $—CONR^bR^c$ or $—CON(OR^a)R^b$; or $R^2$ represents $C_{1-6}$ alkyl, cyclohexyl, phenyl, oxazolinyl, oxadiazolyl or pyridinyl, any of which groups may be optionally substituted by one or more substituents.

In a particular aspect of that embodiment, $R^2$ represents hydrogen or trifluoromethyl; or $R^2$ represents $C_{1-6}$ alkyl, phenyl or pyridinyl, any of which groups may be optionally substituted by one or more substituents.

Typical examples of optional substituents on $R^2$ include one or more substituents independently selected from halogen, cyano, nitro, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$alkylcarbonylamino, $C_{2-6}$ alkoxycarbonylamino, $C_{1-6}$alkylsulfonylamino, formyl, $C_{2-6}$alkylcarbonyl, carboxy, $C_{2-6}$ alkoxycarbonyl, aminocarbonyl, $C_{1-6}$alkylaminocarbonyl, di($C_{1-6}$)alkylaminocarbonyl, aminosulfonyl, $C_{1-6}$alkylaminosulfonyl and di($C_{1-6}$) alkylaminosulfonyl.

Suitable examples of optional substituents on $R^2$ include halogen.

Typical examples of specific substituents on $R^2$ include one or more substituents independently selected from fluoro, chloro, bromo, cyano, nitro, methyl, ethyl, isopropyl, tert-butyl, trifluoromethyl, hydroxy, methoxy, isopropoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl and dimethylaminosulfonyl.

Typical examples of specific substituents on $R^2$ include fluoro.

Typical values of $R^2$ include hydrogen, cyano, hydroxy, trifluoromethyl, $—NR^cCO_2R^d$, $—COR^d$, $—CO_2R^d$, $—CONR^bR^c$, $—CON(OR^a)R^b$, methyl, hydroxymethyl, chloropropyl, isobutyl, cyclohexyl, phenyl, fluorophenyl, chlorophenyl, methoxyphenyl, oxazolinyl, methyloxazolinyl, isopropyloxazolinyl, dimethyloxazolinyl, methyloxadiazolyl, isopropyloxadiazolyl, tert-butyloxadiazolyl and pyridinyl.

Selected values of $R^2$ include hydrogen, trifluoromethyl, methyl, fluorophenyl and pyridinyl.

Typically, $R^2$ represents hydrogen, trifluoromethyl or $C_{1-6}$ alkyl.

Illustrative values of $R^2$ include hydrogen, trifluoromethyl and methyl.

Suitably, $R^2$ represents hydrogen.

Generally, $R^3$ represents hydrogen; or $R^3$ represents $C_{1-6}$ alkyl, optionally substituted by one or two halogen atoms.

Typically, $R^3$ represents hydrogen or $C_{1-6}$ alkyl.

Suitable values of $R^3$ include hydrogen and methyl.

In one embodiment, $R^3$ represents hydrogen. In another embodiment, $R^3$ represents $C_{1-6}$ alkyl, especially methyl.

Suitably, $R^4$ represents hydrogen or $C_{1-6}$ alkyl.

Suitable values of $R^4$ include hydrogen and methyl.

In one embodiment, $R^4$ represents hydrogen. In another embodiment, $R^4$ represents $C_{1-6}$ alkyl, optionally substituted by one or more substituents independently selected from $—OR^a$ and $—NR^bR^c$. In one aspect of that embodiment, $R^4$ represents unsubstituted $C_{1-6}$ alkyl, especially methyl. In another aspect of that embodiment, $R^4$ represents $C_{1-6}$ alkyl monosubstituted by $—OR^a$ or $—NR^bR^c$. In a further aspect of that embodiment, $R^4$ represents $C_{1-6}$ alkyl disubstituted by two substituents independently selected from —$OR^a$ and —$NR^bR^c$.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$alkylcarbonyl, carboxy, $C_{2-6}$alkoxycarbonyl, $C_{2-6}$alkylcarbonyloxy, amino, $C_{1-6}$ alkylamino, di($C_{1-6}$)alkylamino, phenylamino, pyridinylamino, $C_{2-6}$alkylcarbonylamino, $C_{2-6}$alkylcarbonylamino($C_{1-6}$)alkyl, $C_{2-6}$alkoxycarbonylamino, $C_{1-6}$ alkylsulphonylamino, aminocarbonyl, $C_{1-6}$alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, acetylaminomethyl, tert-butoxycarbonylamino, methylsulphonylamino, aminocarbonyl, methylaminocarbonyl and dimethylaminocarbonyl.

Typically, $R^a$ represents hydrogen; or $R^a$ represents $C_{1-6}$ alkyl, aryl($C_{1-6}$)alkyl or heteroaryl($C_{1-6}$)alkyl, any of which groups may be optionally substituted by one or more substituents.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Apposite values of $R^a$ include hydrogen; and methyl, ethyl, benzyl or isoindolylpropyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents hydrogen. In another embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

Appositely, $R^a$ represents hydrogen or $C_{1-6}$ alkyl.

Individual values of $R^a$ include hydrogen and methyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$alkoxycarbonyl, di($C_{1-6}$) alkylamino and $C_{2-6}$alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tertbutoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$alkylcarbonyl and $C_{2-6}$alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$alkylcarbonyl, carboxy, $C_{2-6}$alkoxycarbonyl, amino, $C_{2-6}$alkylcarbonylamino, $C_{2-6}$alkylcarbonylamino ($C_{1-6}$)alkyl, $C_{2-6}$alkoxycarbonylamino, $C_{1-6}$alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethylazetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxooxazolidin-3-yl, hydroxyisoxazolidin-2-yl, thiazolidin-3-yl, oxothiazolidin-3-yl, dioxoisothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl or ethyl, particularly methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, ethyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Appositely, $R^d$ represents hydrogen or $C_{1-6}$ alkyl.

Individual values of $R^d$ include hydrogen and methyl.

A particular value of $R^d$ is ethyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

In a particular aspect, the present invention provides a compound of formula (IA), or a pharmaceutically acceptable salt or solvate thereof:

(IA)

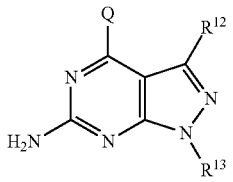

wherein Q is as defined above;

$R^{12}$ represents hydrogen, trifluoromethyl or $C_{1-6}$ alkyl; and $R^{13}$ represents hydrogen or $C_{1-6}$ alkyl.

Suitably, $R^{12}$ represents hydrogen or $C_{1-6}$ alkyl.

Suitable values of $R^{12}$ include hydrogen, trifluoromethyl and methyl.

In a first embodiment, $R^{12}$ represents hydrogen. In a second embodiment, $R^{12}$ represents trifluoromethyl. In third embodiment, $R^{12}$ represents $C_{1-6}$ alkyl, especially methyl.

Suitable values of $R^{13}$ include hydrogen and methyl.

In one embodiment, $R^{13}$ represents hydrogen. In another embodiment, $R^{13}$ represents $C_{1-6}$ alkyl, especially methyl.

One sub-class of compounds according to the invention is represented by the compounds of formula (IIA), and pharmaceutically acceptable salts and solvates thereof:

(IIA)

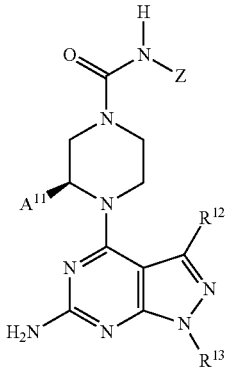

wherein $A^{11}$ represents hydrogen, cyano, $C_{1-6}$ alkyl, trifluoromethyl, $—CH_2CF_3$, $—CH_2OR^a$, $—CH_2CH_2OR^a$, $—CH_2CO_2R^d$, $—CH_2CONR^bR^c$ or $C_{3-7}$cycloalkyl; and Z, $R^{12}$, $R^{13}$, $R^a$, $R^b$, $R^c$ and $R^d$ are as defined above.

In a first embodiment, $A^{11}$ represents hydrogen. In a second embodiment, $A^{11}$ represents cyano. In a third embodiment, $A^{11}$ represents $C_{1-6}$ alkyl, typically methyl, ethyl, isopropyl or isobutyl, particularly methyl or ethyl, especially methyl. In a fourth embodiment, $A^{11}$ represents trifluoromethyl. In a fifth embodiment, $A^{11}$ represents $—CH_2CF_3$. In a sixth embodiment, $A^{11}$ represents $—CH_2OR^a$. In a seventh embodiment, A represents $—CH_2CH_2OR^a$. In an eighth embodiment, $A^{11}$ represents $—CH_2CO_2R^d$. In a ninth embodiment, $A^{11}$ represents $—CH_2CONR^bR^c$. In a tenth embodiment, $A^{11}$ represents $C_{3-7}$cycloalkyl, especially cyclopropyl.

Generally, $A^{11}$ represents hydrogen, cyano, $C_{1-6}$ alkyl, $—CH_2OR^a$, $—CH_2CH_2OR^a$, $—CH_2CO_2R^d$, $—CH_2CONR^bR^c$ or $C_{3-7}$cycloalkyl.

Selected values of $A^{11}$ include hydrogen, cyano, methyl, ethyl, isopropyl, isobutyl, $—CH_2OR^a$, $—CH_2CH_2OR^a$, $—CH_2CO_2R^d$, $—CH_2CONR^bR^c$ and cyclopropyl.

Suitably, $A^{11}$ represents hydrogen, $C_{1-6}$ alkyl, trifluoromethyl, $—CH_2CF_3$, $—CH_2OR^a$ or $—CH_2CH_2OR^a$.

Suitable values of $A^{11}$ include hydrogen, methyl, ethyl, isopropyl, isobutyl, trifluoromethyl, $—CH_2CF_3$, hydroxymethyl and hydroxyethyl.

Typically, $A^{11}$ represents hydrogen, $C_{1-6}$ alkyl or $—CH_2OR^a$.

Particular values of $A^{11}$ include hydrogen, methyl and hydroxymethyl.

Suitable values of $A^{11}$ include hydrogen and methyl.

In a selected embodiment, $A^{11}$ represents methyl, ethyl or hydroxyethyl. In a first aspect of that embodiment, $A^{11}$ represents methyl. In a second aspect of that embodiment, $A^{11}$ represents ethyl. In a third aspect of that embodiment, $A^{11}$ represents hydroxyethyl.

Another sub-class of compounds according to the invention is represented by the compounds of formula (IIB), and pharmaceutically acceptable salts and solvates thereof:

(IIB)

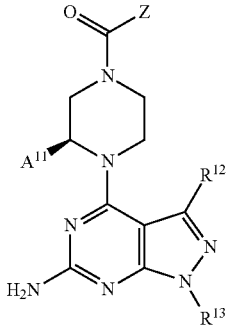

wherein Z, $A^{11}$, $R^{12}$ and $R^{13}$ are as defined above.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments. These include inflammatory, autoimmune and oncological disorders; viral diseases and malaria; and organ and cell transplant rejection.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis and spontaneous infertility.

Oncological disorders, which may be acute or chronic, include proliferative disorders, especially cancer, in animals, including mammals, especially humans. Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle.

Viral diseases include infections caused by various families of virus, including the Retroviridae, Flaviviridae, Picornaviridae. Various genera within the Retroviridae family include Alpharetrovirus, Betaretrovirus, Gammaretrovirus, Deltaretrovirus, Epsilonretrovirus, Lentivirus and Spumavirus. Members of the Lentivirus genus include human immunodeficiency virus 1 (HIV-1) and human immunodeficiency virus 2 (HIV-2). Various genera within the Flaviviridae family include Flavivirus, Pestivirus, Hepacivirus and Hepatitis G Virus. Members of the Flavivirus genus include Dengue fever virus, yellow fever virus, West Nile encephalitis virus and Japanese encephalitis virus. Members of the Pestivirus genus include bovine viral diarrhoea virus (BVDV), classical swine fever virus and border disease virus 2 (BDV-2). Members of the Hepacivirus genus include hepatitis C virus (HCV). Members of the Hepatitis G Virus genus include hepatitis G virus. Various genera within the Picornaviridae family include Aphthovirus, Avihepatovirus, Cardiovirus, Enterovirus, Erbovirus, Hepatovirus, Kobuvirus, Parechovirus, Sapelovirus, Senecavirus, Teschovirus and Tremovirus. Members of the Enterovirus genus include poliovirus, coxsackie A virus, coxsackie B virus and rhinovirus.

Organ transplant rejection includes the rejection of transplanted or grafted organs or cells (both allografts and xenografts), including graft-versus-host reaction disease. The term "organ" as used herein means all organs or parts of organs in mammals, particularly humans, including kidney, lung, bone marrow, hair, cornea, eye (vitreous), heart, heart valve, liver, pancreas, blood vessel, skin, muscle, bone, intestine and stomach. The term "rejection" as used herein means all reactions of the recipient body or the transplanted organ which ultimately lead to cell or tissue death in the transplanted organ, or adversely affect the functional ability and viability of the transplanted organ or the recipient. In particular, this means acute and chronic rejection reactions.

Cell transplant rejection includes the rejection of cell transplants and xenotransplantation. The major hurdle for xenotransplantation is that even before the T lymphocytes (responsible for the rejection of allografts) are activated, the innate immune system (especially T-independent B lymphocytes and macrophages) is activated. This provokes two types of severe and early acute rejection, referred to as hyperacute rejection and vascular rejection respectively. Conventional immunosuppressant drugs, including cyclosporine A, are ineffective in xenotransplantation. The compounds in accordance with the present invention are not liable to this drawback. The ability of the compounds of this invention to suppress T-independent xeno-antibody production as well as macrophage activation may be demonstrated by their ability to prevent xenograft rejection in athymic, T-deficient mice receiving xenogenic hamster-heart grafts.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

(III)

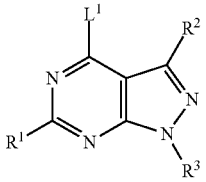

(IV)

wherein Q, $R^1$, $R^2$ and $R^3$ are as defined above, and $L^1$ represents a suitable leaving group.

The leaving group $L^1$ is typically a halogen atom, e.g. chloro.

The reaction will generally be carried out in the presence of a base, typically an organic amine such as N,N-diisopropylethylamine. The reaction is conveniently effected at ambient or elevated temperature in a suitable solvent, e.g. a cyclic ether solvent such as 1,4-dioxane, or a dipolar aprotic solvent such as N,N-dimethylformamide, or a $C_{1-6}$ alkanol such as n-butanol.

In another procedure, the compounds of formula (I) above wherein Y represents —C(O)—, —$S(O)_2$— or —C(O)O— may be prepared by a process which comprises reacting a compound of formula $L^2$-C(O)—Z, $L^2$-$S(O)_2$—Z or $L^2$-C(O)O—Z respectively with a compound of formula (VA), (VB), (VC), (VD) or (VE):

(VA)

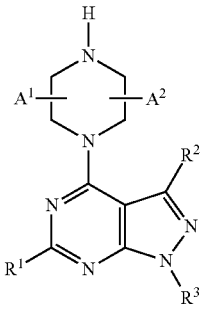

(VB)

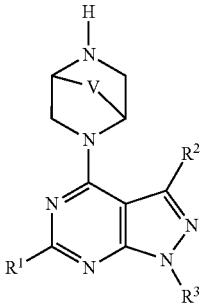

(VC)

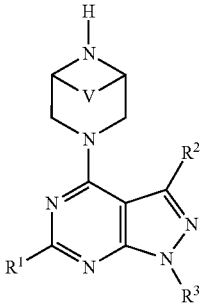

(VD)

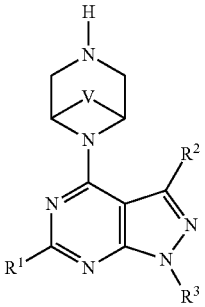

(VE)

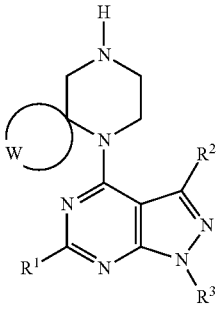

wherein V, W, Z, $A^1$, $A^2$, $R^1$, $R^2$ and $R^3$ are as defined above, and $L^2$ represents a suitable leaving group.

The leaving group $L^2$ is typically a halogen atom, e.g. chloro.

The reaction is conveniently effected at ambient temperature in a suitable solvent, e.g. an ethereal solvent such as 1,4-dioxane, or a chlorinated solvent such as dichloromethane, typically in the presence of a base. A suitable base for use in the reaction may be an organic base such as N,N-diisopropylethylamine, or an inorganic base such as potassium carbonate.

Alternatively, the leaving group $L^2$ may be 2-methyl-3-(trifluoromethylsulfonyl)-1H-imidazol-3-ium-1-yl, in which case the reaction may conveniently be effected at ambient temperature in an organic solvent such as acetonitrile.

In a variant procedure, the compounds of formula (I) above wherein Y represents —C(O)— may be prepared by a process which comprises reacting a compound of formula (VA), (VB), (VC), (VD) or (VE) as defined above with a compound of formula Z—$CO_2$H. Similarly, the compounds of formula (I) above wherein Y represents —C(O)C(O)— may be prepared by a process which comprises reacting a compound of formula (VA), (VB), (VC), (VD) or (VE) as defined above with a compound of formula Z—C(O)$CO_2$H.

The reaction is conveniently effected at ambient temperature in a suitable solvent, e.g. a dipolar aprotic solvent such as N,N-dimethylformamide, typically in the presence of a coupling reagent and a base. A suitable coupling reagent for use in the reaction may be O-(7-azabenzotriazol-1-yl)-N,N,N',N'-tetramethyluronium hexafluorophosphate (HATU). A suitable base for use in the reaction may be an organic base such as N,N-diisopropylethylamine.

In another procedure, the compounds of formula (I) above wherein Y represents —C(O)NH— may be prepared by a process which comprises reacting a compound of formula (VA), (VB), (VC), (VD) or (VE) as defined above with an isocyanate derivative of formula Z—N═C═O, wherein Z is as defined above.

The reaction is conveniently effected at a suitable temperature, e.g. ambient temperature or a temperature in the region of 0° C., in a suitable solvent or mixture of solvents. Such solvent or solvents may typically be selected as appropriate from an ethereal solvent such as 1,4-dioxane or tetrahydrofuran, a chlorinated solvent such as dichloromethane, a nitrile-containing solvent such as acetonitrile, and a dipolar aprotic solvent such as N,N-dimethylformamide. The reaction may optionally be performed in the presence of a base, e.g. an organic base such as diisopropylamine, N,N-diisopropylethylamine or triethylamine.

Alternatively, the compounds of formula (I) above wherein Y represents —C(O)NH— may be prepared by a process which comprises reacting a compound of formula (VA), (VB), (VC), (VD) or (VE) as defined above with a compound of formula Z—$NH_2$, wherein Z is as defined above, in the presence of triphosgene or 1,1'-carbonyldiimidazole.

The reaction is conveniently effected at ambient temperature in a suitable solvent, e.g. a chlorinated solvent such as dichloromethane, or a dipolar aprotic solvent such as N,N-dimethylformamide, typically in the presence of a base, e.g. an organic base such as N,N-diisopropylethylamine.

Alternatively, the compounds of formula (I) above wherein Y represents —C(O)NH— may be prepared by a two-step process which comprises: (i) reacting a compound of formula Z—$NH_2$, wherein Z is as defined above, with phenyl chloroformate; and (ii) reacting the material thereby obtained with a compound of formula (VA), (VB), (VC), (VD) or (VE) as defined above.

Step (i) of the above process is conveniently effected at a suitable temperature, e.g. ambient temperature or a temperature in the region of 0° C., in a suitable solvent, e.g. a cyclic ether solvent such as tetrahydrofuran, or a chlorinated solvent such as dichloromethane, or a nitrile-containing solvent such as acetonitrile, typically in the presence of a base, e.g. an organic base such as pyridine or triethylamine. Step (ii) is conveniently effected at ambient or elevated temperature in a suitable solvent, e.g. a sulfoxide solvent such as dimethyl sulfoxide or a nitrile-containing solvent such as acetonitrile, typically in the presence of a base, e.g. an organic base such as N,N-diisopropylethylamine.

In a further procedure, the compounds of formula (I) above wherein Y represents —S($O_2$)NH— may be prepared by a two-step process which comprises: (i) reacting a compound of formula (VA), (VB), (VC), (VD) or (VE) as defined above with methyl trifluoromethanesulfonate; and (ii) reacting the material thereby obtained with a compound of formula Z—$NH_2$, wherein Z is as defined above.

Step (i) of the above process is conveniently effected at a temperature in the region of 0° C. in a suitable solvent, typically a chlorinated solvent such as dichloromethane. Step (ii) is conveniently effected at an elevated temperature in a suitable solvent, e.g. a nitrile-containing solvent such as acetonitrile.

In a further procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted $C_{3-7}$ heterocycloalkyl($C_{1-6}$)alkyl, optionally substituted aryl($C_{1-6}$)alkyl or optionally substituted heteroaryl($C_{1-6}$)alkyl, may be prepared by a process which comprises reacting a compound of formula (VA), (VB), (VC), (VD) or (VE) as defined above with a compound of formula $Z^1$-$L^3$ wherein $Z^1$ represents $C_{1-6}$ alkyl, $C_{3-7}$ cycloalkyl($C_{1-6}$)alkyl, aryl($C_{1-6}$)alkyl, $C_{3-7}$ heterocycloalkyl-($C_{1-6}$)alkyl or heteroaryl($C_{1-6}$)alkyl, any of which groups may be optionally substituted by one or more substituents, and $L^3$ represents a suitable leaving group.

The leaving group $L^3$ is typically a halogen atom.

The reaction is conveniently effected at ambient temperature in a suitable solvent, e.g. a dipolar aprotic solvent such as N,N-dimethylformamide, or a chlorinated solvent such as dichloromethane, typically in the presence of a base. A suitable base for use in the reaction may be an organic base such as triethylamine, or an inorganic base such as caesium carbonate.

In a variant procedure, the compounds of formula (I) above wherein Y represents a covalent bond, and Z represents optionally substituted $C_{1-6}$ alkyl, optionally substituted $C_{3-7}$ cycloalkyl($C_{1-6}$)alkyl, optionally substituted $C_{3-7}$ heterocycloalkyl($C_{1-6}$)alkyl, optionally substituted aryl($C_{1-6}$)alkyl or optionally substituted heteroaryl($C_{1-6}$)alkyl, may be prepared by a two-step process which comprises: (i) reacting a compound of formula (VA), (VB), (VC), (VD) or (VE) as defined above with a compound of formula $Z^2$—CHO, wherein $Z^2$—$CH_2$— corresponds to a group of formula $Z^1$— as defined above; and (ii) reacting the material thereby obtained with a reducing agent.

Steps (i) and (ii) of the above process are conveniently effected at ambient temperature in a suitable solvent, e.g. a $C_{1-4}$ alkanol such as methanol. Step (i) is typically performed in the presence of a base, e.g. an organic base such as triethylamine. The reducing agent for use in step (ii) may suitably be an alkali metal borohydride such as sodium borohydride.

The compounds of formula (I) above wherein Y represents a linker group of formula (Ya) as defined above may be prepared by a process which comprises reacting a compound of formula (VA), (VB), (VC), (VD) or (VE) as defined above with a compound of formula (VI):

(VI)

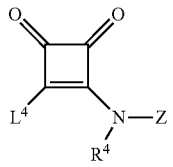

wherein Z and $R^4$ are as defined above, and $L^4$ represents a suitable leaving group.

The leaving group $L^4$ is typically a $C_{1-4}$ alkoxy group, e.g. ethoxy.

The reaction is conveniently effected at ambient temperature in a suitable solvent, e.g. a lower alkanol such as ethanol, typically in the presence of a base, e.g. an organic base such as triethylamine.

The intermediates of formula (VA), (VB), (VC), (VD) or (VE) above may be prepared by reacting a compound of formula (III) as defined above with a compound of formula (VIIA), (VIIB), (VIIC), (VIID) or (VIIE):

(VIIA)

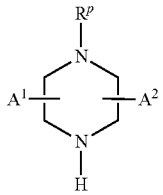

(VIIB)

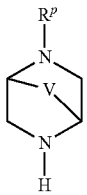

(VIIC)

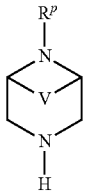

(VIID)

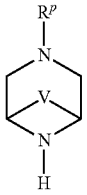

-continued (VIIE)

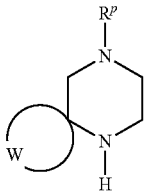

wherein V, W, $A^1$ and $A^2$ are as defined above, and $R^p$ represents hydrogen or an N-protecting group; followed, as necessary, by removal of the N-protecting group $R^p$.

The N-protecting group $R^p$ is typically tert-butoxycarbonyl (BOC). Alternatively, the N-protecting group $R^p$ may typically be benzyl.

The reaction between compound (III) and compound (VIIA), (VIIB), (VIIC), (VIID) or (VIIE) is conveniently accomplished under conditions analogous to those described above for the reaction between compounds (III) and (IV).

Alternatively, the reaction between compound (III) and compound (VIIA), (VIIB), (VIIC), (VIID) or (VIIE) may be accomplished at a suitable temperature (ambient or elevated) in a solvent such as acetonitrile or N,N-dimethylformamide, ideally in the presence of a coupling agent such as benzotriazol-1-yloxytris(dimethylamino)-phosphonium hexafluorophosphate (BOP) or (benzotriazol-1-yloxy)tripyrrolidinophosphonium hexafluorophosphate (PyBOP), and a base, e.g. an organic base such as 1,8-diazabicyclo[5.4.0]undec-7-ene (DBU).

Where the N-protecting group $R^p$ is BOC, subsequent removal of the BOC group may typically be accomplished by treatment with an acid, e.g. a mineral acid such as hydrochloric acid, or an organic acid such as trifluoroacetic acid. Alternatively, the BOC group may be removed by treatment with trimethylsilyl trifluoromethanesulfonate and 2,6-lutidine, typically at ambient temperature in a suitable solvent, e.g. a chlorinated solvent such as dichloromethane.

Where the N-protecting group $R^p$ is benzyl, subsequent removal of the benzyl group may typically be accomplished by treatment with a hydrogenation catalyst such as palladium on charcoal, suitably at an elevated temperature in the presence of ammonium formate.

The intermediates of formula (III) above may be prepared by reacting a compound of formula $R^3$—N(H)$NH_2$ with a compound of formula (VIII):

(VIII)

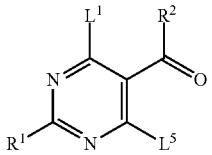

wherein $R^1$, $R^2$, $R^3$ and $L^1$ are as defined above, and $L^5$ represents a suitable leaving group.

The leaving group $L^5$ is typically a halogen atom, e.g. chloro.

The reaction will generally be carried out in the presence of a base, typically an organic amine such as triethylamine. The reaction is conveniently effected at ambient or elevated temperature in a suitable solvent, e.g. a cyclic ether solvent such as tetrahydrofuran.

Similarly, the intermediates of formula (VA), (VB), (VC), (VD) or (VE) above may be prepared by reacting a compound of formula $R^3$—N(H)$NH_2$ with a compound of formula (IXA), (IXB), (IXC), (IXD) or (IXE):

(IXA)

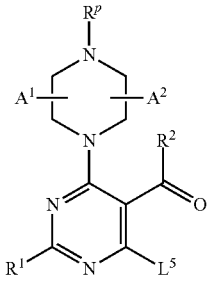

(IXB)

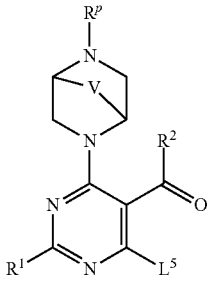

(IXC)

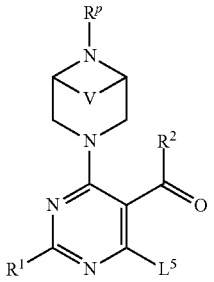

(IXD)

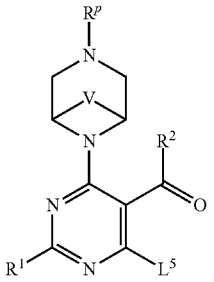

(IXE)

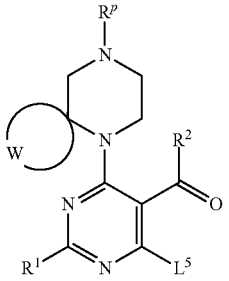

wherein V, W, $A^1$, $A^2$, $R^1$, $R^2$, $R^3$, $R^p$ and $L^5$ are as defined above; under conditions analogous to those described above for the reaction between $R^3$—N(H)$NH_2$ and compound (VIII); followed, as necessary, by removal of the N-protecting group $R^p$, as described above.

The intermediates of formula (IXA), (IXB), (IXC), (IXD) or (IXE) above may be prepared by reacting a compound of formula (VIIA), (VIIB), (VIIC), (VIID) or (VIIE) as defined above with a compound of formula (VIII) as defined above; under conditions analogous to those described above for the reaction between compound (III) and a compound of formula (VIIA), (VIIB), (VIIC), (VIID) or (VIIE).

As will be appreciated, the intermediates of formula (VA), (VB), (VC), (VD) and (VE) correspond to compounds in accordance with the present invention wherein Y represents a covalent bond and Z is hydrogen. Similarly, the intermediates of formula (VIIA), (VIIB), (VIIC), (VIID) or (VIIE) wherein $R^p$ is hydrogen correspond to intermediates of formula (IV) wherein Y represents a covalent bond and Z is hydrogen. Likewise, the intermediates of formula (VIIA), (VIIB), (VIIC), (VIID) or (VIIE) wherein $R^p$ is BOC correspond to intermediates of formula (IV) wherein Y represents —C(O)O— and Z is tert-butyl. The intermediates of formula (VIIA), (VIIB), (VIIC), (VIID) or (VIIE) wherein $R^p$ is benzyl correspond to intermediates of formula (IV) wherein Y represents a covalent bond and Z is benzyl.

Where they are not commercially available, the starting materials of formula (IV), (VI), (VIIA), (VIIB), (VIIC), (VIID), (VIIE) and (VIII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) comprising a N—BOC moiety may be converted into the corresponding compound comprising a N—H moiety by treatment with an acid, e.g. a mineral acid such as hydrochloric acid, or an organic acid such as trifluoroacetic acid.

A compound of formula (I) wherein $R^1$ represents —$SR^a$ may be converted into the corresponding compound wherein $R^1$ represents —$SO_2R^a$ by treatment with an oxidising agent, typically 3-chloroperoxybenzoic acid (MCPBA).

A compound of formula (I) wherein $R^1$ represents —$SO_2R^a$, e.g. methylsulfonyl, may be converted into the corresponding compound wherein $R^1$ represents —$OR^a$ by treatment with a sodium salt of formula $NaOR^a$. Similarly, a compound of formula (I) wherein $R^1$ represents —$SO_2R^a$, e.g. methylsulfonyl, may be converted into the corresponding compound wherein $R^1$ represents cyano by treatment with a cyanide salt, e.g. an alkali metal cyanide salt such as sodium cyanide. Likewise, a compound of formula (I) wherein $R^1$ represents —$SO_2R^a$, e.g. methylsulfonyl, may be converted into the corresponding compound wherein $R^1$ represents —$NR^bR^c$ by treatment with an amine of formula H—$NR^bR^c$.

A compound of formula (I) wherein $R^2$ represents halogen, e.g. bromo, may be converted into the corresponding compound wherein $R^2$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. tetrakis(triphenylphosphine)palladium(0), or [1,1'-bis(diphenylphosphino)ferrocene]dichloropalladium(II), and a base, e.g. an inorganic base such as sodium carbonate or potassium carbonate, or potassium phosphate.

A compound of formula (I) wherein $R^2$ represents —$CO_2R^d$, in which $R^d$ is other than hydrogen, may be converted into the corresponding compound wherein $R^2$ represents carboxy (—$CO_2H$) by treatment with a base, typically an alkali metal hydroxide such as sodium hydroxide. A compound of formula (I) wherein $R^2$ represents carboxy (—$CO_2H$) may be converted into the corresponding compound wherein $R^2$ represents —$CONR^bR^c$ or —$CON(OR^a)R^b$ by treatment with the appropriate reagent of formula H—$NR^bR^c$ or H—$N(OR^a)R^b$ respectively, typically in the presence of a coupling agent such as 1-(3-dimethylaminopropyl)-3-ethylcarbodiimide hydrochloride (EDC) and an additive such as 1-hydroxybenzotriazole hydrate (HOBT), optionally in the presence of a base, e.g. an organic base such as N,N-diisopropylethylamine.

A compound of formula (I) wherein $R^2$ represents carboxy (—$CO_2H$) may be converted into the corresponding compound wherein $R^2$ represents —$CONH_2$ by treatment with ammonium chloride, typically in the presence of a coupling agent such as EDC and an additive such as HOBT, suitably in the presence of a base, e.g. an organic base such as diisopropylamine or N,N-diisopropylethylamine. A compound of formula (I) wherein $R^2$ represents —$CONH_2$ may be converted into the corresponding compound wherein $R^2$ represents cyano (—CN) by treatment with phosphorus oxychloride. Alternatively, a compound of formula (I) wherein $R^2$ represents —$CONH_2$ may be converted into the corresponding compound wherein $R^2$ represents cyano in a two-step procedure which comprises: (i) treatment with cyanuric chloride; and (ii) treatment of the material thereby obtained with water.

A compound of formula (I) wherein $R^2$ represents carboxy (—$CO_2H$) may be converted into the corresponding compound wherein $R^2$ represents hydroxymethyl (—$CH_2OH$) in a two-step procedure which comprises: (i) treatment with ethyl chloroformate and triethylamine; and (ii) treatment of the material thereby obtained with a reducing agent, typically an alkali metal borohydride such as sodium borohydride.

A compound of formula (I) wherein $R^2$ represents carboxy (—$CO_2H$) may be converted into the corresponding compound wherein $R^2$ represents hydroxy in a two-step procedure which comprises: (i) treatment with diphenyl phosphoryl azide; and (ii) treatment of the material thereby obtained with water.

A compound of formula (I) wherein $R^2$ represents carboxy (—$CO_2H$) may be converted into the corresponding compound wherein $R^2$ represents —$NHCO_2R^d$, wherein $R^d$ is other than hydrogen, in a two-step procedure which comprises: (i) treatment with diphenyl phosphoryl azide; and (ii) treatment of the material thereby obtained with the appropriate reagent of formula $R^d$—OH.

A compound of formula (I) wherein $R^2$ represents carboxy (—$CO_2H$) may be converted into the corresponding compound wherein $R^2$ represents a 3-substituted 1,2,4-oxadiazol-5-yl moiety in a two-step procedure which comprises: (i) treatment with an appropriately-substituted N'-hydroxyamidine derivative, typically in the presence of a coupling agent such as O-(7-azabenzotriazol-1-yl)-N,N,N',N'-tetramethyluronium hexafluorophosphate (HATU), suitably in the presence of a base, e.g. an organic base such as N,N-diisopropylethylamine; and (ii) treatment of the material thereby obtained with a strong base, suitably a strong inorganic base, e.g. an alkali metal tert-butoxide such as potassium tert-butoxide.

A compound of formula (I) wherein $R^3$ represents hydrogen may be converted into the corresponding compound wherein $R^3$ represents $C_{1-6}$ alkyl, e.g. methyl, by treatment with a $C_{1-6}$ alkyl halide, e.g. iodomethane, usually in the presence of a base, suitably a strong inorganic base, e.g. sodium hydride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3rd edition, 1999. The protecting groups may be removed at any convenient subsequent stage utilising methods known from the art.

The following Examples illustrate the preparation of compounds according to the invention.

The compounds in accordance with this invention potently inhibit the activity of human PI4KIIIβ.

PI4KIIIβ Enzyme Inhibition Assay

Procedure A

Compounds were assayed utilizing reagents from Invitrogen and Promega. Compounds were screened in 1% DMSO (final) as 3-fold serial dilutions from a starting concentration of 20 μM. The 2.5× PI4Kβ reagent, the 2.5× PI Lipid Kinase Substrate/ATP mixture and the 5× compounds were prepared in 20 mM Tris pH 7.5, 0.5 mM EGTA, 2 mM DTT, 5 mM $MgCl_2$, 0.4% Triton. The final 25 μL Kinase Reaction consisted of: 4 nM PI4Kβ, 100 μM PI Lipid Kinase Substrate (both Invitrogen), and compound. The final ATP concentration in the assay was 10 μM. The detection reagents consisted of ADP-Glo™ Reagent and ADP-Glo™ Detect Reagent (Promega).

Briefly, compound was added to PI4Kβ followed by addition of ATP/PI Lipid Kinase Substrate mixture. The reaction mixture was incubated for 60 minutes at room temperature. The ADP-Glo™ Reagent was added and the plate was incubated for 40 minutes at room temperature, followed by addition of ADP-Glo™ Detect Reagent. The plate was incubated for a further 120 minutes and read on a Luminescence plate reader. The data was fitted with XLfit from IDBS using model number 205.

Procedure B

Compounds were assayed using a PI4Kbeta Adapta assay. Compounds were screened in 1% DMSO (final) as 3-fold serial dilutions from a starting concentration of 10 μM. The 2× PI4KB (PI4K beta)/PI Lipid Kinase Substrate mixture was prepared in 50 mM HEPES pH 7.5, 0.1% CHAPS, 1 mM EGTA, 4 mM $MgCl_2$. The final 10 μL Kinase Reaction consisted of 7.5-60 ng PI4Kβ, and 100 μM PI Lipid Kinase Substrate in 32.5 mM HEPES pH 7.5, 0.05% CHAPS, 0.5 mM EGTA, 2 mM $MgCl_2$. The final ATP concentration in the assay was 10 μM. The detection mix consisted of EDTA (30 mM), Eu-anti-ADP antibody (6 nM) and ADP tracer. The detection mix contained the EC60 concentration of tracer for 5-150 μM ATP.

Briefly, ATP was added to compound, followed by addition of a PI4Kβ/PI Lipid Kinase Substrate mixture. The plate was shaken for 30 seconds to mix, then briefly centrifuged. The reaction mixture was incubated for 60 minutes at room temperature. The detection mix was added, then the plate was shaken and centrifuged. The plate was incubated for 60 minutes at room temperature and read on a fluorescence plate reader. The data was fitted with XLfit from IDBS using model number 205.

When tested in the above assay (Procedure A or Procedure B), the compounds of the accompanying Examples were all found to possess $IC_{50}$ values for inhibition of the activity of human PI4KIIIβ of 50 μM or better.

Certain compounds in accordance with this invention are potent inhibitors when measured in the MLR test described below.

The Mixed Lymphocyte Reaction (MLR) Test

Human peripheral blood mononuclear cells (PBMCs) were isolated from buffy coats, obtained from healthy blood donors by Ficoll (Lymphoprep, Axis-Shield PoC AS, Oslo, Norway) density-gradient centrifugation. The cells at the Ficoll-plasma interface were washed three times and used as "Responder" cells. RPMI 1788 (ATCC, No. CCL-156) cells were treated with mitomycin C (Kyowa, Nycomed, Brussels, Belgium) and used as "Stimulator" cells. Responder cells (0.12×106), Stimulator cells (0.045×106) and compounds (in different concentrations) were cocultured for 6 days in RPMI 1640 medium (BioWhittaker, Lonza, Belgium) supplemented with 10% fetal calf serum, 100 U/ml Geneticin (Gibco, LifeTechnologies, UK). Cells were cultured in triplicate in flat-bottomed 96-well microtiter tissue culture plates (TTP, Switzerland). After 5 days, cells were pulsed with 1 μCi of methyl-$^3$H thymidine (MP Biomedicals, USA), harvested 18 h later on glass filter paper and counted. Proliferation values were expressed as counts per minute (cpm), and converted to % inhibition with respect to a blank MLR test (identical but without added compound). The $IC_{50}$ was determined from a graph with at least four points, each derived from the mean of 2 experiments. The $IC_{50}$ value represents the lowest concentration of test compound (expressed in μM) that resulted in a 50% inhibition of the MLR.

Certain compounds of the accompanying Examples were found to generate $IC_{50}$ values in the MLR test of 10 μM or better.

EXAMPLES

Abbreviations

| | |
|---|---|
| THF: tetrahydrofuran | MeOH: methanol |
| DMF: N,N-dimethylformamide | DMSO: dimethyl sulfoxide |
| DCM: dichloromethane | DIPEA: N,N-diisopropylethylamine |
| TFA: trifluoroacetic acid | EtOAc: ethyl acetate |
| MCPBA: 3-chloroperoxybenzoic acid | DMAP: 4-(dimethylamino)pyridine |
| IPA: isopropyl alcohol | IMS: industrial methylated spirit |
| HATU: O-(7-azabenzotriazol-1-yl)-N,N,N',N'-tetramethyluronium hexafluorophosphate | |
| Pd(dppf)$Cl_2$: [1,1'-bis(diphenylphosphino)ferrocene]dichloropalladium(II) | |
| h: hour | |
| MS: Mass Spectrometry | M: mass |
| RT: retention time | r.t.: room temperature |
| LCMS: Liquid Chromatography Mass Spectrometry | |
| HPLC: High Performance Liquid Chromatography | |

Analytical Methods

Method 1

High pH (approximately pH 9.5)

Column: Waters XBridge, C18, 2.1×20 mm, 2.5 μm

Solvent A: 10 mM ammonium formate in water+0.1% ammonia solution

Solvent B: acetonitrile+5% solvent A+0.1% ammonia solution

Gradient Program:

| Time | A % | B % |
|---|---|---|
| 0.00 | 95.0 | 5.0 |
| 1.50 | 5.0 | 95.0 |
| 2.50 | 5.0 | 95.0 |
| 3.00 | 95.0 | 5.0 |

Method 2

High pH (approximately pH 9.5)

Column: Waters XBridge, C18, 2.1×20 mm, 2.5 m

Solvent A: 10 mM ammonium formate in water+0.1% ammonia solution

Solvent B: acetonitrile+5% solvent A+0.1% ammonia solution

Gradient Program:

| Time | A % | B % |
|---|---|---|
| 0.00 | 95.0 | 5.0 |
| 4.00 | 5.0 | 95.0 |
| 5.00 | 5.0 | 95.0 |
| 5.10 | 95.0 | 5.0 |

Method 3

Low pH (approximately pH 3)

Column: Waters XBridge, C18, 2.1×20 mm, 2.5 m

Solvent A: 10 mM ammonium formate in water+0.1% formic acid solution

Solvent B: acetonitrile+5% solvent A+0.1% formic acid solution

Gradient Program:

| Time | A % | B % |
|---|---|---|
| 0.00 | 95.0 | 5.0 |
| 1.50 | 5.0 | 95.0 |
| 2.50 | 5.0 | 95.0 |
| 3.00 | 95.0 | 5.0 |

Method 4
Low pH (approximately pH 3)
Column: Waters XBridge, C18, 2.1×20 mm, 2.5 m
Solvent A: 10 mM ammonium formate in water+0.1% formic acid solution
Solvent B: acetonitrile+5% solvent A+0.1% formic acid solution
Gradient Program:

| Time | A % | B % |
|---|---|---|
| 0.00 | 95.0 | 5.0 |
| 4.00 | 5.0 | 95.0 |
| 5.00 | 5.0 | 95.0 |
| 5.10 | 95.0 | 5.0 |

Method 5
High pH (approximately pH 9.5)
Column: Waters XBridge, C18, 2.1×20 mm, 2.5 μm
Solvent A: 10 mM ammonium formate in water+0.1% ammonia solution
Solvent B: acetonitrile+5% solvent A+0.1% ammonia solution
Gradient Program:

| Time | A % | B % |
|---|---|---|
| 0.00 | 95.0 | 5.0 |
| 3.00 | 5.0 | 95.0 |
| 4.00 | 5.0 | 95.0 |
| 5.00 | 95.0 | 5.0 |

Method 6
Waters Acquity-SQD
Solvent A: 10 mM ammonium formate+0.1% ammonia
Solvent B: 95% acetonitrile+5% water+0.1% ammonia
Gradient Program:

| Time | A % | B % |
|---|---|---|
| 0.00 | 95.0 | 5.0 |
| 0.50 | 95.0 | 5.0 |
| 1.75 | 5.0 | 95.0 |
| 2.00 | 5.0 | 95.0 |
| 2.25 | 95.0 | 5.0 |

Intermediate 1

6-Amino-4-chloro-1H-pyrazolo[3,4-d]pyrimidine

To a suspension of 2-amino-4,6-dichloropyrimidine-5-carbaldehyde (1.92 g, 10 mmol) and triethylamine (1.59 mL, 11.5 mmol) in a mixture of THF (40 mL) and $H_2O$ (4 mL) was added hydrazine (64%, 486 μL, 10 mmol) dropwise at r.t. The reaction mixture was continuously stirred for 4 h, then the volatile material was removed under vacuum. The residue was precipitated with $H_2O$. The precipitate was washed with $H_2O$, and dried under vacuum to provide the title compound (1.8 g, quantitative) as a yellow solid. $^{13}C$ NMR δ (DMSO-$d_6$, 75 MHz) 161.5 (C-2), 157.5 (C-4), 153.2 (C-7a), 132.7 (C-5), 105.8 (C-4a). MS (m/z) 170 $[M+H]^+$.

Intermediate 2

6-Amino-4-(piperazin-1-yl)-1H-pyrazolo[3,4-d]pyrimidine

To a suspension of Intermediate 1 (169 mg, 1 mmol) and piperazine (86 mg, 1 mmol) in DMF (4 mL) was added DIPEA (345 μL, 2 mmol) at r.t., and the reaction mixture was continuously stirred overnight. The volatile material was evaporated under reduced pressure, and the residue was precipitated in cold DCM, to provide the title compound (240 mg, quantitative) as a yellow solid. $^{13}C$ NMR δ (DMSO-$d_6$, 75 MHz) 161.4 (C-2), 158.7 (C-4), 156.9 (C-7a), 133.4 (C-5), 94.3 (C-4a), 42.6 ($NCH_2$), 42.8 ($NCH_2$). MS (m/z) 220 $[M+H]^+$.

Intermediate 3

6-Amino-4-[2-(S)-methyl-4-(tert-butoxycarbonyl) piperazin-1-yl]-1H-pyrazolo[3,4-d]-pyrimidine To a suspension of Intermediate 1 (804 mg, 4.74 mmol) and 2-(S)-methyl-4-(tertbutoxycabonyl)piperazine (949 mg, 4.74 mmol) in DMF (10 mL) was added DIPEA (1.2 mL, 7.11 mmol) at r.t., and the reaction mixture was heated at 100° C. for 36 h. The volatile material was evaporated under reduced pressure, and the residue was precipitated in water, to provide the title compound (1.2 g, 76%) as a yellow solid. $\delta_H$ (DMSO-$d_6$, 300 MHz) 1.16 (d, J 6 Hz, 3H), 1.43 (s, 9H), 3.01-3.22 (m, 3H), 3.79-3.94 (m, 2H), 4.39-4.77 (m, 2H), 6.03 (s, 2H), 7.91 (s, 1H), 12.58 (s, 1H). MS (m/z) 334 $[M+H]^+$.

Intermediate 4 (Method A)

6-Amino-4-[2-(S)-methylpiperazin-1-yl]-1H-pyrazolo[3,4-d]pyrimidine

A solution of Intermediate 3 (193 mg, 0.58 mmol) in a mixture of DCM (3 mL) and trifluoroacetic acid (3 mL) was stirred at r.t. for 1 h. The reaction mixture was evaporated in vacuo and co-evaporated with $NH_3$-MeOH solution to dryness. The title compound was obtained as a crude product that was utilised in subsequent reactions without further purification. MS (m/z) 234 $[M+H]^+$.

Intermediate 5

2-Amino-6-chloro-4-[2-(S)-methyl-4-(tert-butoxycarbonyl)piperazin-1-yl]pyrimidine-5-carbaldehyde To a suspension of 2-amino-4,6-dichloropyrimidine-5-carbaldehyde (1.92 g, 10 mmol) and DIPEA (3.4 mL, 20 mmol) in DMF (30 mL) was added 2-(S)-methyl-4-(tertbutoxycabonyl)piperazine (2 g, 10 mmol), and the reaction mixture was stirred at r.t. for 24 h. The volatile material was evaporated, and the residue was precipitated in water, to provide the title compound (3.37 g, 94%) as a yellow solid. $^{13}C$ NMR δ (DMSO-$d_6$, 75 MHz) 183.5 (CHO), 166.6

(C-6), 162.9 (C-4), 161.2 (C-2), 154.3 (C=O), 103.7 (C-5), 78.9 (OC), 50.6 (NCH), 43.4 (NCH), 27.9 (Me), 14.8 (Me). MS (m/z) 356 $[M+H]^+$.

Intermediate 6

6-Amino-4-[2-(S)-methyl-4-(tert-butoxycarbonyl) piperazin-1-yl]-1-methylpyrazolo[3,4-d]pyrimidine To a solution of Intermediate 3 (662 mg, 1.98 mmol) in dry DMF (10 mL) was added NaH (96 mg, 2.38 mmol) at 0° C. The resulting solution was stirred at 0° C. for 15 minutes, then iodomethane (149 μL, 2.38 mmol) was added. The reaction mixture was slowly warmed to room temperature and continuously stirred for 3.5 h. The reaction mixture was concentrated and purified by silica gel chromatography (DCM:MeOH 50:1) to provide the title compound (492 mg, 47%) as a white solid. $^{13}C$ NMR δ (DMSO-$d_6$, 75 MHz) 161.1 (C-2), 157.6 (C-4), 156.9 (C-7a), 155.1 (C=O), 132.5 (C-5), 96.1 (C-4a), 80.2 ($OC(CH_3)_3$), 48.6 ($NCH_2$), 39.6 ($NCH_2$), 33.5 (NMe), 28.4 (Me), 15.3 (Me). MS (m/z) 348 $[M+H]^+$.

Alternative Preparation

To a solution of Intermediate 5 (356 mg, 1 mmol) and triethylamine (166 μL, 1.2 mmol) in THF (6 mL) at 0° C. was added methylhydrazine (108 μL, 2 mmol). The reaction mixture was slowly warmed to r.t. and continuously stirred for 42 h. The volatile material was evaporated, and the residue was purified by silica gel chromatography (DCM: MeOH 50:1), to provide the title compound (240 mg, 69%) as a white solid.

Intermediate 7

6-Amino-4-[2-(S)-methylpiperazin-1-yl]-1-methylpyrazolo[3,4-d]pyrimidine

Prepared via Method A using Intermediate 6 (87 mg, 0.25 mmol), TFA (3 mL) and DCM (3 mL). The title compound was obtained as a crude product that was utilised in subsequent reactions without further purification. MS (m/z) 248 $[M+H]^+$.

Alternative Preparation

Intermediate 6 (6.5 g, 19 mmol) in 4N HCl in 1,4-dioxane (20 mL) was stirred overnight. The reaction mixture was concentrated in vacuo, then triturated with diethyl ether, to yield the title compound dihydrochloride (5.2 g, 98%) as a yellow solid. LCMS (ES+) $[M+H]^+$ 248, RT 1.40 minutes (method 2).

Intermediate 8

1-(2-Amino-4,6-dichloropyrimidin-5-yl)ethanol

To 2-amino-4,6-dichloropyrimidine-5-carbaldehyde (0.93 g, 4.65 mmol) was added THF (34 mL) and the mixture was cooled to −78° C. under nitrogen. To the mixture was slowly added methylmagnesium chloride (4.8 mL of a 3.0M solution in THF). A further aliquot of methylmagnesium chloride (2.4 mL) was added slowly and the mixture was stirred at −78° C. for 30 minutes before being quenched with water (20 mL). A partial solid formed. The mixture was neutralised and diluted with water, then extracted with EtOAc (100 mL). The solid was discarded, and the aqueous layer was further extracted (10% MeOH/DCM, 3×100 mL). The organic layers were combined and dried over sodium sulfate. Concentration in vacuo gave the title compound (0.45 g, 46.8%) as a pale yellow solid, which was used crude without further purification. $\delta_H$ (DMSO-$d_6$, 300 MHz) 8.49 (br s, 1H), 7.38 (br s, 2H), 5.21-5.11 (m, 2H), 1.42 (d, J 6.9 Hz, 3H).

Intermediate 9

1-(2-Amino-4,6-dichloropyrimidin-5-yl)ethanone

To Intermediate 8 (0.45 g, 2.18 mmol) were added manganese dioxide (1.90 g, 21.9 mmol) and DCM (50 mL). The mixture was heated at 40° C. for 2.5 h before cooling to r.t. overnight. To the mixture was added further manganese dioxide (2.9 g, 34.2 mmol) and the mixture was heated at 40° C. for 3 h. The mixture was cooled to r.t. and filtered through celite. The solvent was removed in vacuo to yield the title compound (0.29 g, 65.3%) as a pale yellow solid. $\delta_H$ (DMSO-$d_6$) 7.90 (br s, 2H), 3.34 (s, 3H).

Intermediate 10 tert-Butyl (3S)-4-(5-acetyl-2-amino-6-chloropyrimidin-4-yl)-3-methylpiperazine-1-carboxylate To Intermediate 9 (0.29 g, 1.42 mmol) was added 2-(S)-methyl-4-(tert-butoxycarbonyl)piperazine (0.33 g, 1.6 mmol) and the solids were dissolved in 1,4-dioxane (10 mL). To this was added DIPEA (0.3 mL, 2 mmol) and the mixture was heated at 80° C. for 5 h before cooling to r.t. overnight. The solvent was removed in vacuo and the yellow oil was purified by flash column chromatography on silica [Biotage SNAP 25 g, Isolera, gradient elution (100% isohexane to 50% EtOAc/isohexane)] to yield the title compound (0.47 g, 89.9%) as a white foam. LCMS (ES+) 370.2 $[M+H]^+$, RT 1.35 minutes (method 3).

Intermediate 11 tert-Butyl (3S)-4-(6-amino-1,3-dimethylpyrazolo[3,4-d]pyrimidin-4-yl)-3-methyl-piperazine-1-carboxylate To Intermediate 10 (0.46 g, 1.25 mmol) in THF (15 mL) were added methylhydrazine (0.08 mL, 2 mmol) and triethylamine (0.35 mL, 2.5 mmol). The mixture was heated at 68° C. overnight whilst stirring under nitrogen. The mixture was concentrated in vacuo. The resulting off-white solid was purified by flash column chromatography on silica [Biotage SNAP 25 g, Isolera, gradient elution (20% EtOAc/isohexane to 100% EtOAc)], yielding the title compound as a white solid. LCMS (ES+) 362.2 $[M+H]^+$, RT 1.21 minutes (method 3).

Intermediate 12

1,3-Dimethyl-4-[(2S)-2-methylpiperazin-1-yl]pyrazolo[3,4-d]pyrimidin-6-amine hydrochloride To Intermediate 11 (0.31 g, 0.86 mmol) was added 4N HCl in 1,4-dioxane (10 mL) and the mixture was stirred at r.t. DCM (10 mL) was added to aid solubility. The mixture was stirred at r.t. for 6 h before concentration in vacuo, to yield the title compound (0.29 g, 90.51%) as an off white solid. LCMS (ES+) 262.2 $[M+H]^+$, RT 1.04 minutes (method 1).

Intermediate 13

4-Chloro-1-methylpyrazolo[3,4-d]pyrimidin-6-amine

To a suspension of 2-amino-4,6-dichloropyrimidine-5-carbaldehyde (5.35 g, 26.75 mmol) in THF (60 mL) was added triethylamine (11.5 mL, 82.5 mmol) and the mixture was cooled to 5° C. (ice bath). Methylhydrazine (1.4 mL, 27 mmol) was added, and the mixture was stirred at 5° C. for 1 h, before warming to r.t. The bright yellow mixture was stirred at r.t. for a further 30 minutes before filtering under reduced pressure. The resulting solid was washed with diethyl ether followed by water, then dried, to yield the title compound (4.06 g, 82.6%) as a yellow solid. $\delta_H$ (DMSO-$d_6$) 7.97 (s, 1H), 7.29 (s, 2H), 3.79 (s, 3H).

Intermediate 14 tert-Butyl (3R)-4-(6-amino-1-methylpyrazolo[3,4-d]pyrimidin-4-yl)-3-(hydroxymethyl)-piperazine-1-carboxylate To Intermediate 13 (3.99 g, 21.7 mmol) was added tert-butyl (3R)-3-(hydroxymethyl)piperazine-1-carboxylate (5.21 g, 24 mmol), and the mixture was suspended in 1,4-dioxane (100 mL). To this was added DIPEA (4.6 mL, 26 mmol) and the mixture was heated at 80° C. for 1 h. Further DIPEA (9 mL) was added and the mixture was heated at 100° C. for 48 h. The reaction mixture was cooled to r.t. and concentrated in vacuo, to yield an orange solid which was triturated with water/ether/dichloromethane and filtered. The solid was discarded, and the filtrate was concentrated in vacuo. The resulting orange oil was purified by flash column chromatography on silica [Biotage SNAP 200 g, Isolera, gradient elution (80% EtOAc/isohexanes to 100% EtOAc; followed by 100% DCM to 20% MeOH/DCM)], to yield the title compound (4.51 g, 57.1%) as a yellow oil. LCMS (ES+) 364.8 $[M+H]^+$, RT 1.20 minutes (method 3).

Intermediate 15

[(2R)-1-(6-Amino-1-methylpyrazolo[3,4-d]pyrimidin-4-yl)piperazin-2-yl]methanol hydrochloride Intermediate 14 (0.5 g, 1.38 mmol) was stirred for 3 days with 4N HCl in 1,4-dioxane (10 mL). The reaction mixture was concentrated in vacuo and slurried in diethyl ether. Further concentration in vacuo gave the title compound (0.41 g, 99.0%) as a pale yellow powder. LCMS (ES+) 264.8 $[M+H]^+$, RT 0.65 minutes (method 1).

Intermediate 16 tert-Butyl (3S)-4-[2-amino-6-chloro-5-(2,2,2-trifluoro-1-hydroxyethyl)pyrimidin-4-yl]-3-methylpiperazine-1-carboxylate To Intermediate 5 (1.51 g, 4.25 mmol) were added CsF (0.067 g, 0.44 mmol) and THF (40 mL). The mixture was stirred at r.t. under nitrogen for 2 minutes prior to the dropwise addition of (trifluoromethyl)trimethylsilane (3.8 mL, 25 mmol). The mixture was stirred at r.t. for 4 h, then the reaction was quenched with 0.5M hydrochloric acid (30 mL) and the mixture was stirred for 10 minutes. The mixture was partitioned between water (50 mL) and EtOAc (50 mL). The organic phase washed with water (50 mL) and brine (50 mL), then dried over sodium sulfate. The solvent was removed in vacuo. The resulting orange oil was purified by flash column chromatography on silica [Biotage SNAP 50 g, Isolera, gradient elution (10% EtOAc/isohexane to 40% EtOAc/isohexane)], to yield the title compound (0.75 g, 49.4%) as a yellow foam. LCMS (ES+) 426.2 $[M+H]^+$, RT 1.32 minutes (method 1).

Intermediate 17 tert-Butyl (3S)-4-[2-amino-6-chloro-5-(2,2,2-trifluoroacetyl)pyrimidin-4-yl]-3-methyl-piperazine-1-carboxylate To Intermediate 16 (0.47 g, 1.13 mmol) were added manganese dioxide (1.03 g, 11.9 mmol) and DCM (25 mL) and the mixture was stirred under nitrogen at r.t. overnight. Further manganese dioxide (1.57 g, 18 mmol) was added and the mixture was heated at 40° C. for 3 h before cooling to r.t. the mixture was filtered through Celite, washing with further DCM. The solvent was removed in vacuo, to yield the title compound (0.39 g, 82.3%). LCMS (ES+) 424.2 $[M+H]^+$, RT 2.95 minutes (method 1).

Intermediate 18 tert-Butyl (3S)-4-[6-amino-1-methyl-3-(trifluoromethyl)pyrazolo[3,4-d]pyrimidin-4-yl]-3-methylpiperazine-1-carboxylate To Intermediate 17 (0.39 g, 0.93 mmol) dissolved in THF (15 mL) were added methylhydrazine (0.06 mL, 1 mmol) and triethylamine (0.26 mL, 1.9 mmol). The mixture was heated at 68° C. under nitrogen for 48 h. The mixture was cooled to r.t. and concentrated in vacuo. The resulting yellow solid was purified by flash column chromatography on silica [Biotage SNAP 25 g, Isolera, gradient elution (20% EtOAc/isohexane to 100% EtOAc)], to yield the title compound (0.15 g, 38.8%) as an off-white solid. LCMS (ES+) 416.2 $[M+H]^+$, RT 2.60 minutes (method 1).

Intermediate 19

1-Methyl-4-[(2S)-2-methylpiperazin-1-yl]-3-(trifluoromethyl)pyrazolo[3,4-d]pyrimidin-6-amine hydrochloride To Intermediate 18 (0.15 g, 0.36 mmol) dissolved in DCM (10 mL) was added 4N HCl in 1,4-dioxane (10 mL) and the reaction mixture was stirred at r.t. for 1 h. A cloudy white precipitate formed and the mixture was diluted with methanol. The solvent was removed in vacuo to yield the title compound (0.15 g, 99.31%) as an off-white gum.

LCMS (ES+) 316.2 $[M+H]^+$, RT 1.77 minutes (method 1).

Intermediate 20 tert-Butyl (3R)-4-(2-amino-6-chloro-5-formylpyrimidin-4-yl)-3-methylpiperazine-1-carboxylate 2-Amino-4,6-dichloropyrimidine-5-carboxaldehyde (17.1 mmol), tert-butyl (3R)-3-methylpiperazine-1-carboxylate (3.43 g, 17.1 mmol) and DIPEA (2.66 g, 20.6 mmol)

were heated in 1,4-dioxane (200 mL) at 60° C. After 4 h, the reaction mixture was cooled and stirred at r.t. overnight. The reaction mixture was re-heated for a further 4 h at 80° C., then stirred at r.t. overnight. The reaction mixture was then concentrated in vacuo, and partitioned between diethyl ether and water. A fine orange solid was filtered off and discarded. The ether washings were dried over sodium sulfate and concentrated in vacuo, to give the title compound (4 g, 65.6%) as a yellow foam. LCMS (ES+) 356.2 $[M+H]^+$, RT 2.26 minutes (method 1).

Intermediate 21 tert-Butyl (3R)-4-(6-amino-1-methylpyrazolo[3,4-d]pyrimidin-4-yl)-3-methylpiperazine-1-carboxylate Intermediate 20 (4 g, 11.24 mmol) in THF (100 mL) was treated with triethylamine (2.28 g, 22.48 mmol) and methylhydrazine (12.37 mmol). The reaction mixture was stirred at 60° C. for 1 h, then cooled and left overnight. The reaction mixture was concentrated in vacuo, and the residue was partitioned between DCM and water. The organic phases were separated and concentrated in vacuo, to give the title compound (3.9 g, 100%) as a yellow foam. LCMS (ES+) 348.2 $[M+H]^+$, RT 1.36 minutes (method 1).

Intermediate 22

1-Methyl-4-[(2R)-2-methylpiperazin-1-yl]pyrazolo[3,4-d]pyrimidin-6-amine hydrochloride Intermediate 21 (4.5 g, 13 mmol) was dissolved in 4N HCl in 1,4-dioxane (20 mL) and stirred for 1 h. MeOH (5 mL) was added to aid solubility. The reaction mixture was stirred for 1 h, then concentrated in vacuo. The residue was triturated from diethyl ether to give the title compound (3.5 g, 95%) as a pale yellow powder. LCMS (ES+) 248.3 $[M+H]^+$, RT 0.45 minutes (method 1).

Intermediate 23

Phenyl N-[6-(3,3-difluoroazetidin-1-yl)-2-methylpyridin-3-yl]carbamate

To a solution of 6-(3,3-difluoroazetidin-1-yl)-2-methylpyridin-3-amine (WO 2010/139747; 7.2 g, 36 mmol) in THF (100 mL) at 0° C. (ice bath) were added pyridine (3.6 g, 45 mmol) then phenyl chloroformate (38 mmol) dropwise. The reaction mixture was stirred for 3 h, then left at r.t. overnight. Another aliquot of phenyl chloroformate (1 mL) and pyridine (1 mL) was added, and the reaction mixture was stirred at r.t. for 4 h. The reaction mixture was concentrated in vacuo, and the residue was partitioned between EtOAc and 2% HCl solution. The organic layers were dried over sodium sulfate and concentrated in vacuo, to yield an off-white waxy solid. The aqueous acidic layer was neutralised with saturated aqueous sodium bicarbonate solution, and a solid was collected by filtration. The batches of recovered material were combined to give the title compound (9.92 g, 86.0%). LCMS (ES+) 320.2 $[M+H]^+$, RT 1.34 minutes.

Intermediate 24

Phenyl N-(6-methoxy-2-methylpyridin-3-yl)carbamate

To a solution of 6-methoxy-2-methylpyridin-3-amine (2.02 g, 13.9 mmol) in DCM (50 mL) were added triethylamine (2.3 mL, 17 mmol) and phenyl chloroformate (1.9 mL, 15 mmol) and the mixture was stirred under nitrogen at r.t. overnight. The mixture was washed with saturated aqueous sodium bicarbonate solution. The organic layer was separated, and concentrated in vacuo. To the resulting brown oil was added diethyl ether. Following the addition of isohexane, a solid precipitated out of solution, to yield the title compound (2.79 g, 56.0%) as an off-white/pale pink solid. LCMS (ES+) 259.8 $[M+H]^+$, RT 1.77 minutes.

Intermediate 25

Phenyl N-(4-methoxy-2-methylphenyl)carbamate

To a solution of 4-methoxy-2-methylaniline (5 g, 36.45 mmol) in THF (100 mL) at 0° C. (ice bath) were added pyridine (45.56 mmol) then phenyl chloroformate (38.27 mmol). The reaction mixture was allowed to warm to r.t. and stirred overnight. The reaction mixture was then partitioned between 5% HCl solution and EtOAc. The organic layers were washed further with 5% HCl solution, then saturated aqueous sodium bicarbonate solution. The organic layers were dried over sodium sulfate and concentrated in vacuo, to yield the title compound (7.61 g, 81.1%) as a pale purple powder. $\delta_H$ (DMSO-$d_6$) 9.30 (s, 1H), 7.40 (t, J 7.7 Hz, 2H), 7.30-7.09 (m, 3H), 6.90-6.62 (m, 3H), 3.72 (s, 3H), 2.25 (s, 3H).

Intermediate 26

2-(3,3-Difluoroazetidin-1-yl)-4-methyl-5-nitropyridine

To a solution of 2-chloro-4-methyl-5-nitropyridine (1 g, 5.7 mmol) in DMF (10 mL) were added $Cs_2CO_3$ (3.7 g, 11.4 mmol) followed by 3,3-difluoroazetidine (1.4 g, 11.4 mmol), and the reaction mixture was heated for 3 h at 80° C. The reaction mixture was then diluted with EtOAc. The organic layer was washed with saturated aqueous sodium bicarbonate solution, then dried over sodium sulfate and concentrated in vacuo. The resulting crude material was purified by flash column chromatography on silica (100-200 mesh, 2-3% MeOH/DCM), to afford the title compound (1.1 g, 83.0%) as a light brown solid. $\delta_H$ (DMSO-$d_6$) 8.85 (s, 1H), 6.58 (s, 1H), 4.59 (t, 4H), 2.53 (s, 3H).

Intermediate 27

6-(3,3-Difluoroazetidin-1-yl)-4-methylpyridin-3-amine

To a stirred solution of Intermediate 26 (0.28 mmol) in MeOH (10 mL) was added Pd/C (50 mg). The reaction mixture was stirred under a hydrogen atmosphere for 4 h at r.t. The reaction mixture was then filtered through Celite. The organic layer was concentrated, to afford the title compound (0.26 g, 59.0%) as an off-white solid. $\delta_H$ (DMSO-$d_6$) 7.60 (s, 1H), 6.30 (s, 1H), 4.30 (br s, 2H), 4.20 (t, 4H), 2.05 (s, 3H).

Intermediate 28 tert-Butyl N-(2-chloro-4-methylpyrimidin-5-yl)carbamate

To a solution of 2-chloro-4-methylpyrimidin-5-amine (WO 2009/112524; 0.8 g, 5.59 mmol) and triethylamine (2.6 mL, 19.58 mmol) in DCM (10 mL) was added di-tert-butyl dicarbonate (22.0 mmol). The reaction mixture was stirred for 18 h at r.t. The reaction mixture was then diluted with DCM. The organic layer was washed with saturated aqueous sodium bicarbonate solution, then dried over sodium sulfate and concentrated in vacuo. The resulting crude material was purified by flash column chromatography on silica (100-200 mesh, 40% EtOAc/isohexanes), to afford the title compound (0.7 g, 51.0%) as a semi-solid. LCMS (ES+) 244.05 $[M+H]^+$, RT 2.15 minutes (method 5).

Intermediate 29

$N^2$,$N^2$,4-Trimethylpyrimidine-2,5-diamine hydrochloride

To a solution of Intermediate 28 (0.2 g, 0.8 mmol) in MeOH (2 mL) was added dimethylamine in water (0.5 mL). The reaction mixture was heated at 60° C. for 3 h. The reaction mixture was diluted with EtOAc, then the organic layer was washed with water and brine, dried over sodium sulphate, and concentrated in vacuo. The resulting crude material was purified by flash column chromatography on silica (100-200 mesh, 2-5% MeOH/DCM). The resulting white solid was taken up in 1,4-dioxane (1 mL), treated with 4N HCl in 1,4-dioxane (2 mL) and stirred at r.t. for 3 h. The reaction mixture was concentrated, then the resulting crude material was triturated with diethyl ether, to afford the title compound (0.1 g, 83.0%). LCMS (ES+) 153.00 $[M+H]^+$, RT 0.95 minutes (method 5).

Intermediate 30

2-(3,3-Difluoroazetidin-1-yl)-4-methylpyrimidin-5-amine hydrochloride

To a solution of Intermediate 28 (0.3 g, 1.23 mmol) in DMF (5 mL) were added $Cs_2CO_3$ (0.8 g, 2.4 mmol) and 3,3-difluoroazetidine (0.3 g, 2.4 mmol) and the reaction mixture was heated at 80° C. for 3 h. The reaction mixture was diluted with EtOAc, then the organic layer was washed with saturated aqueous sodium bicarbonate solution, dried over sodium sulfate and concentrated in vacuo. The resulting crude material was purified by flash column chromatography on silica (100-200 mesh, 30% EtOAc/isohexanes). The resulting off-white solid was taken up in 1,4-dioxane (1 mL), treated with 4N HCl in 1,4-dioxane (2 mL) and stirred at r.t. for 3 h. The reaction mixture was concentrated, then the resulting crude material was triturated with diethyl ether, to afford the title compound (0.12 g, 82.0%). LCMS (ES+) 201.05 $[M+H]^+$, RT 0.96-1.21 minutes (method 5).

Intermediate 31

1-Methyl-6-sulfanyl-5H-pyrazolo[3,4-d]pyrimidin-4-one

To a solution of ethyl 5-amino-1-methyl-1H-pyrazole-4-carboxylate (2.0 g, 11.8 mmol) in acetone (30 mL) at r.t. was added benzoyl isothiocyanate (1.7 mL, 12.6 mmol). The reaction mixture was continuously stirred for 8 h, then concentrated in vacuo. The residue was dissolved in acetone (120 mL), MeOH (120 mL) and water (15 mL), and potassium carbonate (3.27 g, 23.6 mmol) was added. The mixture was heated under reflux with stirring for 4 h. The solution was allowed to cool down to r.t. and glacial acetic acid was added until all potassium carbonate was dissolved. The solution was cooled to 0° C. and the precipitate was collected, to yield the title compound (1.68 g) as a white solid. $^{13}C$ NMR δ (DMSO-$d_6$, 75 MHz) 175.0, 156.2, 144.1, 135.5, 102.0, 35.9. MS (m/z) 183 $[M+H]^+$.

Intermediate 32

1-Methyl-6-(methylsulfanyl)-5H-pyrazolo[3,4-d]pyrimidin-4-one

To a solution of Intermediate 31 (1.779 g, 9.76 mmol) in THF (90 mL) were added triethylamine (1.630 mL, 11.7 mmol) and iodomethane (0.638 mL, 10.2 mmol). The reaction mixture was continuously stirred for 1 h, then partitioned between EtOAc and saturated aqueous sodium bicarbonate solution. The organic layer was dried over magnesium sulfate and evaporated in vacuo, affording the title compound (1.79 g) as a white solid. $^{13}C$ NMR δ (DMSO-$d_6$, 75 MHz) 160.6, 157.9, 151.9, 134.2, 102.8, 33.9, 13.0. MS (m/z) 197 $[M+H]^+$.

Intermediate 33 tert-Butyl (3S)-3-methyl-4-[1-methyl-6-(methylsulfanyl)pyrazolo[3,4-d]pyrimidin-4-yl]piperazine-1-carboxylate To Intermediate 32 (1.449 g, 7.4 mmol) were added $POCl_3$ (15 mL) and N,N-dimethylaniline (0.5 mL) at r.t. The suspension was continuously stirred for 2 h at 105° C., by which time the suspension had become a solution. The reaction mixture was evaporated, then the residue was extracted using EtOAc and brine. The organic solvent was dried over magnesium sulfate and evaporated in vacuo. The residue was dissolved in 1,4-dioxane (70 mL), then DIPEA (2.634 mL, 15.9 mmol) and (S)-tert-butyl 3-methylpiperazine-1-carboxylate (1.595 g, 7.9 mmol) were added. The reaction mixture was continuously stirred for 4 h at 105° C. The solution was evaporated in vacuo, then the residue was purified by silica gel chromatography (10% EtOAc/cyclohexane), to provide the title compound (1.733 g) as a yellow solid. $^{13}C$ NMR δ (DMSO-$d_6$, 75 MHz) 167.5, 155.5, 154.6, 133.1, 128.6, 111.1, 79.2 (3C), 48.6, 47.6, 42.9, 42.4, 33.5, 15.1, 13.7. MS (m/z) 379 $[M+H]^+$.

Intermediate 34

1-Methyl-4-[(2S)-2-methylpiperazin-1-yl]-6-(methylsulfanyl)pyrazolo[3, 4-d]pyrimidine trifluoroacetate Prepared via Method A by treating Intermediate 33 (50 mg, 0.13 mmol) with DCM (1 mL) and TFA (1 mL). The title compound was obtained as a crude product that was utilised in subsequent reactions without further purification. MS (m/z) 279 $[M+H]^+$.

Intermediate 35 tert-Butyl (3S)-4-(2-amino-6-chloro-5-formylpyrimidin-4-yl)-3-ethylpiperazine-1-carboxylate To a solution of tert-butyl (3S)-3-ethylpiperazine-1-carboxylate (0.5 g, 2.3 mmol) and 2-amino-4,6-dichloropyrimidine-5-carbaldehyde (0.45 g) in 1,4-dioxane (8.0 mL) was added DIPEA (1.2 mL, 7.0 mmol). The reaction mixture was heated at 120° C. overnight in a sealed Wheaton vial, then cooled and stirred at room temperature over the weekend. The solvent was removed in vacuo, and the residue was partitioned between water and DCM. The organic layers were phase separated and concentrated in vacuo to give the title compound (0.85 g, 99%) as a yellow glass. LCMS (ES+) $[M+H]^+$ 370, RT 1.81 minutes (method 2).

Intermediate 36 tert-Butyl (3S)-4-(6-amino-1-methylpyrazolo[3,4-d]pyrimidin-4-yl)-3-ethylpiperazine-1-carboxylate To a solution of Intermediate 35 (1.0 g) in THF (10 mL) were added triethylamine (0.55 g, 0.75 mL) and methylhydrazine (0.14 g, 0.16 mL). The reaction mixture was stirred for 5 h at room temperature, then concentrated in vacuo and partitioned between DCM and water. The organic layers were phase separated and concentrated in vacuo to yield the title compound (0.9 g, 90%) as a pale cream foam. LCMS (ES+) $[M+H]^+$ 362.4, RT 1.50 minutes (method 2).

Intermediate 37

4-[(2S)-2-Ethylpiperazin-1-yl]-1-methylpyrazolo[3,4-d]pyrimidin-6-amine dihydrochloride Intermediate 36 (0.9 g, 2 mmol) was stirred in HCl (4N in 1,4-dioxane, 10 mL) for 2 h, then concentrated in vacuo, to give the title compound (0.8 g, quantitative) as a white powder. LCMS (ES+) $[M+H]^+$ 262, RT 0.57 minutes (method 2).

INTERMEDIATES 38 TO 66

To a cooled (ice bath) solution of the specified amine (1 mmol) in THF (50 mL) was added pyridine (1.1 equiv.), followed by phenyl chloroformate (1 equiv.) dropwise. The reaction mixture was allowed to warm to room temperature. When LCMS confirmed complete conversion of the amine to the desired carbamate, the reaction mixture was quenched with water. The desired carbamate was then either collected by filtration, or extracted into DCM, phase separated and concentrated in vacuo, then used without further purification. The indicated carbamates were prepared.

| | | | LCMS Data | | |
|---|---|---|---|---|---|
| Int. | Amine | Carbamate | Method | RT | $[M + H]^+$ |
| 38 | 2-Methyl-4-(trifluoromethoxy)aniline | Phenyl N-[2-methyl-4-(trifluoromethoxy)phenyl]carbamate | 2 | 2.26 | 312.2 |
| 39 | 2-Fluoro-4-(trifluoromethoxy)aniline | Phenyl N-[2-fluoro-4-(trifluoromethoxy)phenyl]carbamate | 1 | 1.56 | 316 |
| 40 | 2-Chloro-4-(trifluoromethoxy)aniline | Phenyl N-[2-chloro-4-(trifluoromethoxy)phenyl]carbamate | 1 | 1.59 | 332 |
| 41 | 3-Methoxy-5-(trifluoromethyl)aniline | Phenyl N-[3-methoxy-5-(trifluoromethyl)phenyl]carbamate | 2 | 2.64 | 312.2 |
| 42 | 1-Ethylindazol-3-amine | Phenyl N-(1-ethylindazol-3-yl)-carbamate | 1 | 1.39 | 282.0 |
| 43 | 6-(Difluoromethoxy)-2-methylpyridin-3-amine | Phenyl N-[6-(difluoromethoxy)-2-methylpyridin-3-yl]carbamate | 1 | 0.98 | 295.2 |
| 44 | 6-Ethoxy-5-fluoropyridin-3-amine | Phenyl N-(6-ethoxy-5-fluoropyridin-3-yl)carbamate | 1 | 1.41 | 277 |
| 45 | 2-Chloro-4-fluoro-5-methylaniline | Phenyl N-(2-chloro-4-fluoro-5-methylphenyl)carbamate | 2 | 2.36 | 280 |
| 46 | 5-Fluoro-6-methoxypyridin-3-amine | Phenyl N-(5-fluoro-6-methoxypyridin-3-yl)carbamate | 1 | 1.39 | 263 |
| 47 | 6-Ethoxy-2-methylpyridin-3-amine | Phenyl N-(6-ethoxy-2-methylpyridin-3-yl)carbamate | 1 | 1.45 | 273 |
| 48 | 1-Methyl-5-(trifluoromethyl)indazol-3-amine | Phenyl N-[1-methyl-5-(trifluoromethyl)indazol-3-yl]carbamate | 1 | 1.50 | 336 |
| 49 | 3-Amino-6-fluoro-1-methylindazole | Phenyl N-(6-fluoro-l-methylindazol-3-yl)carbamate | 1 | 1.36 | 286 |
| 50 | 5-Fluoro-1-methylindazol-3-amine | Phenyl N-(5-fluoro-l-methylindazol-3-yl)carbamate | 1 | 1.38 | 286 |
| 51 | Imidazo[1,2-a]pyridin-8-amine | Phenyl N-(imidazo[1,2-a]pyridin-8-yl)carbamate | 1 | — | 254.1 |
| 52 | 5-Methylisoxazol-3-amine | Phenyl N-(5-methylisoxazol-3-yl)-carbamate | 1 | — | 219.1 |
| 53 | 1,2-Benzoxazol-3-amine | Phenyl N-(1,2-benzoxazol-3-yl)-carbamate | 1 | 1.35 | 255 |
| 54 | 1-Methylindazol-3-amine | Phenyl N-(1-methylindazol-3-yl)-carbamate | 1 | 1.34 | 268 |
| 55 | 5-Amino-6-methylpyridine-2-carbonitrile | Phenyl N-(6-cyano-2-methylpyridin-3-yl)carbamate | 1 | — | 253.2 |
| 56 | 2-Methyl-4-(methylsulfonyl)aniline | Phenyl N-[2-methyl-4-(methylsulfonyl)phenyl]carbamate | 1 | 1.28 | 306 |
| 57 | 6-(Difluoromethoxy)-4-methylpyridin-3-amine | Phenyl N-[6-(difluoromethoxy)-4-methylpyridin-3-yl]carbamate | 1 | 1.42 | 295 |
| 58 | 6-Methoxy-5-methylpyridin-3-amine | Phenyl N-(6-methoxy-5-methylpyridin-3-yl)carbamate | 1 | 1.38 | 259 |
| 59 | 6-Methoxy-4-methylpyridin-3-amine | Phenyl N-(6-methoxy-4-methylpyridin-3-yl)carbamate | 1 | 1.30 | 259 |
| 60 | 5-Methoxy-2-methylaniline | Phenyl N-(5-methoxy-2-methylphenyl)carbamate | 1 | — | 258.1 |
| 61 | 3-Chloro-4-methylaniline | Phenyl N-(3-chloro-4-methylphenyl)-carbamate | 1 | — | 262 |

-continued

| Int. | Amine | Carbamate | LCMS Data Method | RT | $[M + H]^+$ |
|---|---|---|---|---|---|
| 62 | 2,5-Dichloroaniline | Phenyl N-(2,5-dichlorophenyl)-carbamate | 1 | — | 283 |
| 63 | 4-Amino-3-methyl-benzonitrile | Phenyl N-(4-cyano-2-methylphenyl)-carbamate | 1 | 1.57 | 253 |
| 64 | 2,6-Dimethoxypyridin-3-amine | Phenyl N-(2,6-dimethoxypyridin-3-yl)carbamate | 1 | 1.44 | 275 |
| 65 | 4-Methoxy-3-methyl-aniline | Phenyl N-(4-methoxy-3-methyl-phenyl)carbamate | 1 | 1.47 | 258 |
| 66 | 4-(Difluoromethoxy)-2-methylaniline | Phenyl N-[4-(difluoromethoxy)-2-methylphenyl]carbamate | 1 | 1.45 | 294 |

Intermediate 67 tert-Butyl N-(5-bromo-3-methylpyrazin-2-yl)carbamate

To a solution of 2-amino-5-bromo-3-methylpyrazine (46.5 g, 247.3 mmol) in acetonitrile (450 mL) and THF (750 mL) was added DMAP (3 g, 24.7 mmol). The reaction mixture was stirred for 15 minutes before the addition of di-tert-butyl dicarbonate (242 g, 1112.8 mmol). The reaction mixture was stirred overnight at room temperature. The reaction was concentrated in vacuo, then diluted with EtOAc (750 mL) and washed with water (500 mL). The organic layers were dried over magnesium sulphate and concentrated in vacuo. The black tar was purified via flash chromatography, using a 10-15% EtOAc in heptane gradient. The resultant solid was triturated with IPA. The resulting white solid (the bis-tert-butoxycarbonyl derivative) was dissolved in methanol (3000 mL), then $K_2CO_3$ (61.25 g, 443 mmol) was added. The reaction mixture was stirred overnight at room temperature, then at 60° C. for 1 h, then allowed to cool and concentrated in vacuo. The residue was dissolved in DCM (1000 mL), then washed with water (2×1000 mL) and brine (500 mL). The organic layers were dried over magnesium sulphate, then concentrated in vacuo, to give the title compound (38 g, 80% pure by LCMS). LCMS (ES+) $[M+H]^+$ 288.1 and 289.1, RT 1.42 minutes (method 1).

Intermediate 68 tert-Butyl N-[5-(dimethylamino)-3-methylpyrazin-2-yl]carbamate

To Intermediate 67 was added dimethylamine in ethanol (5.6M, 400 mL). The solution was heated at 55° C. overnight in an auotoclave. The crude reaction mixture was concentrated in vacuo and purified by flash chromatography, using a gradient of 20-100% EtOAc in heptane, to yield the title compound (14 g) as a solid. LCMS (ES+) $[M+H]^+$196 (fragment minus tert-butyl), RT 1.56 minutes (method 1).

Intermediate 69

$N^5$,$N^5$,3-Trimethylpyrazine-2,5-diamine

Intermediate 68 (7 g, 27.7 mmol) was taken up in HCl (3.34M in 1,4-dioxane, 70 mL) and stirred at room temperature overnight. The reaction mixture was concentrated in vacuo. The resulting yellow solid was stirred in triethylamine (28 g) for 4 h, then concentrated in vacuo. The resulting black paste was purified by flash chromatography, eluting with a gradient of 50% EtOAc in heptane to 10% MeOH in EtOAc, to give the title compound (2.1 g, 50%). $\delta_H$ ($CDCl_3$) 7.40 (s, 1H), 3.80 (br s, 2H), 3.00 (s, 6H), 2.30 (s, 3H).

Intermediate 70

Phenyl N-[5-(dimethylamino)-3-methylpyrazin-2-yl] carbamate

To a cooled (ice bath) solution of Intermediate 69 (2.1 g, 13.79 mmol) in dry acetonitrile (20 mL) was added pyridine (1.3 g, 16.54 mmol), followed by phenyl chloroformate (2.16 g, 13.79 mmol) dropwise. The reaction mixture was slowly allowed to warm to room temperature over 1 h. The reaction mixture was concentrated in vacuo onto silica, then purified by flash chromatography, eluting with a gradient of 20-60% EtOAc in heptane, to yield the title compound (3.1 g, 82%) as a solid. $\delta_H$ ($CDCl_3$) 7.65 (s, 1H), 7.35 (m, 1H), 7.15 (m, 3H), 6.80 (br s, 1H), 3.05 (s, 6H), 2.42 (s, 3H).

Intermediate 71

2-Ethyl-6-methoxy-3-nitropyridine

To a degassed solution of 2-chloro-6-methoxy-3-nitropyridine (3 g, 15.95 mmol), ethylboronic acid (3 g, 47.80 mmol) and $K_2CO_3$ (6 g, 47.80 mmol) in 1,4-dioxane (60 mL) was added $Pd(dppf)Cl_2$ (1 g, 1.59 mmol). The reaction mixture was stirred at 100° C. for 12 h, then filtered through Celite. The filtrate was concentrated in vacuo and the crude material was purified using column chromatography (silica 100-200 mesh; 10% EtOAc in hexane) to yield the title compound (1.4 g, 48%). $\delta_H$ ($CDCl_3$) 8.20 (d, J 8.1 Hz, 1H), 6.82 (d, J 7.9 Hz, 1H), 4.05 (s, 3H), 3.19 (q, 2H), 1.28 (t, 3H). LCMS: [M+1]183.20 (95.43% LCMS purity).

Intermediate 72

2-Ethyl-6-methoxypyridin-3-amine

To a solution of Intermediate 71 (1.4 g, 7.6 mmol) in MeOH (25 mL) was added Pd/C (150 mg). The reaction mixture was stirred at room temperature for 12 h under an atmosphere of hydrogen (balloon), then filtered through Celite. The filtrate concentrated in vacuo. The crude material was purified using column chromatography (Silica 100-200 mesh, 20% EtOAc in hexane) to yield the title compound (0.9 g, 77%). $\delta_H$ (DMSO-$d_6$) 6.99 (d, J 8.2 Hz, 1H), 6.38 (d, J 8.2 Hz, 1H), 4.28 (s, 2H), 3.70 (s, 3H), 4.55 (s, 2H), 3.70 (s, 3H), 2.25 (q, 2H), 1.18 (t, 3H). LCMS: [M+1]153.1 (99.86% LCMS purity).

Intermediate 73

2-[1-(6-Amino-1-methylpyrazolo[3,4-d]pyrimidin-4-yl)piperazin-2-yl]ethanol dihydrochloride Intermediate 13 (2.00 g, 10.9 mmol) and tert-butyl 3-(2-hydroxyethyl)piperazine-1-carboxylate (10.9 mmol, 2.51 g) in n-butanol (51 mL) and DIPEA (13.1 mmol, 1.71 g, 2.42 mL) was heated at 100° C. for 4 h. The reaction mixture was cooled, partitioned between DCM and water and filtered, then the organic phases were separated and concentrated in vacuo. The residual oil was purified by flash column chromatography on silica (Biotage SNAP 50 g, Isolera, gradient elution: 100% DCM to 35% MeOH/DCM). The resulting clear oil was taken up in DCM (40 mL) and HCl (4N in 1,4-dioxane, 8 mL). The solution was stirred overnight, then concentrated to dryness and washed with diethyl ether. The resulting sticky solid was dried under vacuum to yield the title compound (1.5 g, 39%) as an off-white foam. LCMS (ES+) $[M+H]^+$ 278, RT 2.13 minutes (method 2).

Intermediate 74

2-Amino-4-[(2S,6S)-4-benzyl-2,6-dimethylpiperazin-1-yl]-6-chloropyrimidine-5-carbaldehyde To a solution of (3S,5S)-1-benzyl-3,5-dimethylpiperazine (3 g, 15 mmol) and 2-amino-4,6-dichloropyrimidine-5-carbaldehyde (2.84 g, 14.8 mmol) in n-butanol (30 mL) was added DIPEA (31 mmol). The reaction mixture was heated at 110° C. for 2 h, then cooled and partitioned between water and EtOAc. The aqueous layer was further extracted with EtOAc. The combined organic layers were dried over magnesium sulphate, then concentrated in vacuo. The orange oil was purified by flash column chromatography (4:1 heptane: EtOAc) to give the title compound (4.68 g, 89%) as a yellow oil. LCMS (ES+) $[M+H]^+$ 360, RT 1.69 minutes (method 1).

Intermediate 75

4-[(2S,6S)-4-Benzyl-2,6-dimethylpiperazin-1-yl]-1-methylpyrazolo[3,4-d]pyrimidin-6-amine To a solution of Intermediate 74 (4.6 g, 13 mmol) in THF (43 mL) were added triethylamine (3.96 g, 5.4 mL, 39 mmol) and methylhydrazine (0.6 g, 0.68 mL, 13 mmol). The reaction mixture was stirred for 2 h at room temperature, then partitioned between water and EtOAc. The aqueous layer was further extracted with EtOAc, and the combined organic extracts were concentrated in vacuo. The resulting orange oil was purified by flash column chromatography (EtOAc) to yield the title compound (3.37 g, 74%) as a cream foam. LCMS (ES+) $[M+H]^+$ 352.3, RT 1.53 minutes (method 1).

Intermediate 76

4-[(2S,6S)-2,6-Dimethylpiperazin-1-yl]-1-methylpyrazolo[3,4-d]pyrimidin-6-amine

Intermediate 75 (3.3 g, 9.59 mmol) was dissolved in IMS (190 mL). Pd/C (5%, 2.3 g) and ammonium formate (10 equiv.) were added and the mixture was heated at 80° C. overnight. The reaction mixture was allowed to cool, then filtered through a pad of Celite, washing with MeOH. The combined filtrate and washings were concentrated in vacuo to give the title compound (2.43 g, 93%) as a yellow solid. LCMS (ES+) $[M+H]^+$ 262, RT 0.99 minutes (method 1).

Intermediate 77

4-[4-Benzyl-2-(2,2,2-trifluoroethyl)piperazin-1-yl]-1-methylpyrazolo[3,4-d]pyrimidin-6-amine Intermediate 13 (2.13 g, 11.62 mmol) and 1-benzyl-3-(2,2,2-trifluoroethyl)-piperazine (3 g, 11.62 mmol) in n-butanol (30 mL) and DIPEA (4.5 g, 34.8 mmol) were heated at 100° C. for 72 h. The reaction mixture was cooled, then concentrated in vacuo. The residue was diluted with DCM and washed with sodium bicarbonate, then water, then brine. The organic layers were dried over magnesium sulphate and concentrated in vacuo. The residual oil was purified by flash column chromatography on silica, using a gradient of 40-100% EtOAc in heptane, to yield the title compound (3.2 g, 68%) as a yellow solid. LCMS (ES+) $[M+H]^+$ 406.3, RT 1.61 minutes (method 1).

Intermediate 78

1-Methyl-4-[2-(2,2,2-trifluoroethyl)piperazin-1-yl]pyrazolo[3,4-d]pyrimidin-6-amine dihydrochloride Intermediate 77 (3.2 g, 7.89 mmol) was dissolved in IMS (70 mL). Pd/C (5%, 0.83 g) and ammonium formate (4.97 g) were added and the mixture was heated at 85° C. overnight. The reaction mixture was allowed to cool, then filtered through a pad of Celite, washing with MeOH. The combined filtrate and washings were concentrated in vacuo. The residue was purified by flash chromatography, using a gradient from 100% EtOAc to 10% MeOH with $NH_3$ in EtOAc. The resultant solid was taken up in HCl (4N in 1,4-dioxane, 10 mL) and stirred for 4 h. The precipitate was collected by filtration, then washed with ether and dried, to give the title compound (1.86 g, 66%) as a white solid. LCMS (ES+) $[M+H]^+$ 316.2, RT 1.06 minutes (method 1).

Intermediate 79 tert-Butyl 4-(2-amino-6-chloro-5-formylpyrimidin-4-yl)-3-(trifluoromethyl)piperazine-1-carboxylate To a solution of 3-(trifluoromethyl)piperazine-1-carboxylic acid tert-butyl ester (0.79 g) and 2-amino-4,6-dichloropyrimidine-5-carbaldehyde (0.58 g) in 1,4-dioxane (5.0 mL) was added DIPEA (1.6 mL, 9.0 mmol). The reaction mixture was heated at 120° C. overnight in a sealed Wheaton vial, then allowed to cool and concentrated in vacuo. The residue was partitioned between DCM and water. The organic phases were separated and concentrated in vacuo to give the title compound (1 g, 81%) as a semi-solid. LCMS (ES+) [M+H]+ 410, RT 1.82 minutes (method 2).

Intermediate 80

1-Methyl-4-[2-(trifluoromethyl)piperazin-1-yl]pyrazolo[3,4-d]pyrimidin-6-amine dihydrochloride Intermediate 79 (1 g, 2.44 mmol) in THF (20 mL) was treated with triethylamine (0.68 mL, 4.88 mmol) and methylhydrazine (0.12 g, 0.14 mL). The reaction mixture was stirred at room temperature overnight, then concentrated in vacuo and partitioned between DCM and water. The organic layers were phase separated, then concentrated in vacuo. The material was purified by flash column chromatography on silica (Biotage SNAP 25 g, Isolera, gradient elution: 100% EtOAc to 20% MeOH/EtOAc). The resulting pale yellow foam was dissolved in 4N HCl in 1,4-dioxane (5 mL) and stirred for 2 h. The reaction mixture was concentrated in vacuo to yield the title compound (0.35 g, 87%) as a pale yellow solid. LCMS (ES+) $[M+H]^+$ 302.2, RT 0.7 minutes (method 2).

Intermediate 81

4-[(2S)-2-Isopropylpiperazin-1-yl]-1-methylpyrazolo[3,4-d]pyrimidin-6-amine dihydrochloride 2-Amino-4,6-dichloropyrimidine-5-carbaldehyde (2.4 g, 13 mmol) and tert-butyl (3S)-3-isopropylpiperazine-1-carboxylate (2.9 g, 13 mmol) in 1,4-dioxane (50 mL) were treated with DIPEA (3.3 g, 5 mL, 25 mmol) and heated at 90° C. for 6 h. The reaction mixture was cooled and concentrated in vacuo, then partitioned between DCM and water. The organic layers were phase separated and concentrated. The resulting golden foam was taken up in THF (100 mL) with triethylamine (2.7 g, 4 mL, 27 mmol) and methylhydrazine (0.64 g, 0.73 mL, 14 mmol), then stirred for 72 h at room temperature. The reaction mixture was concentrated in vacuo and partitioned between DCM and water, then phase separated. The organic layers were further concentrated in vacuo. The residual foam was taken up in DCM (100 mL), then 4N HCl in 1,4-dioxane (20 mL) was added and the mixture was stirred overnight. The resultant solution was concentrated in vacuo and triturated with diethyl ether to give the title compound (3.8 g, 95%) as a sticky foam that was >95% pure by LCMS. LCMS (ES+) [M+H]+ 276.2, RT 0.72 minutes (method 2).

Intermediate 82

4-[(2S)-2-Isobutylpiperazin-1-yl]-1-methylpyrazolo[3,4-d]pyrimidin-6-amine dihydrochloride 2-Amino-4,6-dichloropyrimidine-5-carbaldehyde (2.3 g, 12 mmol) and tert-butyl (3S)-3-isobutylpiperazine-1-carboxylate (12 mmol, 2.9 g) in 1,4-dioxane (50 mL) were treated with DIPEA (3.3 g, 5 mL, 25 mmol) and heated at 90° C. for 6 h. The reaction mixture was cooled and concentrated in vacuo, then partitioned between DCM and water. The organic layers were phase separated and concentrated. The resulting golden foam was taken up in THF (100 mL) with triethylamine (2.5 g, 4 mL, 25 mmol) and methylhydrazine (0.61 g, 0.70 mL, 13 mmol), then stirred for 72 h at room temperature. The reaction mixture was concentrated in vacuo and partitioned between DCM and water, then phase separated. The organic layers were further concentrated in vacuo. The residual foam was taken up in DCM (100 mL), then 4N HCl in 1,4-dioxane (20 mL) was added and the mixture was stirred overnight. The resultant solution was concentrated in vacuo and triturated with diethyl ether to give the title compound (3.6 g, 92%) as a sticky foam that was >90% pure by LCMS. LCMS (ES+) [M+H]+ 290.2, RT 0.92 minutes (method 2).

Intermediate 83

3-Bromo-4-chloro-1H-pyrazolo[3,4-d]pyrimidin-6-amine

To a suspension of Intermediate 1 (923 mg, 5.44 mmol) and sodium acetate (4.13 g, 50.4 mmol) in a mixture of acetic acid (50 mL) and water (10 mL) at 0° C. was added bromine (2.2 mL, 43.54 mmol) dropwise. The reaction mixture was allowed to warm to room temperature and continuously stirred for 5.5 h. The reaction mixture was concentrated in vacuo. The residue was precipitated into water. The precipitate was collected by filtration and dried in vacuo to provide the title compound (0.99 g, 73%). $^{13}C$ NMR δ (DMSO-$d_6$, 75 MHz) 161.6 (C-2), 157.9 (C-4), 153.0 (C-7a), 119.5 (C-5), 103.9 (C-4a). MS (m/z) 247, 249 $[M+H]^+$.

Intermediate 84 tert-Butyl (3S)-4-(6-amino-3-bromo-1H-pyrazolo[3,4-d]pyrimidin-4-yl)-3-methylpiperazine-1-carboxylate A mixture of Intermediate 83 (1 g, 4.02 mmol), tert-butyl (3S)-3-methyl-piperazine-1-carboxylate (806 mg, 4.02 mmol) and DIPEA (1.4 mL, 8.04 mmol) in DMF (25 mL) was heated at 105° C. for 39 h. The reaction mixture was evaporated in vacuo and purified by silica gel chromatography (DCM/MeOH, 40:1) to provide the title compound (849 mg, 51%). $^{13}C$ NMR δ ($CDCl_3$+$CD_3OD$, 75 MHz) 161.6 (C-4), 160.2 (C-2), 159.5 (C═O), 156.1 (C-7a), 120.4 (C-5), 97.6 (C-4a), 80.9 [$OC(CH_3)_3$], 52.1 ($NCH_2$), 43.2 ($NCH_2$), 28.5 ($CH_3$), 14.9 [(S)—$CH_3$]. MS (m/z) 412, 414 $[M+H]^+$.

Intermediate 85 tert-Butyl (3S)-4-(6-amino-3-bromo-1-methylpyrazolo[3,4-d]pyrimidin-4-yl)-3-methyl-piperazine-1-carboxylate To a solution of Intermediate 84 (849 mg, 2.06 mmol) in DMF (10 mL) was added NaH (60%, 99 mg, 2.47 mmol) at 0° C. under $N_2$. The reaction mixture was warmed to room temperature over 10 minutes, then cooled to 0° C. Iodomethane (154 μL, 2.47 mmol) was added and the reaction mixture was continuously stirred for 3.5 h. The reaction mixture was quenched with cold aqueous $NH_4Cl$ solution, then extracted with DCM twice. The organic phase was washed with water and brine, then dried with anhydrous $Na_2SO_4$, filtered and concentrated in vacuo. The residue was purified by silica gel chromatography, eluting with DCM/MeOH (80:1) then DCM/MeOH (40:1), to provide the title compound (625 mg, 71%). $^{13}C$ NMR δ ($CDCl_3$, 75 MHz) 160.9 (C-4), 159.8 (C-2), 158.2 (C═O), 155.4 (C-7a), 118.5 (C-5), 98.0 (C-4a), 80.1 [$OC(CH_3)_3$], 51.8 ($NCH_2$), 43.0 ($NCH_2$), 33.8 ($NCH_3$), 28.5 ($CH_3$), 14.9 [(S)—$CH_3$]. MS (m/z) 426, 428 $[M+H]^+$.

Intermediate 86 tert-Butyl (3S)-4-[6-amino-3-(4-fluorophenyl)-1-methylpyrazolo[3,4-d]pyrimidin-4-yl]-3-methylpiperazine-1-carboxylate To a suspension of Intermediate 85 (105 mg, 0.246 mmol) in a mixture of 1,4-dioxane (1.6 mL) and water (0.4 mL) were added 4-fluorophenylboronic acid (31 mg, 0.246 mmol), tetrakis(triphenylphosphine)palladium(0) (15 mg, 0.012 mmol) and $K_2CO_3$ (102 mg, 0.739 mmol). The reaction mixture was degassed and heated at 110° C. under microwave irradiation (150 W) for 1 h under $N_2$. The reaction mixture was concentrated in vacuo and purified by silica gel chromatography, eluting with DCM/MeOH (40:1)

then DCM/MeOH (30:1), to provide the title compound (83 mg, 79%). MS (m/z) 442 $[M+H]^+$.

Intermediate 87 tert-Butyl (3S)-4-[6-amino-1-methyl-3-(pyridin-3-yl)pyrazolo[3,4-d]pyrimidin-4-yl]-3-methylpiperazine-1-carboxylate To a suspension of Intermediate 85 (105 mg, 0.246 mmol) in a mixture of 1,4-dioxane (1.6 mL) and water (0.4 mL) were added pyridin-3-ylboronic acid (35 mg, 0.246 mmol), tetrakis(triphenylphosphine)palladium(0) (15 mg, 0.012 mmol) and $K_2CO_3$ (102 mg, 0.739 mmol). The reaction mixture was degassed and heated at 110° C. under microwave irradiation (150 W) for 1 h under $N_2$. The reaction mixture was concentrated in vacuo and purified by silica gel chromatography, eluting with DCM/MeOH (60:1) then DCM/MeOH (40:1), to provide the title compound (97 mg, 89%). $^{13}C$ NMR δ ($CDCl_3$, 75 MHz) 161.3 (C-4), 160.8 (C-2), 158.5 (C-7a), 155.1 (C═O), 149.6 (py), 149.5 (py), 141.1 (py), 135.2 (py), 130.7 (C-5), 123.5 (py), 95.8 (C-4a), 80.0 $[OC(CH_3)_3]$, 50.8 ($NCH_2$), 48.0 ($NCH_2$), 43.3 ($NCH_2$), 42.6 ($NCH_2$), 33.7 (NMe), 28.4 (Me), 14.3 (Me). MS (m/z) 425 $[M+H]^+$.

Intermediate 88

3-(4-Fluorophenyl)-1-methyl-4-[(2S)-2-methylpiperazin-1-yl]pyrazolo[3,4-d]pyrimidin-6-amine A mixture of Intermediate 86 (97 mg, 0.22 mmol) in TFA (4 mL) and DCM (4 mL) was stirred for 40 minutes. The reaction mixture was evaporated in vacuo, then co-evaporated with $NH_3$-MeOH solution (7N) to dryness, to provide the crude title compound, which was used directly for the next stage without further purification. MS (m/z) 342 $[M+H]^+$.

Intermediate 89

1-Methyl-4-[(2S)-2-methylpiperazin-1-yl]-3-(pyridin-3-yl)pyrazolo[3,4-d]pyrimidin-6-amine A mixture of Intermediate 87 (83 mg, 0.195 mmol) in TFA (4 mL) and DCM (4 mL) was stirred for 30 minutes. The reaction mixture was evaporated in vacuo, then co-evaporated with $NH_3$-MeOH solution (7N) to dryness, to provide the crude title compound, which was used directly for the next stage without further purification. MS (m/z) 325 $[M+H]^+$.

Example 1 (Method B)

6-Amino-4-{4-[(4-methoxy-2-methylphenyl)carbamyl]piperazin-1-yl}-1H-pyrazolo[3,4-d]pyrimidine To a suspension of Intermediate 2 (66 mg, 0.3 mmol) in DMF (2 mL) at r.t. was added 4-methoxy-2-methylphenyl isocyanate (40 μL, 0.3 mmol). The reaction mixture was stirred overnight, then concentrated under reduced pressure. The residue was purified by silica gel chromatography (DCM:MeOH 20:1; then DCM:MeOH:$NH_3$-MeOH (7N) 10:1:1%) to provide the title compound (52 mg, 45%) as a white solid. $^{13}C$ NMR δ (DMSO-$d_6$, 75 MHz) 161.4 (C-2), 158.6 (C-4), 157.1 (C-7a), 156.6 (C═O), 155.9 (phenyl), 135.3 (phenyl), 133.7 (C-5), 130.6 (phenyl), 127.9 (phenyl), 115.1 (phenyl), 110.9 (phenyl), 94.5 (C-4a), 55.1 (OMe), 44.2 ($NCH_2$), 43.2 ($NCH_2$), 18.1 (Me). MS (m/z) 383 $[M+H]^+$.

Example 2

6-Amino-4-{4-[(4-methoxyphenyl)carbamyl]piperazin-1-yl}-1H-pyrazolo[3,4-d]-pyrimdine Prepared via Method B using Intermediate 2 (66 mg, 0.3 mmol) and 4-methoxyphenyl isocyanate (40 μL, 0.3 mmol). The title compound (51 mg, 46%) was obtained as a white solid. $^{13}C$ NMR δ (DMSO-$d_6$, 75 MHz) 161.4 (C-2), 158.6 (C-4), 157.1 (C-7a), 155.3 (C═O), 154.5 (phenyl), 133.7 (C-5), 133.3 (phenyl), 121.7 (phenyl), 113.5 (phenyl), 94.5 (C-4a), 55.1 (OMe), 44.2 ($NCH_2$), 43.1 ($NCH_2$). MS (m/z) 369 $[M+H]^+$.

Example 3

6-Amino-4-{4-[(4-methoxy-2-methylphenyl)carbamyl]-2-(S)-methylpiperazin-1-yl}-1H-pyrazolo[3,4-d]pyrimidine Prepared via Method B using Intermediate 4 (0.29 mmol) and 4-methoxy-2-methylphenyl isocyanate (39 μL, 0.29 mmol). The title compound (47 mg, 41%) was obtained as a white solid. MS (m/z) 397 $[M+H]^+$.

Example 4

6-Amino-4-{4-[(4-methoxyphenyl)carbamyl]-2-(S)-methylpiperazin-1-yl}-1H-pyrazolo[3,4-d]pyrimidine Prepared via Method B using Intermediate 4 (0.29 mmol) and 4-methoxyphenyl isocyanate (37 μL, 0.29 mmol). The title compound (23 mg, 21%) was obtained as a white solid. $\delta_H$ (DMSO-$d_6$, 300 MHz) 1.23 (s, 3H), 3.11-3.16 (m, 1H), 3.43 (m, 2H), 3.71 (s, 3H), 3.96-4.06 (m, 2H), 4.39-4.77 (m, 2H), 6.04 (br, 2H), 6.82 (d, J 7.5 Hz, 2H), 7.33 (d, J 7.5 Hz, 2H), 7.93 (s, 1H), 8.42 (s, 1H), 12.61 (s, 1H). MS (m/z) 383 $[M+H]^+$.

Example 5

6-Amino-4-{4-[(4-methoxy-2-methylphenyl)carbamyl]-2-(S)-methylpiperazin-1-yl}-1-methylpyrazolo[3,4-d]pyrimidine Prepared via Method B using Intermediate 7 (0.25 mmol) and 4-methoxy-2-methylphenyl isocyanate (34 μL, 0.25 mmol). The title compound (100 mg, 97%) was obtained as a white solid. $^{13}C$ NMR δ (DMSO-$d_6$, 150 MHz) 161.5 (C-2), 157.0 (C-4), 156.9 (C-7a), 156.7 (C═O), 156.2 (phenyl), 135.6 (phenyl), 132.8 (C-5), 130.7 (phenyl), 128.1 (phenyl), 115.2 (phenyl), 111.1 (phenyl), 94.7 (C-4a), 55.2 (OMe), 47.2 ($NCH_2$), 43.2 ($NCH_2$), 33.1 (NMe), 18.1 (Me), 15.3 (Me). MS (m/z) 411 $[M+H]^+$.

Example 6

6-Amino-4-{4-[(4-methoxyphenyl)carbamyl]-2-(S)-methylpiperazin-1-yl}-1-methylpyrazolo[3,4-d]pyrimidine Prepared via Method B using Intermediate 7 (0.31 mmol) and 4-methoxyphenyl isocyanate (40 μL, 0.31 mmol). The title compound (131 mg, quantitative) was obtained as a white solid. $^{13}C$ NMR δ (DMSO-$d_6$, 75 MHz) 161.0 (C-2), 157.3 (C-4), 156.4 (C-7a), 156.2 (C═O), 156.1 (phenyl), 132.6 (phenyl), 131.9 (C-5), 123.1 (phenyl), 114.1 (phenyl), 95.8 (C-4a), 55.5 (OMe), 49.3 (NCH), 47.0 (NCH), 43.3 (NCH), 39.5 (NCH), 33.6 (NMe), 16.2 (Me). MS (m/z) 397 $[M+H]^+$.

Example 7

6-Amino-4-[4-(indan-5-ylcarbamyl)-2-(S)-methylpiperazin-1-yl]-methylpyrazolo[3,4-d]pyrimidine Prepared via Method B using Intermediate 7 (0.31 mmol) and 5-indanyl isocyanate (45 μL, 0.31 mmol). The title compound (130 mg, quantitative) was obtained as a white solid. $^{13}C$ NMR δ (DMSO-$d_6$, 75 MHz) 161.1 (C-2), 157.4 (C-4), 156.5 (C-7a), 155.9 (C═O), 145.0 (phenyl), 139.5 (phenyl), 136.9 (phenyl), 132.6 (C-5), 124.3 (phenyl), 119.0 (phenyl), 117.4 (phenyl), 95.9 (C-4a), 49.3 (NCH), 47.1 (NCH), 43.4 (NCH), 39.6 (NCH), 33.6 (NMe), 33.0 ($CH_2$), 32.2 ($CH_2$), 25.6 ($CH_2$), 16.2 (Me). MS (m/z) 407 $[M+H]^+$.

Example 8

6-Amino-4-(4-{[4-(dimethylamino)phenyl]carbamyl}-2-(S)-methylpiperazin-1-yl)-1-methylpyrazolo[3,4-d]pyrimidine Prepared via Method B using Intermediate 7 (0.2 mmol) and 4-(dimethylamino)-phenyl isocyanate (33 μL, 0.2 mmol). The title compound (82 mg, 100%) was obtained as a white solid. $^{13}C$ NMR δ ($CDCl_3$+MeOD, 75 MHz) 160.9, 157.4, 156.3, 132.8, 123.3, 113.3, 95.9, 49.4, 47.1, 43.4, 41.3, 39.7, 33.7, 16.3. MS (m/z) 410 $[M+H]^+$.

Example 9 (Method C)

(3S)-4-(6-Amino-1,3-dimethylpyrazolo[3,4-d]pyrimidin-4-yl)-N-[6-(3,3-difluoroazetidin-1-yl)-2-methylpyridin-3-yl]-3-methylpiperazine-1-carboxamide To Intermediate 12 (0.1 g, 0.27 mmol) and Intermediate 23 (0.1 g, 0.32 mmol) were added acetonitile (5 mL) and DIPEA (0.21 mL, 1.2 mmol). The mixture was stirred at 50° C. under nitrogen for 2.5 h, then concentrated in vacuo to yield a brown oil. The crude material was purified by preparative HPLC to give the title compound (0.073 g, 54.0%) as a white freeze-dried solid. $\delta_H$ (DMSO-$d_6$) 7.99 (s, 1H), 7.28 (d, J 8.6 Hz, 1H), 6.32 (d, J 8.6 Hz, 1H), 6.17 (s, 2H), 4.53-4.42 (m, 1H), 4.26 (t, J 12.7 Hz, 4H), 4.04 (d, J 12.4 Hz, 1H), 3.93-3.82 (m, 1H), 3.57 (s, 3H), 3.36-3.22 (m, 2H), 3.14 (dd, J 13.2, 3.5 Hz, 1H), 3.04-2.92 (m, 1H), 2.35 (s, 3H), 2.18 (s, 3H), 1.17 (d, J 6.6 Hz, 3H). LCMS (ES−) 485 $[M-H]^-$, RT 1.57 minutes (method 2).

Example 10

(3S)-4-(6-Amino-1,3-dimethylpyrazolo[3,4-d]pyrimidin-4-yl)-N-(4-methoxy-2-methylphenyl)-3-methylpiperazine-1-carboxamide Prepared via Method C using Intermediate 12 (0.26 mmol) and Intermediate 25 (0.37 mmol) to yield the title compound (0.072 g, 63.9%) as a white freeze-dried solid. $\delta_H$ (DMSO-$d_6$) 7.90 (s, 1H), 6.96 (d, J 8.8 Hz, 1H), 6.71 (d, J 3.0 Hz, 1H), 6.63 (dd, J 8.6, 3.0 Hz, 1H), 6.17 (s, 2H), 4.54-4.41 (m, 1H), 4.04 (d, J 12.9 Hz, 1H), 3.94-3.80 (m, 1H), 3.65 (s, 3H), 3.57 (s, 3H), 3.36-3.19 (m, 1H), 3.13 (dd, J 13.0, 3.2 Hz, 1H), 3.03-2.90 (m, 1H), 2.35 (s, 3H), 2.08 (s, 3H), 1.17 (d, J 6.6 Hz, 3H). LCMS (ES+) 425.8 $[M+H]^+$, RT 1.36 minutes (method 4).

Example 11

(3S)-4-(6-Amino-1,3-dimethylpyrazolo[3,4-d]pyrimidin-4-yl)-N-(6-methoxy-2-methyl-pyridin-3-yl)-3-methylpiperazine-1-carboxamide Prepared via Method C using Intermediate 12 (0.24 mmol) and Intermediate 24 (0.34 mmol) to yield the title compound (0.064 g, 63.6%) as a white freeze-dried solid. $\delta_H$ (DMSO-$d_6$) 8.05 (s, 1H), 7.36 (d, J 8.6 Hz, 1H), 6.53 (d, J 8.6 Hz, 1H), 6.18 (s, 2H), 4.53-4.42 (m, 1H), 4.05 (br d, J 13.0 Hz, 1H), 3.94-3.82 (m, 2H), 3.74 (s, 3H), 3.57 (s, 3H), 3.38-3.29 (m, 1H), 3.15 (dd, J 13.2, 3.4 Hz, 1H), 3.06-2.93 (m, 1H), 2.36 (s, 3H), 2.22 (s, 3H), 1.17 (d, J 6.6 Hz, 3H). LCMS (ES−) 424.0 $[M-H]^-$, RT 1.35 minutes (method 2).

Example 12

(3R)-4-(6-Amino-1-methylpyrazolo[3,4-d]pyrimidin-4-yl)-N-[6-(3,3-difluoroazetidin-1-yl)-2-methylpyridin-3-yl]-3-(hydroxymethyl)piperazine-1-carboxamide Prepared via Method C using Intermediate 15 (0.54 mmol) and Intermediate 23 (0.54 mmol) to yield the title compound (0.021 g, 8%) as a white solid. $\delta_H$ (DMSO-$d_6$) 8.02 (s, 1H), 7.91 (s, 1H), 7.37 (d, J 8.5 Hz, 1H), 6.39 (d, J 8.5 Hz, 1H), 6.17 (s, 2H), 5.01 (br s, 1H), 4.70-4.35 (br s, 2H), 4.32 (t, J 12.7 Hz, 4H), 4.17 (d, J 13.2 Hz, 1H), 4.01-3.80 (m, 1H), 3.70 (s, 3H), 3.69-3.51 (m, 2H), 3.39-3.02 (m, 3H), 2.21 (s, 3H). LCMS (ES−) 487 $[M-H]^-$, RT 1.29 minutes (method 2).

Example 13

(3S)-4-(6-Amino-1-methylpyrazolo[3,4-d]pyrimidin-4-yl)-N-[6-(3,3-difluoroazetidin-1-yl)-2-methylpyridin-3-yl]-3-methylpiperazine-1-carboxamide Prepared via Method C using Intermediate 7 (0.29 mmol) and Intermediate 23 (0.34 mmol) to yield the title compound (0.084 g, 61.5%) as a white freeze-dried solid. $\delta_H$ (DMSO-$d_6$) 8.01 (s, 1H), 7.86 (s, 1H), 7.29 (d, J 8.4 Hz, 1H), 6.33 (d, J 8.4 Hz, 1H), 6.12 (s, 2H), 4.86-4.56 (s, 1H), 4.26 (t, J 12.7 Hz, 4H), 4.50-4.20 (br s, 1H), 4.02 (d, J 2.1 Hz, 1H), 3.90 (d, J 13.4 Hz, 1H), 3.64 (s, 3H), 3.42-3.15 (m, 2H), 3.11-2.98 (m, 1H), 2.18 (s, 3H), 1.17 (d, J 6.5 Hz, 3H). LCMS (ES−) 471 $[M-H]^-$, RT 1.42 minutes (method 2).

Example 14

(3S)-4-(6-Amino-1-methylpyrazolo[3,4-d]pyrimidin-4-yl)-N-(6-methoxy-2-methyl-pyridin-3-yl)-3-methylpiperazine-1-carboxamide Prepared via Method C using Intermediate 7 (0.28 mmol) and Intermediate 24 (0.36 mmol) to yield the title compound (0.072 g, 60.7%) as a white freeze-dried solid. $\delta_H$ (DMSO-$d_6$) 8.08 (s, 1H), 7.86 (s, 1H), 7.36 (d, J 8.6 Hz, 1H), 6.54 (d, J 8.6 Hz, 1H), 6.12 (s, 2H), 4.94-4.52 (s, 1H), 4.52-4.17

(s, 1H), 4.03 (d, J 12.5 Hz, 1H), 3.91 (d, J 13.2 Hz, 1H), 3.75 (s, 3H), 3.64 (s, 3H), 3.46-3.15 (m, 2H), 3.12-2.99 (m, 1H), 2.22 (s, 3H), 1.17 (d, J 6.6 Hz, 3H). LCMS (ES−) 410 $[M-H]^-$, RT 1.23 minutes (method 2).

Example 15 (Method D)

(3R)-4-(6-Amino-1-methylpyrazolo[3,4-d]pyrimidin-4-yl)-N-(4-methoxy-2-methyl-phenyl)-3-methylpiperazine-1-carboxamide Intermediate 22 (3.5 g, 12 mmol) and DIPEA (25 mmol) were stirred in DCM (150 mL) at 0° C. (ice bath) for 30 minutes with 4-methoxy-2-methylphenyl isocyanate (12 mmol). After 30 minutes, water was added and the mixture was acidified with 10% aqueous HCl solution. The aqueous layer was further extracted with DCM, then neutralised with saturated aqueous sodium bicarbonate solution. The neutralised aqueous layer was extracted with DCM, then the organic phase was separated and concentrated in vacuo. The recovered crude solid was triturated with ether, to yield the title compound (1.68 g, 33%) as a fine powder. $\delta_H$ (DMSO-$d_6$) 8.01 (s, 1H), 7.92 (s, 1H), 7.03 (d, J 8.6 Hz, 1H), 6.77 (d, J 2.9 Hz, 1H), 6.70 (dd, J 8.6, 2.9 Hz, 1H), 6.21 (s, 1H), 4.80-4.20 (m, 2H), 4.09 (d, J 12.6 Hz, 1H), 3.97 (d, J 13.1 Hz, 1H), 3.71 (s, 3H), 3.70 (s, 3H), 3.41-3.01 (m, 3H), 2.13 (s, 3H), 1.23 (d, J 6.5 Hz, 3H). LCMS (ES+) 411 $[M+H]^+$, RT 1.45 minutes (method 2).

Example 16 (Method E)

(3S)-4-[6-Amino-1-methyl-3-(trifluoromethyl)pyrazolo[3,4-d]pyrimidin-4-yl]-N-[6-(3,3-difluoroazetidin-1-yl)-2-methylpyridin-3-yl]-3-methylpiperazine-1-carboxamide To Intermediate 19 (0.05 g, 0.12 mmol) and Intermediate 23 (0.05 g, 0.160 mmol) were added acetonitrile (5 mL) and DIPEA (0.1 mL, 0.6 mmol) and the mixture was stirred at r.t. under nitrogen overnight. The solvent was removed in vacuo to yield a brown oil that was purified by preparative HPLC, to yield the title compound (0.033 g, 49.4%) as a freeze-dried white solid. $\delta_H$ (DMSO-$d_6$) 8.06 (s, 1H), 7.35 (d, J 8.5 Hz, 1H), 6.72 (s, 2H), 6.39 (d, J 8.6 Hz, 1H), 4.51-4.40 (m, 1H), 4.33 (t, J 12.5 Hz, 4H), 4.14-4.04 (m, 1H), 3.99-3.90 (m, 1H), 3.80 (s, 3H), 3.72-3.64 (m, 1H), 3.47-3.35 (m, 1H), 3.27-3.19 (m, 1H), 3.07-2.96 (m, 1H), 2.24 (s, 3H), 1.20 (d, J 6.5 Hz, 3H). LCMS (ES+) 541.8 $[M+H]^+$, RT 1.61 minutes (method 4).

Example 17

(3S)-4-[6-Amino-1-methyl-3-(trifluoromethyl)pyrazolo[3,4-d]pyrimidin-4-yl]-N-(6-methoxy-2-methylpyridin-3-yl)-3-methylpiperazine-1-carboxamide Prepared via Method E using Intermediate 19 (0.12 mmol) and Intermediate 24 (0.17 mmol) to yield the title compound (0.023 g, 39.4%) as an off-white freeze-dried solid. $\delta_H$ (DMSO-$d_6$) 8.12 (s, 1H), 7.42 (d, J 8.4 Hz, 1H), 6.73 (s, 2H), 6.60 (d, J 8.6 Hz, 1H), 4.52-4.40 (m, 1H), 4.15-4.03 (m, 1H), 4.00-3.90 (m, 1H), 3.82 (s, 6H), 3.73-3.64 (m, 1H), 3.49-3.35 (m, 1H), 3.31 (s, 3H), 3.24 (dd, J 13.0, 3.2 Hz, 1H), 3.09-2.97 (m, 1H), 2.28 (s, 3H), 1.21 (d, J 6.6 Hz, 3H). LCMS (ES+) 480.8 $[M+H]^+$, RT 1.76 minutes (method 4).

Example 18

(3S)-4-[6-Amino-1-methyl-3-(trifluoromethyl)pyrazolo[3,4-d]pyrimidin-4-yl]-N-(4-methoxy-2-methylphenyl)-3-methylpiperazine-1-carboxamide Prepared via Method E using Intermediate 19 (0.12 mmol) and Intermediate 25 (0.17 mmol) to yield the title compound (0.021 g, 37.5%) as an off-white freeze-dried solid. $\delta_H$ (DMSO-$d_6$) 7.97 (s, 1H), 7.02 (d, J 8.6 Hz, 1H), 6.79-6.67 (m, 4H), 4.51-4.39 (m, 1H), 4.14-4.04 (m, 1H), 3.99-3.91 (m, 1H), 3.81 (s, 3H), 3.72 (s, 3H), 3.71-3.63 (m, 1H), 3.47-3.34 (m, 1H), 3.26-3.17 (m, 1H), 3.06-2.93 (m, 1H), 2.14 (s, 3H), 1.20 (d, J 6.7 Hz, 3H). LCMS (ES+) 479.8 $[M+H]^+$, RT 2.06 minutes (method 4).

Examples 19 to 30 (Method F)

To a solution of the appropriate amine (0.29 mmol) in DMF (2 mL) were added DIPEA (0.30 mmol) and 1,1'-carbonyldiimidazole (0.41 mmol). The mixture was stirred at r.t. for 30 minutes. A solution of Intermediate 7 (0.28 mmol) and DIPEA (0.30 mmol) in DMF (lmL) was added. The mixture was stirred at r.t. for up to 16 h. The progress of the reaction was monitored by LCMS. Upon completion, the reaction mixture was diluted with water and extracted with EtOAc. The organic layer was washed with brine, then water, and dried over sodium sulfate. The organic layer was concentrated in vacuo and the resulting crude material was purified either by column chromatography (silica gel 100-200 mesh, 10% MeOH/DCM), or reverse-phase preparative HPLC, to afford the title compound.

| | | LCMS Data | | |
|---|---|---|---|---|
| Ex. | Name | Method | RT | $[M + H]^+$ |
| 19 | (3S)-4-(6-Amino-1-methylpyrazolo[3,4-d]pyrimidin-4-yl)-N-(2,1,3-benzothiadiazol-4-yl)-3-methylpiperazine-1-carboxamide | 2 | 1.56 | 407.8 |
| 20 | (3S)-4-(6-Amino-1-methylpyrazolo[3,4-d]pyrimidin-4-yl)-N-(1H-indazol-7-yl)-3-methylpiperazine-1-carboxamide | 2 | 1.33 | 407.8 |
| 21 | (3S)-4-(6-Amino-1-methylpyrazolo[3,4-d]pyrimidin-4-yl)-N-(2,1,3-benzothiadiazol-5-yl)-3-methylpiperazine-1-carboxamide | 2 | 1.53 | 425.8 |
| 22 | (3S)-4-(6-Amino-1-methylpyrazolo[3,4-d]pyrimidin-4-yl)-N-(1H-indol-7-yl)-3-methylpiperazine-1-carboxamide | 2 | 1.55 | 406.8 |
| 23 | (3S)-4-(6-Amino-1-methylpyrazolo[3,4-d]pyrimidin-4-yl)-N-(1H-indol-4-yl)-3-methylpiperazine-1-carboxamide | 2 | 1.29 | 406.8 |
| 24 | (3S)-4-(6-Amino-1-methylpyrazolo[3,4-d]pyrimidin-4-yl)-3-methyl-N-(2-methyl-1H-benzimidazol-4-yl)piperazine-1-carboxamide | 2 | 1.25 | 421.8 |

-continued

| Ex. | Name | LCMS Data Method | RT | [M + H]+ |
|---|---|---|---|---|
| 25 | (3S)-4-(6-Amino-1-methylpyrazolo[3,4-d]pyrimidin-4-yl)-3-methyl-N-(1-methylindazol-7-yl)piperazine-1-carboxamide | 2 | 1.26 | 421.8 |
| 26 | (3S)-4-(6-Amino-1-methylpyrazolo[3,4-d]pyrimidin-4-yl)-3-methyl-N-(4-methyl-1H-indazol-7-yl)piperazine-1-carboxamide | 2 | 1.49 | 421.8 |
| 27 | (3S)-4-(6-Amino-1-methylpyrazolo[3,4-d]pyrimidin-4-yl)-N-(6-hydroxy-2-methylpyridin-3-yl)-3-methylpiperazine-1-carboxamide | 2 | 0.85 | 398.8 |
| 28 | (3S)-4-(6-Amino-1-methylpyrazolo[3,4-d]pyrimidin-4-yl)-3-methyl-N-[2-methyl-6-(2,2,2-trifluoroethoxy)pyridin-3-yl]-piperazine-1-carboxamide | 2 | 1.86 | 480.8 |
| 29 | (3S)-4-(6-Amino-1-methylpyrazolo[3,4-d]pyrimidin-4-yl)-N-(1,2-dimethyl-6-oxopyridin-3-yl)-3-methylpiperazine-1-carboxamide | 2 | 0.95 | 412.8 |
| 30 | (3S)-4-(6-Amino-1-methylpyrazolo[3,4-d]pyrimidin-4-yl)-3-methyl-N-[2-methyl-6-(methylamino)pyridin-3-yl]-piperazine-1-carboxamide | 2 | 1.14 | 411.8 |

Examples 31 to 37 (Method G)

To a solution of the indicated amine (0.57 mmol) in THF (10 mL) at 0° C. was added pyridine (0.75 mmol), followed by phenyl chloroformate (0.69 mmol). The reaction mixture was stirred at 0° C. for 2 h. The reaction mixture was diluted with EtOAc, then washed with saturated aqueous sodium bicarbonate solution, water and brine. The organic layer was concentrated in vacuo. To a solution of the resulting material (0.53 mmol) and Intermediate 7 (0.35 mmol) in DMSO (2 mL) was added DIPEA (1.0 mmol). The reaction mixture was heated at 60° C. for 3 h. After this time, the reaction mixture was diluted with EtOAc, then the organic layer was washed with water and brine, dried over sodium sulfate, and concentrated in vacuo. The resulting crude material was purified by flash column chromatography on silica (100-200 mesh, 5% MeOH/DCM), to afford the title compound as an off-white solid.

| Ex. | Amine | Name | LCMS Data Method | RT | [M + H]+ |
|---|---|---|---|---|---|
| 31 | Intermediate 30 | (3S)-4-(6-Amino-1-methylpyrazolo-[3,4-d]pyrimidin-4-yl)-N-[2-(3,3-difluoroazetidin-1-yl)-4-methyl-pyrimidin-5-yl]-3-methylpiperazine-1-carboxamide | 5 | 1.57 | 473.3 |
| 32 | 4-(Difluoro-methoxy)-2-methylaniline | (3S)-4-(6-Amino-1-methylpyrazolo-[3,4-d]pyrimidin-4-yl)-N-[4-(difluoro-methoxy)-2-methylphenyl]-3-methyl-piperazine-1-carboxamide | 5 | 1.89 | 447.3 |
| 33 | Intermediate 29 | (3S)-4-(6-Amino-1-methylpyrazolo-[3,4-d]pyrimidin-4-yl)-N-[2-(dimethyl-amino)-4-methylpyrimidin-5-yl]-3-methylpiperazine-1-carboxamide | 5 | 1.54 | 426.3 |
| 34 | 6-(Azetidin-1-yl)-2-methylpyridin-3-amine (WO 2010/139747) | (3S)-4-(6-Amino-1-methylpyrazolo-[3,4-d]pyrimidin-4-yl)-N-[6-(azetidin-1-yl)-2-methylpyridin-3-yl]-3-methyl-piperazine-1-carboxamide | 5 | 1.37 | 436.5 |
| 35 | Intermediate 27 | (3S)-4-(6-Amino-1-methylpyrazolo-[3,4-d]pyrimidin-4-yl)-N-[6-(3,3-difluoroazetidin-1-yl)-4-methylpyridin-3-yl]-3-methylpiperazine-1-carboxamide | 5 | 1.57 | 473.3 |
| 36 | $N^2$,$N^2$,6-Trimethyl-pyridine-2,5-diamine (WO 2010/139747) | (3S)-4-(6-Amino-1-methylpyrazolo-[3,4-d]pyrimidin-4-yl)-N-[6-(dimethyl-amino)-2-methylpyridin-3-yl]-3-methylpiperazine-1-carboxamide | 5 | 1.45 | 425.3 |
| 37 | $N^2$,$N^2$,4-Trimethyl-pyridine-2,5-diamine (WO 2009/093747) | (3S)-4-(6-Amino-1-methylpyrazolo-[3,4-d]pyrimidin-4-yl)-N-[6-(dimethyl-amino)-4-methylpyridin-3-yl]-3-methylpiperazine-1-carboxamide | 5 | 1.43 | 425.3 |

Examples 38 to 40

The following compounds were prepared via Method G, using Intermediate 12.

| Ex. | Amine | Name | LCMS Data Method | RT | [M + H]+ |
|---|---|---|---|---|---|
| 38 | 6-(Azetidin-1-yl)-2-methylpyridin-3-amine (WO 2010/139747) | (3S)-4-(6-Amino-1,3-dimethylpyrazolo[3,4-d]pyrimidin-4-yl)-N-[6-(azetidin-1-yl)-2-methylpyridin-3-yl]-3-methylpiperazine-1-carboxamide | 5 | 1.47 | 451.3 |
| 39 | $N^2$,$N^2$,4-Trimethylpyridine-2,5-diamine (WO 2009/093747) | (3S)-4-(6-Amino-1,3-dimethylpyrazolo[3,4-d]pyrimidin-4-yl)-N-[6(dimethylamino)-4-methylpyridin-3-yl]-3-methylpiperazine-1-carboxamide | 5 | 1.53 | 439.4 |
| 40 | $N^2$,$N^2$,6-Trimethylpyridine-2,5-diamine (WO 2010/139747) | (3S)-4-(6-Amino-1,3-dimethylpyrazolo[3,4-d]pyrimidin-4-yl)-N-[6-(dimethylamino)-2-methylpyridin-3-yl]-3-methylpiperazine-1-carboxamide | 5 | 1.55 | 439.4 |

Example 41 (Method H)

(3S)-4-(6-Amino-1,3-dimethylpyrazolo[3,4-d]pyrimidin-4-yl)-N-(4-methoxyphenyl)-3-methylpiperazine-1-carboxamide To a stirred solution of Intermediate 12 (50 mg, 0.18 mmol) in DMF (2 mL), maintained at 0° C., was added DIPEA (1.14 mmol), followed by 4-methoxyphenyl isocyanate (0.38 mmol). The reaction mixture was stirred at r.t. for 15 minutes. The reaction mixture was then diluted with water and extracted with EtOAc. The organic layer was washed with water and brine, dried over sodium sulfate and concentrated in vacuo. The resulting crude material was purified by flash column chromatography on silica (100-200 mesh, 10% MeOH/DCM), to yield the title compound (0.07 g, 94%) as a white solid. LCMS (ES+) 411.3 $[M+H]^+$, RT 1.60 minutes (method 5).

Examples 42 to 44 (Method I)

To Intermediate 7 (0.05 g, 0.14 mmol) were added HATU (0.11 g, 0.28 mmol) and the appropriate carboxylic acid (0.18 mmol). The mixture was dissolved in DMF (5 mL) and DIPEA (0.11 mL, 0.64 mmol) was added. The mixture was stirred under nitrogen at r.t. for 72 h. The residue was concentrated in vacuo and purified by preparative HPLC, to yield the title compound as an off-white solid.

| Ex. | Acid | Name | LCMS Data Method | RT | [M + H]+ |
|---|---|---|---|---|---|
| 42 | 2,3-Dihydro-1-benzofuran-2-carboxylic acid | [(3S)-4-(6-Amino-1-methylpyrazolo-[3,4-d]pyrimidin-4-yl)-3-methyl-piperazin-1-yl[(2,3-dihydrobenzo-furan-2-yl)methanone | 2 | 2.03 | 394.8 |
| 43 | 2-Oxo-2-phenyl-acetic acid | 1-[(3S)-4-(6-Amino-1-methylpyrazolo-[3,4-d]pyrimidin-4-yl)-3-methyl-piperazin-1-yl]-2-phenylethane-1,2-dione | 2 | 1.57 | 380.8 |
| 44 | 5-Methoxybenzo-furan-2-carboxylic acid | [(3S)-4-(6-Amino-1-methylpyrazolo-[3,4-d]pyrimidin-4-yl)-3-methyl-piperazin-1-yl](5-methoxybenzofuran-2-yl)methanone | 2 | 1.78 | 422.8 |

Example 45

(3S)—N-(4-Methoxy-2-methylphenyl)-3-methyl-4-[1-methyl-6-(methylsulfanyl)-pyrazolo[3,4-d]pyrimidin-4-yl]piperazine-1-carboxamide To a solution of Intermediate 34 in DCM (3 mL) at r.t. were added DIPEA (218 μL, 1.3 mmol) and 4-methoxy-2-methylphenyl isocyanate (19 μL, 0.14 mmol). The reaction mixture was stirred overnight, then concentrated in vacuo. The residue was purified by silica gel chromatography (gradient 70% EtOAc/cyclohexane to 90% EtOAc/cyclohexane), to provide the title compound (51 mg, 87%) as a white solid. MS (m/z) 442 $[M+H]^+$.

Example 46

(3S)—N-(Indan-5-yl)-3-methyl-4-[1-methyl-6-(methylsulfonyl)pyrazolo[3,4-d]pyrimidin-4-yl]piperazine-1-carboxamide Intermediate 34 was dissolved in DCM (15 mL), then DIPEA (873 μL, 5.3 mmol) and 5-isocyanato-2,3-dihydro-1H-indene (80 μL, 0.55 mmol) were added. The reaction mixture was stirred overnight, then concentrated in vacuo. The residue was dissolved in DCM (3 mL), then MCPBA (70%; 267 mg, 1.1 mmol) was added at 0° C. The reaction mixture was continuously stirred for 2 h at r.t. To the solution was added a saturated aqueous solution of $Na_2SO_3$ (4 mL). The reaction mixture was partitioned between DCM and 2N aqueous NaOH solution. The organic layers were washed with brine, dried over magnesium sulfate and concentrated in vacuo. The residue was purified by silica gel chromatography (gradient 70% EtOAc/cyclohexane to 90% EtOAc/cyclohexane), to provide the title compound (201 mg, 81%) as a white solid. MS (m/z) 470 $[M+H]^+$.

Example 47

(3S)—N-(Indan-5-yl)-4-(6-methoxy-1-methylpyrazolo[3,4-d]pyrimidin-4-yl)-3-methyl-piperazine-1-carboxamide To a solution of Example 46 (50 mg, 0.11 mmol) in MeOH (2 mL) was added sodium methoxide (30 wt %; 18 μL, 1.2 mmol). The reaction mixture was stirred for 1 h at 60° C., then concentrated in vacuo. The residue was purified by silica gel chromatography (gradient 60% EtOAc/cyclohexane to 80% EtOAc/cyclohexane), to provide the title compound (25 mg, 56%) as a white solid. MS (m/z) 422 $[M+H]^+$.

Example 48

(3S)-4-(6-Cyano-1-methylpyrazolo[3,4-d]pyrimidin-4-yl)-N-(indan-5-yl)-3-methyl-piperazine-1-carboxamide To a solution of Example 46 (50 mg, 0.11 mmol) in DMF (2 mL) was added sodium cyanide (5 mg, 1.2 mmol). The reaction mixture was stirred overnight at 60° C., then concentrated in vacuo. The residue was purified by silica gel chromatography (gradient 70% EtOAc/cyclohexane to 90% EtOAc/cyclohexane), to provide the title compound (17 mg, 38%) as a white solid. MS (m/z) 417 $[M+H]^+$.

Example 49

(3S)-4-[6-(2-Hydroxyethylamino)-1-methylpyrazolo[3,4-d]pyrimidin-4-yl]-N-(4-methoxy-2-methylphenyl)-3-methylpiperazine-1-carboxamide To a solution of Intermediate 33 (100 mg, 0.26 mmol) in DCM (4 mL) at 0° C. was added MCPBA (70%; 133 mg, 0.54 mmol). The reaction mixture was continuously stirred for 2 h at r.t., then a saturated aqueous solution of $Na_2SO_3$ (4 mL) was added. The reaction mixture was partitioned between DCM and 2N aqueous NaOH solution. The organic layers were washed with brine, dried over magnesium sulfate and concentrated in vacuo. The residue was dissolved in 1,4-dioxane (2 mL) and $H_2O$ (2 mL), then 2-aminoethanol (79 μL, 1.3 mmol) was added. The reaction mixture was continuously stirred in a sealed vessel for 24 h at 100° C. The mixture was concentrated in vacuo. The residue was dissolved in DCM (2 mL) and TFA (2 mL). After 1 h at r.t., the reaction mixture was concentrated in vacuo. The resulting crude material was dissolved in DCM (4 mL) and DIPEA (437 μL, 2.6 mmol), then 4-methoxy-2-methylphenyl isocyanate (37 μL, 0.28 mmol) was added. The reaction mixture was stirred overnight at r.t., then concentrated in vacuo. The residue was purified by silica gel chromatography (gradient 4% 7N $NH_3$ in MeOH/EtOAc to 6% 7N $NH_3$ in MeOH/EtOAc) to provide the title compound (29 mg, 24%) as a white solid. MS (m/z) 455 $[M+H]^+$.

Example 50 (Method J)

(3S)-4-(6-Amino-1-methylpyrazolo[3,4-d]pyrimidin-4-yl)-3-methyl-N-[2-methyl-4-(trifluoromethoxy)phenyl]piperazine-1-carboxamide Intermediate 7 (2.38 g, 7.43 mmol) and Intermediate 38 (2.31 g, 7.42 mmol) were taken up in acetonitrile (150 mL) and DIPEA (2.91 g, 4.0 mL, 22.3 mmol) was added. The reaction mixture was stirred overnight, then concentrated in vacuo and partitioned between DCM and water. The organic layers were phase separated and concentrated in vacuo. The residue was purified by flash column chromatography on silica (Biotage SNAP 100 g, Isolera, gradient elution: 100% EtOAc to 20% MeOH/EtOAc) to yield the title compound (2.35 g, 68.2%) as a white solid. $\delta_H$ (DMSO-$d_6$) 8.20 (s, 1H), 7.93 (s, 1H), 7.30 (m, 1H), 7.18 (m, 2H), 6.19 (s, 2H), 4.60 (m, 2H), 4.04 (m, 2H), 3.71 (s, 3H), 3.39 (m, 2H), 3.16 (m, 1H), 2.21 (s, 3H), 1.28 (d, J 6.6 Hz, 3H). LCMS (ES+) $[M+H]^+$ 465.8, RT 1.96 minutes (method 2).

Examples 51 to 75

The following compounds were prepared via Method J utilising Intermediate 7 and the indicated carbamate intermediate.

| | | | LCMS Data | | |
|---|---|---|---|---|---|
| Ex. | Int. | Name | Method | RT | $[M + H]^+$ |
| 51 | 39 | (3S)-4-(6-Amino-1-methyl-1H-pyrazolo[3,4-d]-pyrimidin-4-yl)-N-[2-fluoro-4-(trifluoromethoxy)-phenyl]-3-methylpiperazine-1-carboxamide | 4 | 1.67 | 469 |
| 52 | 40 | (3S)-4-(6-Amino-1-methyl-1H-pyrazolo[3,4-d]-pyrimidin-4-yl)-N-[2-chloro-4-(trifluoromethoxy)-phenyl]-3-methylpiperazine-1-carboxamide | 4 | 1.79 | 485.6 |
| 53 | 41 | (3S)-4-(6-Amino-1-methyl-1H-pyrazolo[3,4-d]-pyrimidin-4-yl)-N-[3-methoxy-5-(trifluoromethyl)-phenyl]-3-methylpiperazine-1-carboxamide | 4 | 1.73 | 465.8 |
| 54 | 42 | (3S)-4-(6-Amino-1-methyl-1H-pyrazolo[3,4-d]-pyrimidin-4-yl)-N-(1-ethyl-1H-indazol-3-yl)-3-methyl-piperazine-1-carboxamide | 2 | 1.51 | 435.8 |
| 55 | 43 | (3S)-4-(6-Amino-1-methyl-1H-pyrazolo[3,4-d]-pyrimidin-4-yl)-N-[6-(difluoromethoxy)-2-methyl-pyridin-3-yl]-3-methylpiperazine-1-carboxamide | 2 | 1.60 | 448 |
| 56 | 44 | (3S)-4-(6-Amino-1-methyl-1H-pyrazolo[3,4-d]-pyrimidin-4-yl)-N-(6-ethoxy-5-fluoropyridin-3-yl)-3-methylpiperazine-1-carboxamide | 2 | 1.57 | 430.8 |

-continued

| Ex. | Int. | Name | LCMS Data Method | RT | [M + H]+ |
|---|---|---|---|---|---|
| 57 | 45 | (3S)-4-(6-Amino-1-methyl-1H-pyrazolo[3,4-d]-pyrimidin-4-yl)-N-(2-chloro-4-fluoro-5-methylphenyl)-3-methylpiperazine-1-carboxamide | 2 | 1.75 | 433.9 |
| 58 | 46 | (3S)-4-(6-Amino-1-methyl-1H-pyrazolo[3,4-d]-pyrimidin-4-yl)-N-(5-fluoro-6-methoxypyridin-3-yl)-3-methylpiperazine-1-carboxamide | 2 | 1.42 | 416.8 |
| 59 | 47 | (3S)-4-(6-Amino-1-methyl-1H-pyrazolo[3,4-d]-pyrimidin-4-yl)-N-(6-ethoxy-2-methylpyridin-3-yl)-3-methylpiperazine-1-carboxamide | 2 | 1.39 | 426.8 |
| 60 | 48 | (3S)-4-(6-Amino-1-methyl-1H-pyrazolo[3,4-d]-pyrimidin-4-yl)-3-methyl-N-[1-methyl-5-(trifluoro-methyl)-1H-indazol-3-yl]piperazine-1-carboxamide | 2 | 1.80 | 449.7 |
| 61 | 49 | (3S)-4-(6-Amino-1-methyl-1H-pyrazolo[3,4-d]-pyrimidin-4-yl)-N-(6-fluoro-1-methyl-1H-indazol-3-yl)-3-methylpiperazine-1-carboxamide | 2 | 1.49 | 439.8 |
| 62 | 50 | (3S)-4-(6-Amino-1-methyl-1H-pyrazolo[3,4-d]-pyrimidin-4-yl)-N-(5-fluoro-1-methyl-1H-indazol-3-yl)-3-methylpiperazine-1-carboxamide | 2 | 1.47 | 439.8 |
| 63 | 51 | (3S)-4-(6-Amino-1-methyl-1H-pyrazolo[3,4-d]-pyrimidin-4-yl)-N-(imidazo[1,2-a]pyridin-8-yl)-3-methylpiperazine-1-carboxamide | 2 | 1.13 | 407.44 |
| 64 | 52 | (3S)-4-(6-Amino-1-methyl-1H-pyrazolo[3,4-d]-pyrimidin-4-yl)-3-methyl-N-(5-methyl-1,2-oxazol-3-yl)-piperazine-1-carboxamide | 2 | 1.10 | 372.4 |
| 65 | 53 | (3S)-4-(6-Amino-1-methyl-1H-pyrazolo[3,4-d]-pyrimidin-4-yl)-N-(1,2-benzoxazol-3-yl)-3-methyl-piperazine-1-carboxamide | 2 | 1.20 | 408.43 |
| 66 | 54 | (3S)-4-(6-Amino-1-methyl-1H-pyrazolo[3,4-d]-pyrimidin-4-yl)-3-methyl-N-(1-methyl-1H-indazol-3-yl)piperazine-1-carboxamide | 2 | 1.16 | 421.47 |
| 67 | 55 | (3S)-4-(6-Amino-1-methyl-1H-pyrazolo[3,4-d]-pyrimidin-4-yl)-N-(6-cyano-2-methylpyridin-3-yl)-3-methylpiperazine-1-carboxamide | 2 | 1.13 | 407.44 |
| 68 | 56 | (3S)-4-(6-Amino-1-methyl-1H-pyrazolo[3,4-d]-pyrimidin-4-yl)-3-methyl-N-[2 methyl-4-(methyl-sulfonyl)phenyl]piperazine-1-carboxamide | 2 | 1.11 | 459.84 |
| 69 | 57 | (3S)-4-(6-Amino-1-methyl-1H-pyrazolo[3,4-d]-pyrimidin-4-yl)-N-[6-(difluoromethoxy)-4-methyl-pyridin-3-yl]-3-methylpiperazine-1-carboxamide | 2 | 1.24 | 448.44 |
| 70 | 58 | (3S)-4-(6-Amino-1-methyl-1H-pyrazolo[3,4-d]-pyrimidin-4-yl)-N-(6-methoxy-5-methylpyridin-3-yl)-3-methylpiperazine-1-carboxamide | 2 | 1.18 | 412.46 |
| 71 | 59 | (3S)-4-(6-Amino-1-methyl-1H-pyrazolo[3,4-d]-pyrimidin-4-yl)-N-(6-methoxy-4-methylpyridin-3-yl)-3-methylpiperazine-1-carboxamide | 2 | 1.11 | 412.46 |
| 72 | 60 | (3S)-4-(6-Amino-1-methyl-1H-pyrazolo[3,4-d]-pyrimidin-4-yl)-N-(5-methoxy-2-methylphenyl)-3-methylpiperazine-1-carboxamide | 2 | 1.21 | 411.47 |
| 73 | 61 | (3S)-4-(6-Amino-1-methyl-1H-pyrazolo[3,4-d]-pyrimidin-4-yl)-N-(3-chloro-4-methylphenyl)-3-methyl-piperazine-1-carboxamide | 2 | 1.35 | 415.89 |
| 74 | 62 | (3S)-4-(6-Amino-1-methyl-1H-pyrazolo[3,4-d]-pyrimidin-4-yl)-N-(2,5-dichlorophenyl)-3-methyl-piperazine-1-carboxamide | 2 | 1.36 | 436.31 |
| 75 | 63 | (3S)-4-(6-Amino-1-methyl-1H-pyrazolo[3,4-d]-pyrimidin-4-yl)-N-(4-cyano-2-methylphenyl)-3-methyl-piperazine-1-carboxamide | 2 | 1.19 | 406.46 |

Example 76

(3S)-4-(6-Amino-1-methylpyrazolo[3,4-d]pyrimidin-4-yl)-3-ethyl-N-(6-methoxy-2-methylpyridin-3-yl) piperazine-1-carboxamide Intermediate 37 (0.4 g, 1 mmol) in acetonitrile (10 mL) and DIPEA (0.5 g, 0.7 mL, 4 mmol) were treated with Intermediate 24 (0.3 g, 1 mmol). The reaction mixture was stirred at room temperature overnight, then concentrated in vacuo. The residue was partitioned between water and DCM. The organic layers were phase separated, and the residual solid was triturated with diethyl ether, to yield the title compound (0.408 g, 80%) as a white powder. $\delta_H$ (DMSO-$d_6$) 8.15 (s, 1H), 7.92 (s, 1H), 7.42 (d, J 8.6 Hz, 1H), 6.60 (d, J 8.5 Hz, 1H), 6.18 (s, 2H), 4.65 (m, 2H), 4.10 (m, 2H), 3.72 (s, 3H), 3.65 (s, 3H), 3.15 (m, 3H), 2.28 (s, 3H), 1.69 (m, 2H), 1.66 (t, J 7.3 Hz, 3H). LCMS (ES+) [M+H]+ 426, RT 1.38 minutes (method 2).

Example 77

(3S)-4-(6-Amino-1-methylpyrazolo[3,4-d]pyrimidin-4-yl)-N-(6-ethoxy-2-methylpyridin-3-yl)-3-ethylpiperazine-1-carboxamide Intermediate 37 (0.043 g, 0.16 mmol) was dissolved in acetonitrile (5 mL) and Intermediate 47 (45 mg, 0.16 mmol)

was added, followed by DIPEA (0.042 g, 0.33 mmol). The reaction mixture was stirred at 70° C. for 1 h, then concentrated. The residue was purified by HPLC at basic pH to yield the title compound (0.035 g, 48.6%) as a freeze-dried white solid. $\delta_H$ (DMSO-$d_6$) 8.14 (s, 1H), 7.93 (s, 1H), 7.41 (d, J 8.5 Hz, 1H), 6.58 (d, J 8.5 Hz, 1H), 6.18 (s, 2H), 4.52 (m, 2H), 4.28 (q, J 7.0 Hz, 2H), 4.12 (m, 2H), 3.71 (s, 3H), 3.15 (m, 3H), 2.27 (s, 3H), 1.69 (m, 2H), 1.31 (m, 3H), 0.90 (m, 3H). LCMS (ES+) $[M+H]^+$ 440.5, RT 1.52 minutes (method 2).

Example 78

(3S)-4-(6-Amino-1-methylpyrazolo[3,4-d]pyrimidin-4-yl)-N-(2,6-dimethoxypyridin-3-yl)-3-ethylpiperazine-1-carboxamide Intermediate 37 (0.20 g, 0.60 mmol) and Intermediate 64 (0.16 g, 0.58 mmol) in acetonitrile (20 mL) were treated with DIPEA (0.2 g, 0.3 mL, 2 mmol). The reaction mixture was stirred over the weekend at room temperature, then concentrated in vacuo and partitioned between DCM and water. The organic layers were phase separated and concentrated in vacuo. The residue was purified by flash column chromatography on silica (Biotage SNAP 50 g, Isolera, gradient elution: 100% EtOAc to 30% MeOH/EtOAc) to yield the title compound (0.099 g, 37%) as a white solid. $\delta_H$ (DMSO-$d_6$) 7.91 (s, 1H), 7.79 (s, 1H), 7.63 (d, J 8.3 Hz, 1H), 6.34 (d, J 8.2 Hz, 1H), 6.17 (s, 2H), 4.61 (m, 2H), 4.05 (m, 2H), 3.86 (d, J 11.9 Hz, 6H), 3.70 (s, 3H), 3.10 (m, 3H), 1.68 (m, 2H), 0.88 (t, J 7.4 Hz, 3H). LCMS (ES+) $[M+H]^+$ 442.5, RT 1.63 minutes (method 2).

Example 79

(3S)-4-(6-Amino-1-methylpyrazolo[3,4-d]pyrimidin-4-yl)-3-ethyl-N-(4-methoxy-2-methylphenyl)piperazine-1-carboxamide Intermediate 37 (0.20 g, 0.60 mmol) and Intermediate 25 (0.15 g, 0.58 mmol) in acetonitrile (8 mL) with DIPEA (0.23 g, 1.8 mmol) were heated at 40° C. for 2 h. The reaction mixture was cooled, then stirred at room temperature overnight. A slurry had formed, to which was added water. The solid was collected by filtration, and washed further with water, then with diethyl ether, to yield the title compound (0.119 g, 47%) as a white powder. $\delta_H$ (DMSO-$d_6$) 8.00 (s, 1H), 7.92 (s, 1H), 7.02 (d, J 8.6 Hz, 1H), 6.77 (m, 1H), 6.70 (dd, J 8.5, 2.9 Hz, 1H), 6.17 (s, 2H), 4.65 (m, 2H), 4.11 (m, 2H), 3.71 (m, 6H), 3.12 (m, 3H), 2.14 (s, 3H), 1.68 (m, 2H), 0.89 (t, J 7.4 Hz, 3H). LCMS (ES+) $[M+H]^+$ 425.8, RT 1.55 minutes (method 2).

Example 80

(3S)-4-(6-Amino-1-methylpyrazolo[3,4-d]pyrimidin-4-yl)-N-[6-(3,3-difluoroazetidin-1-yl)-2-methylpyridin-3-yl]-3-ethylpiperazine-1-carboxamide Intermediate 37 (0.20 g, 0.60 mmol) and Intermediate 23 (0.19 g, 0.60 mmol) in acetonitrile (8 mL) were treated with DIPEA (0.23 g, 1.8 mmol) and stirred at 40° C. for 2 h. The reaction mixture was cooled and stirred at room temperature overnight, then concentrated in vacuo, and partitioned between DCM and water. The organic layers were phase separated and concentrated in vacuo. The residue was purified by flash column chromatography on silica (Biotage SNAP 50 g, Isolera, gradient elution: 100% EtOAc to 40% MeOH/EtOAc) to yield the title compound (0.15 g, 52%) as a white solid. $\delta_H$ (DMSO-$d_6$) 8.08 (s, 1H), 7.91 (s, 1H), 7.34 (d, J 8.5 Hz, 1H), 6.38 (d, J 8.5 Hz, 1H), 6.17 (s, 2H), 4.50 (br s, 2H), 4.32 (t, J 12.5 Hz, 4H), 4.03 (m, 2H), 3.70 (s, 3H), 3.20 (m, 3H), 2.23 (s, 3H), 1.70 (m, 2H), 0.82 (t, J 7.4 Hz, 3H). LCMS (ES+) $[M+H]^+$ 487.8, RT 1.61 minutes (method 2).

Example 81

(3S)-4-(6-Amino-1-methylpyrazolo[3,4-d]pyrimidin-4-yl)-3-ethyl-N-[2-methyl-4-(trifluoromethoxy)phenyl]piperazine-1-carboxamide Intermediate 37 (0.15 g, 0.45 mmol) and Intermediate 38 (0.14 g, 0.45 mmol) in acetonitrile (20 mL) with DIPEA (0.18 g, 0.25 mL, 1.4 mmol) were stirred overnight. The reaction mixture was concentrated in vacuo and partitioned between DCM and water. The organic layers were phase separated and concentrated in vacuo. The residue was purified by flash column chromatography on silica (Biotage SNAP 50 g, Isolera, gradient elution: 100% EtOAc to 20% MeOH/EtOAc) to yield the title compound (0.038 g, 18%) as a white solid. $\delta_H$ (DMSO-$d_6$) 8.20 (s, 1H), 7.93 (s, 1H), 7.30 (m, 1H), 7.22 (dd, J 2.1, 1.0 Hz, 1H), 7.14 (m, 1H), 6.19 (s, 2H), 4.64 (m, 2H), 4.10 (m, 1H), 3.98 (m, 1H), 3.71 (s, 3H), 3.35 (m, 2H), 3.16 (m, 1H), 2.21 (s, 3H), 1.61 (m, 2H), 0.91 (t, J 7.0 Hz, 3H). LCMS (ES+) $[M+H]^+$ 479.8, RT 2.07 minutes (method 2).

Example 82

(3S)-4-(6-Amino-1-methylpyrazolo[3,4-d]pyrimidin-4-yl)-3-ethyl-N-(4-methoxy-3-methylphenyl)piperazine-1-carboxamide Intermediate 37 (0.05 g, 0.1679 mmol) was dissolved in acetonitrile (5 mL) and Intermediate 65 (0.047 g, 0.1847 mmol) was added, followed by DIPEA (0.065 g, 0.50 mmol). The reaction mixture was stirred at 70° C. for 1 h, then concentrated in vacuo. The residue was purified by flash column chromatography on silica (Biotage SNAP 50 g, Isolera, gradient elution: 100% DCM to 7% MeOH/DCM) to yield the title compound (0.071 g, quantitative) as a white solid. $\delta_H$ (DMSO-$d_6$) 8.34 (s, 1H), 7.93 (s, 1H), 7.22 (m, 2H), 6.82 (m, 1H), 6.18 (s, 2H), 4.56 (m, 2H), 4.12 (m, 2H), 3.73 (m, 6H), 3.11 (m, 3H), 2.12 (s, 3H), 1.65 (m, 2H), 0.87 (t, J 7.4 Hz, 3H). LCMS (ES+) $[M+H]^+$ 425.8, RT 1.48 minutes (method 4).

Examples 83 to 100

The following compounds were prepared via Method J utilising Intermediate 37 and the indicated carbamate intermediate.

| Ex. | Int. | Name | LCMS Data Method | RT | [M + H]+ |
|---|---|---|---|---|---|
| 83 | 53 | (3S)-4-(6-Amino-1-methyl-1H-pyrazolo[3,4-d]-pyrimidin-4-yl)-N-(1,2-benzoxazol-3-yl)-3-ethyl-piperazine-1-carboxamide | 6 | 1.26 | 422.4 |
| 84 | 54 | (3S)-4-(6-Amino-1-methyl-1H-pyrazolo[3,4-d]-pyrimidin-4-yl)-3-ethyl-N-(1-methyl-1H indazol-3-yl)-piperazine-1-carboxamide | 6 | 1.22 | 435.5 |
| 85 | 57 | (3S)-4-(6-Amino-1-methyl-1H-pyrazolo[3,4-d]-pyrimidin-4-yl)-N-[6-(difluoromethoxy)-4-methyl-pyridin-3-yl]-3-ethylpiperazine-1-carboxamide | 6 | 1.29 | 462.4 |
| 86 | 58 | (3S)-4-(6-Amino-1-methyl-1H-pyrazolo[3,4-d]-pyrimidin-4-yl)-3-ethyl-N-(6-methoxy-5-methyl-pyridin-3-yl)piperazine-1-carboxamide | 6 | 1.23 | 426.47 |
| 87 | 56 | (3S)-4-(6-Amino-1-methyl-1H-pyrazolo[3,4-d]-pyrimidin-4-yl)-3-ethyl-N-[2-methyl-4-(methyl-sulfonyl)phenyl]piperazine-1-carboxamide | 6 | 1.15 | 473.5 |
| 88 | 59 | (3S)-4-(6-Amino-1-methyl-1H-pyrazolo[3,4-d]-pyrimidin-4-yl)-3-ethyl-N-(6-methoxy-4-methyl-pyridin-3-yl)piperazine-1-carboxamide | 6 | 1.15 | 426.5 |
| 89 | 48 | (3S)-4-(6-Amino-1-methyl-1H-pyrazolo[3,4-d]-pyrimidin-4-yl)-3-ethyl-N-[1-methyl-5-(trifluoro-methyl)-1H-indazol-3-yl]piperazine-1-carboxamide | 6 | 1.35 | 503.5 |
| 90 | 49 | (3S)-4-(6-Amino-1-methyl-1H-pyrazolo[3,4-d]-pyrimidin-4-yl)-3-ethyl-N-(6-fluoro-1-methyl-1H-indazol-3-yl)piperazine-1-carboxamide | 6 | 1.23 | 453.5 |
| 91 | 50 | (3S)-4-(6-Amino-1-methyl-1H-pyrazolo[3,4-d]-pyrimidin-4-yl)-3-ethyl-N-(5-fluoro-1-methyl-1H-indazol-3-3,1)piperazine-1-carboxamide | 6 | 1.23 | 453.5 |
| 92 | 43 | (3S)-4-(6-Amino-1-methyl-1H-pyrazolo[3,4-d]-pyrimidin-4-yl)-N-[6-(difluoromethoxy)-2-methyl-pyridin-3-yl]-3-ethylpiperazine-1-carboxamide | 6 | 1.29 | 462.5 |
| 93 | 51 | (3S)-4-(6-Amino-1-methyl-1H-pyrazolo[3,4-d]-pyrimidin-4-yl)-3-ethyl-N-(imidazo[1,2-a]pyridin-8-yl)piperazine-1-carboxamide | 6 | 1.18 | 421.5 |
| 94 | 44 | (3S)-4-(6-Amino-1-methyl-1H-pyrazolo[3,4-d]-pyrimidin-4-yl)-N-(6-ethoxy-5-fluoropyridin-3-yl)-3-ethylpiperazine-1-carboxamide | 6 | 1.29 | 444.4 |
| 95 | 45 | (3S)-4-(6-Amino-1-methyl-1H-pyrazolo[3,4-d]-pyrimidin-4-yl)-N-(2-chloro-4-fluoro-5-methyl-phenyl)-3-ethylpiperazine-1-carboxamide | 6 | 1.39 | 447.9 |
| 96 | 46 | (3S)-4-(6-Amino-1-methyl-1H-pyrazolo[3,4-d]-pyrimidin-4-yl)-3-ethyl-N-(5-fluoro-6-methoxy-pyridin-3-yl)piperazine-1-carboxamide | 6 | 1.25 | 430.4 |
| 97 | 55 | (3S)-4-(6-Amino-1-methyl-1H-pyrazolo[3,4-d]-pyrimidin-4-yl)-N-(6-cyano-2-methylpyridin-3-yl)-3-ethylpiperazine-1-carboxamide | 6 | 1.19 | 421.5 |
| 98 | 63 | (3S)-4-(6-Amino-1-methyl-1H-pyrazolo[3,4-d]-pyrimidin-4-yl)-N-(4-cyano-2-methylphenyl)-3-ethyl-piperazine-1-carboxamide | 6 | 1.24 | 420.5 |
| 99 | 66 | (3S)-4-(6-Amino-1-methyl-1H-pyrazolo[3,4-d]-pyrimidin-4-yl)-N-[4-(difluoromethoxy)-2-methyl-phenyl]-3-ethylpiperazine-1-carboxamide | 6 | 1.31 | 461.5 |
| 100 | 71 | (3S)-4-(6-Amino-1-methyl-1H-pyrazolo[3,4-d]-pyrimidin-4-yl)-N-[5-(dimethylamino)-3-methyl-pyrazin-2-yl]-3-ethylpiperazine-1-carboxamide | 6 | 1.17 | 440.5 |

Examples 101 to 106

The following compounds were prepared via Method F utilising Intermediate 7 and the appropriate amine.

| Ex. | Name | LCMS Data Method | RT | [M + H]+ |
|---|---|---|---|---|
| 101 | (3S)-4-(6-Amino-1-methyl-1H-pyrazolo[3,4-d]pyrimidin-4-yl)-3-methyl-N-(1-methyl-1H-indazol-4-yl)-piperazine-1-carboxamide | 4 | 1.25 | 421.8 |
| 102 | (3S)-4-(6-Amino-1-methyl-1H-pyrazolo[3,4-d]pyrimidin-4-yl)-N-(2-methoxy-6-methylpyridin-3-yl)-3-methylpiperazine-1-carboxamide | 2 | 1.57 | 412.5 |
| 103 | (3S)-4-(6-Amino-1-methyl-1H-pyrazolo[3,4-d]pyrimidin-4-yl)-3-methyl-N-(1-methyl-1H-indol-4-yl)piperazine-1-carboxamide | 2 | 1.53 | 420.8 |

-continued

| Ex. | Name | LCMS Data Method | RT | [M + H]+ |
|---|---|---|---|---|
| 104 | (3S)-4-(6-Amino-1-methyl-1H-pyrazolo[3,4-d]pyrimidin-4-yl)-3-methyl-N-(1-methyl-1H-benzotriazol-4-yl)piperazine-1-carboxamide | 2 | 1.35 | 422.8 |
| 105 | (3S)-4-(6-Amino-1-methyl-1H-pyrazolo[3,4-d]pyrimidin-4-yl)-N-(imidazo[1,2-a]pyridin-5-yl)-3-methylpiperazine-1-carboxamide | 2 | 1.02 | 407.44 |
| 106 | (3S)-4-(6-Amino-1-methyl-1H-pyrazolo[3,4-d]pyrimidin-4-yl)-N-(imidazo[1,2-a]pyridin-3-yl)-3-methylpiperazine-1-carboxamide | 2 | 1.03 | 407.44 |

Examples 107 to 119

The following compounds were prepared via Method G utilising the stated piperazine intermediate and the appropriate amine.

The amine utilised for Examples 112 and 118 was Intermediate 72. The amine utilised for Example 113 was Intermediate 69.

| Ex. | Int. | Name | LCMS Data Method | RT | [M + H]+ |
|---|---|---|---|---|---|
| 107 | 7 | (3S)-4-(6-Amino-1-methyl-1H-pyrazolo[3,4-d]-pyrimidin-4-yl)-3-methyl-N-(1-methyl-1H-pyrazolo-[4,3-c]pyridin-4-yl)piperazine-1-carboxamide | 6 | 1.10 | 422.4 |
| 108 | 7 | (3S)-4-(6-Amino-1-methyl-1H-pyrazolo[3,4-d]-pyrimidin-4-yl)-N-(3-chloro-5-methoxypyridin-2-yl)-3-methylpiperazine-1-carboxamide | 6 | 1.11 | 432.8 |
| 109 | 7 | (3S)-4-(6-Amino-1-methyl-1H-pyrazolo[3,4-d]-pyrimidin-4-yl)-N-(2-chloro-4-methoxyphenyl)-3-methylpiperazine-1-carboxamide | 6 | 1.20 | 431.8 |
| 110 | 7 | (3S)-4-(6-Amino-1-methyl-1H-pyrazolo[3,4-d]-pyrimidin-4-yl)-N-[6-methoxy-2-(trifluoromethyl)-pyridin-3-yl]-3-methylpiperazine-1-carboxamide | 6 | 1.25 | 466.4 |
| 111 | 7 | (3S)-4-(6-Amino-1-methyl-1H-pyrazolo[3,4-d]-pyrimidin-4-yl)-N-(6-fluoro-1-methyl-1H-indazol-4-yl)-3-methylpiperazine-1-carboxamide | 6 | 1.19 | 439.4 |
| 112 | 7 | (3S)-4-(6-Amino-1-methyl-1H-pyrazolo[3,4-d]-pyrimidin-4-yl)-N-(2-ethyl-6-methoxypyridin-3-yl)-3-methylpiperazine-1-carboxamide | 6 | 1.18 | 426.5 |
| 113 | 7 | (3S)-4-(6-Amino-1-methyl-1H-pyrazolo[3,4-d]-pyrimidin-4-yl)-N-[5-(dimethylamino)-3-methyl-pyrazin-2-yl]-3-methylpiperazine-1-carboxamide | 6 | 1.10 | 426.5 |
| 114 | 37 | (3S)-4-(6-Amino-1-methyl-1H-pyrazolo[3,4-d]-pyrimidin-4-yl)-3-ethyl-N-(1-methyl-1H-pyrazolo[4,3-c]pyridin-4-yl)piperazine-1-carboxamide | 6 | 1.53 | 460.4 |
| 115 | 37 | (3S)-4-(6-Amino-1-methyl-1H-pyrazolo[3,4-d]-pyrimidin-4-yl)-N-(2-chloro-4-methoxyphenyl)-3-ethylpiperazine-1-carboxamide | 6 | 1.25 | 445.9 |
| 116 | 37 | (3S)-4-(6-Amino-1-methyl-1H-pyrazolo[3,4-d]-pyrimidin-4-yl)-3-ethyl-N-(6-fluoro-1-methyl-1H-indazol-4-yl)piperazine-1-carboxamide | 6 | 1.24 | 453.5 |
| 117 | 37 | (3S)-4-(6-Amino-1-methyl-1H-pyrazolo[3,4-d]-pyrimidin-4-yl)-3-ethyl-N-[6-methoxy-2-(trifluoro-methyl)pyridin-3-yl]piperazine-1-carboxamide | 6 | 1.3 | 480.5 |
| 118 | 37 | (3S)-4-(6-Amino-1-methyl-1H-pyrazolo[3,4-d]-pyrimidin-4-yl)-3-ethyl-N-(2-ethyl-6-methoxypyridin-3-yl)piperazine-1-carboxamide | 6 | 1.23 | 440.5 |
| 119 | 12 | (3S)-4-(6-Amino-1,3-dimethyl-1H-pyrazolo[3,4-d]-pyrimidin-4-yl)-N-[2-(dimethylamino)-4-methyl-pyrimidin-5-yl]-3-methylpiperazine-1-carboxamide | 6 | 1.13 | 440.5 |

Example 120

4-(6-Amino-1-methylpyrazolo[3,4-d]pyrimidin-4-yl)-3-(2-hydroxyethyl)-N-[2-methyl-4-(trifluoromethoxy)phenyl]piperazine-1-carboxamide Intermediate 73 (0.17 g, 0.49 mmol) and Intermediate 38 (0.15 g, 0.48 mmol) in acetonitrile (10 mL) and DIPEA (0.19 g, 0.26 mL, 1.5 mmol) were stirred at room temperature overnight. The reaction mixture was concentrated in vacuo, then partitioned between DCM and water. The organic layers were phase separated and concentrated in vacuo. The residue was purified by flash column chromatography on silica (Biotage SNAP 50 g, Isolera, gradient elution: 100% EtOAc to 20% MeOH/EtOAc) to yield the title compound (0.12 g, 50%) as a white solid. $\delta_H$ (DMSO-$d_6$) 8.23 (s, 1H), 8.06 (m, 1H), 7.31 (m, 1H), 7.21 (m, 1H), 7.13 (m, 1H), 6.19 (d, J 0.2 Hz, 2H), 4.75 (m, 3H), 4.09 (m, 2H), 3.70 (s, 3H), 3.54 (m, 2H), 3.15 (m, 3H), 2.20 (s, 3H), 1.81 (m, 2H). LCMS (ES+) $[M+H]^+$ 495.8, RT 1.76 minutes (method 4).

Example 121

(3R)-4-(6-Amino-1-methyl-1H-pyrazolo[3,4-d]pyrimidin-4-yl)-3-(hydroxymethyl)-N-[2-methyl-4-(trifluoromethoxy)phenyl]piperazine-1-carboxamide Intermediate 15 (0.20 g, 0.59 mmol) and Intermediate 38 (0.19 g, 0.61 mmol) in acetonitrile (10 mL) and DIPEA (0.23 g, 0.32 mL, 1.8 mmol) were stirred at room temperature for 6 h. The reaction mixture was concentrated in vacuo, then partitioned between DCM and water. The organic layers were phase separated and concentrated in vacuo. The residue was purified by flash column chromatography on silica (Biotage SNAP 50 g, Isolera, gradient elution: 100% EtOAc to 30% MeOH/EtOAc) to yield the title compound (0.09 g, 33%) as a white solid. $\delta_H$ (DMSO-$d_6$) 8.12 (s, 1H), 7.91 (s, 1H), 7.36 (d, J 8.7 Hz, 1H), 7.19 (m, 1H), 7.15 (m, 1H), 6.18 (s, 2H), 5.07 (br s, 1H), 4.49 (br s, 2H), 4.15 (m, 1H), 3.95 (m, 1H), 3.70 (s, 3H), 3.61 (m, 3H), 3.31 (m, 1H), 3.12 (m, 1H), 2.21 (s, 3H). LCMS (ES+) $[M-H]^-$ 479.0, RT 1.55 minutes (method 4).

Examples 122 to 138

The following examples were prepared via Method J utilising the indicated carbamate and piperazine intermediates.

| | | | LCMS Data | | |
|---|---|---|---|---|---|
| Ex. | Int. | Name | Method | RT | $[M + H]^+$ |
| 122 | 24 & 81 | (3S)-4-(6-Amino-1-methyl-1H-pyrazolo[3,4-d]-pyrimidin-4-yl)-N-(6-methoxy-2-methylpyridin-3-yl-3-(propan-2-yl)piperazine-1-carboxamide | 6 | 1.21 | 440.5 |
| 123 | 24 & 82 | (3S)-4-(6-Amino-1-methyl-1H-pyrazolo[3,4-d]-pyrimidin-4-yl)-N-(6-methoxy-2-methylpyridin-3-yl)-3-(2-methylpropyl)piperazine-1-carboxamide | 6 | 1.28 | 454.5 |
| 124 | 24 & 78 | 4-(6-Amino-1-methyl-1H-pyrazolo[3,4-d]-pyrimidin-4-yl)-N-(6-methoxy-2-methylpyridin-3-yl)-3-(2,2,2-trifluoroethyl)piperazine-1-carboxamide | 6 | 1.21 | 480.5 |
| 125 | 51 & 78 | 4-(6-Amino-1-methyl-1H-pyrazolo[3,4-d]-pyrimidin-4-yl)-N-(imidazo[1,2-a]pyridin-8-yl)-3-(2,2,2-trifluoroethyl)piperazine-1-carboxamide | 6 | 1.23 | 575.4 |
| 126 | 42 & 76 | (3S,5S)-4-(6-Amino-1-methyl-1H-pyrazolo[3,4-d]-pyrimidin-4-yl)-N-(1-ethyl-1H-indazol-3-yl)-3,5-dimethylpiperazine-1-carboxamide | 6 | 1.25 | 449.5 |
| 127 | 54 & 76 | (3S,5S)-4-(6-Amino-1-methyl-1H-pyrazolo[3,4-d]-pyrimidin-4-yl)-3,5-dimethyl-N-(1-methyl-1H-indazol-3-yl)piperazine-1-carboxamide | 6 | 1.2 | 435.5 |
| 128 | 70 & 76 | (3S,5S)-4-(6-Amino-1-methyl-1H-pyrazolo[3,4-d]-pyrimidin-4-yl)-N-[5-(dimethylamino)-3-methyl-pyrazin-2-yl]-3,5-dimethylpiperazine-1-carboxamide | 6 | 1.14 | 440.5 |
| 129 | 51 & 76 | (3S,5S)-4-(6-Amino-1-methyl-1H-pyrazolo[3,4-d]-pyrimidin-4-yl)-N-(imidazo[1,2-a]pyridin-8-yl)-3,5-dimethylpiperazine-1-carboxamide | 6 | 1.17 | 421.5 |
| 130 | 38 & 76 | (3S,5S)-4-(6-Amino-1-methyl-1H-pyrazolo[3,4-d]-pyrimidin-4-yl)-3,5-dimethyl-N-[2-methyl-4-(trifluoromethoxy)phenyl]piperazine-1-carboxamide | 6 | 1.39 | 479.5 |
| 131 | 24 & 76 | (3S,5S)-4-(6-Amino-1-methyl-1H-pyrazolo[3,4-d]-pyrimidin-4-yl)-N-(6-methoxy-2-methylpyridin-3-yl)-3,5-dimethylpiperazine-1-carboxamide | 6 | 1.13 | 426.5 |
| 132 | 24 & 80 | 4-(6-Amino-1-methyl-1H-pyrazolo[3,4-d]-pyrimidin-4-yl)-N-(6-methoxy-2-methylpyridin-3-yl)-3-(trifluoromethyl)piperazine-1-carboxamide | 6 | 1.18 | 466.4 |
| 133 | 25 & 80 | 4-(6-Amino-1-methyl-1H-pyrazolo[3,4-d]-pyrimidin-4-yl)-N-(4-methoxy-2-methylphenyl)-3-(trifluoromethyl)piperazine-1-carboxamide | 6 | 1.25 | 465.4 |
| 134 | 49 & 12 | (3S)-4-(6-Amino-1,3-dimethyl-1H-pyrazolo[3,4-d]-pyrimidin-4-yl)-N-(6-fluoro-1-methyl-1H-indazol-3-yl)-3-methylpiperazine-1-carboxamide | 6 | 1.22 | 453.5 |
| 135 | 50 & 12 | (3S)-4-(6-Amino-1,3-dimethyl-1H-pyrazolo[3,4-d]-pyrimidin-4-yl)-N-(5-fluoro-1-methyl-1H-indazol-3-yl)-3-methylpiperazine-1-carboxamide | 6 | 1.22 | 453.5 |
| 136 | 43 & 12 | (3S)-4-(6-Amino-1,3-dimethyl-1H-pyrazolo[3,4-d]-pyrimidin-4-yl)-N-[6-(difluoromethoxy)-2-methyl-pyridin-3-yl]-3-methylpiperazine-1-carboxamide | 6 | 1.28 | 462.4 |
| 137 | 70 & 12 | (3S)-4-(6-Amino-1,3-dimethyl-1H-pyrazolo[3,4-d]-pyrimidin-4-yl)-N-[5-(dimethylamino)-3-methyl-pyrazin-2-yl]-3-methylpiperazine-1-carboxamide | 6 | 1.14 | 439.5 |

-continued

| Ex. | Int. | Name | LCMS Data Method | RT | [M + H]+ |
|---|---|---|---|---|---|
| 138 | 66 & 12 | (3S)-4-(6-Amino-1,3-dimethyl-1H-pyrazolo[3,4-d]-pyrimidin-4-yl)-N-[4-(difluoromethoxy)-2-methyl-phenyl]-3-methylpiperazine-1-carboxamide | 6 | 1.28 | 460.5 |

Example 139

(3S)-4-[6-Amino-3-(4-fluorophenyl)-1-methylpyrazolo[3,4-d]pyrimidin-4-yl]-N-(4-methoxy-2-methylphenyl)-3-methylpiperazine-1-carboxamide Prepared via Method B using Intermediate 88 (0.22 mmol) and 2-methyl-4-methoxyphenyl isocyanate (36 μL, 0.26 mmol). The title compound (107 mg, 96%) was obtained as a white solid. $^{13}C$ NMR δ ($CDCl_3$, 75 MHz) 161.2 (d, $J_{F,C}$ 246.7 Hz, phenyl), 161.1 (C-4), 160.7 (C-2), 158.3 (C-7a), 157.1 (C═O), 156.3 (phenyl), 143.4 (phenyl), 133.9 (phenyl), 130.8 (C-5), 130.1 (d, $J_{F,C}$ 8.0 Hz, phenyl), 129.6 (phenyl), 126.7 (phenyl), 115.8 (d, $J_{F,C}$ 6.9 Hz, phenyl), 115.6 (phenyl), 111.6 (phenyl), 95.6 (C-4a), 55.4 ($OCH_3$), 50.3 ($NCH_2$), 47.8 ($NCH_2$), 43.6 ($NCH_2$), 43.4 ($NCH_2$), 33.6 ($NCH_3$), 18.2 (Me), 14.7 (Me). MS (m/z) 505 $[M+H]^+$.

Example 140

(3S)-4-[6-Amino-1-methyl-3-(pyridin-3-yl)pyrazolo[3,4-d]pyrimidin-4-yl]-N-(4-methoxy-2-methylphenyl)-3-methylpiperazine-1-carboxamide Prepared via Method B using Intermediate 89 (0.195 mmol) and 2-methyl-4-methoxyphenyl isocyanate (36 μL, 0.26 mmol). The title compound (78 mg, 82%) was obtained as a white solid. $^{13}C$ NMR δ ($CDCl_3$, 75 MHz) 161.1 (C-4), 160.9 (C-2), 158.5 (C-7a), 157.1 (C═O), 156.3 (phenyl), 149.5 (py), 149.4 (py), 141.0 (py), 135.2 (py), 133.9 (phenyl), 130.7 (C-5), 129.6 (phenyl), 126.7 (phenyl), 123.6 (py), 115.8 (phenyl), 111.6 (phenyl), 95.8 (C-4a), 55.4 (OMe), 50.6 ($NCH_2$), 47.7 ($NCH_2$), 43.5 ($NCH_2$), 33.7 ($NCH_3$), 18.2 (Me), 14.7 (Me). MS (m/z) 488 $[M+H]^+$.

The invention claimed is:

1. A compound represented by formula (IA), or a pharmaceutically acceptable salt or solvate thereof:

(IA)

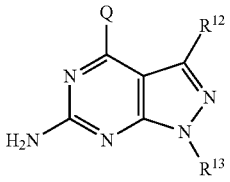

wherein $R^{12}$ represents hydrogen, trifluoromethyl or $C_{1-6}$ alkyl;

Q is (Qa)

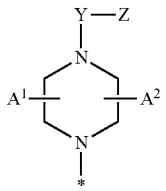

in which the asterisk (*) represents the point of attachment to the remainder of the molecule;

Y represents —C(O)—, —C(O)N($R^4$)— or —C(O)C(O)—;

Z represents $C_{3-7}$ cycloalkyl, $C_{3-7}$ heterocycloalkyl, aryl, or heteroaryl any of which groups is optionally substituted by one or more substituents independently selected from halogen, cyano, $C_{1-6}$ alkyl, trifluoromethyl, ($C_{3-7}$)-heterocycloalkyl, dihalo($C_{3-7}$)heterocycloalkyl, hydroxy, oxo, $C_{1-6}$ alkoxy, difluoromethoxy, trifluoromethoxy, trifluoroethoxy, $C_{1-6}$ alkylsulfonyl, $C_{1-6}$ alkylamino and di($C_{1-6}$)alkylamino;

$A^1$ represents hydrogen, methyl, ethyl, isopropyl, isobutyl, trifluoromethyl, trifluoroethyl, —$CH_2OR^a$ or —$CH_2CH_2OR^a$;

$A^2$ represents hydrogen or $C_{1-6}$ alkyl;

$R^4$ represents hydrogen or $C_{1-6}$ alkyl;

$R^a$ represents hydrogen or $C_{1-6}$ alkyl; and $R^{13}$ represents $C_{1-6}$ alkyl.

2. A compound as claimed in claim 1 wherein Q represents a group of formula (Qa-1), (Qa-2) or (Qa-3):

(Qa-1)

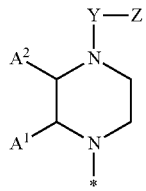

(Qa-2)

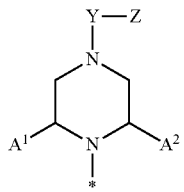

-continued (Qa-3)

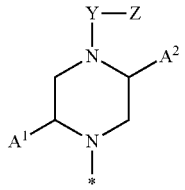

in which the asterisk (*) represents the point of attachment to the remainder of the molecule.

3. A compound as claimed in claim 1 represented by formula (IIA), or a pharmaceutically acceptable salt or solvate thereof:

(IIA)

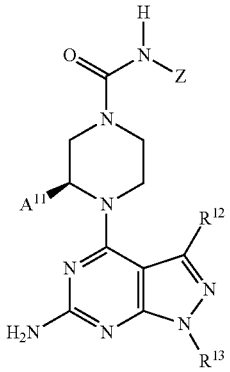

wherein $A^{11}$ represents hydrogen, methyl, ethyl, isopropyl, isobutyl, trifluoromethyl, —$CH_2CF_3$, hydroxymethyl, or hydroxyethyl; and $R^{12}$ represents hydrogen, trifluoromethyl or $C_{1-6}$ alkyl.

4. A compound as claimed in claim 1 represented by formula (IIB), or a pharmaceutically acceptable salt or solvate thereof:

(IIB)

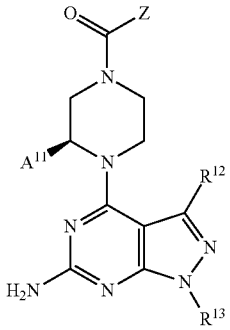

wherein $R^{12}$ represents hydrogen, trifluoromethyl or $C_{1-6}$ alkyl; and $A^{11}$ represents hydrogen, methyl, ethyl, isopropyl, isobutyl, trifluoromethyl, —$CH_2CF_3$, hydroxymethyl, or hydroxyethyl.

5. A compound as claimed in claim 3 wherein $A^{11}$ represents methyl, ethyl, hydroxymethyl or hydroxyethyl.

6. A compound as claimed in claim 1 wherein Z represents $C_{3-7}$ cycloalkyl, $C_{3-7}$ heterocycloalkyl, aryl or heteroaryl, any of which groups is optionally substituted by one, two or three substituents independently selected from halogen, cyano, $C_{1-6}$ alkyl, trifluoromethyl, ($C_{3-7}$)heterocycloalkyl, dihalo($C_{3-7}$)-heterocycloalkyl, hydroxy, oxo, $C_{1-6}$ alkoxy, difluoromethoxy, trifluoromethoxy, trifluoroethoxy, $C_{1-6}$ alkylsulfonyl, $C_{1-6}$ alkylamino and di($C_{1-6}$)alkylamino.

7. A compound as claimed in claim 6 wherein Z represents (methoxy)(methyl)-phenyl, (methyl)(trifluoromethoxy)phenyl, (methoxy)(methyl)pyridinyl, (ethyl)-(methoxy)pyridinyl, (ethoxy)(methyl)pyridinyl or dimethoxypyridinyl.

8. A compound as claimed in claim 1 wherein $R^{12}$ represents hydrogen or methyl.

9. A compound as claimed in claim 1 wherein $R^{13}$ represents methyl.

10. A compound of formula (IA) as claimed in claim 1 which is

[6-Amino-4-{4-[(4-methoxy-2-methylphenyl)carbamyl]piperazin-1-yl}-1H-pyrazolo[3,4-d]pyrimidine;

6-Amino-4-{4-[(4-methoxyphenyl)carbamyl]piperazin-1-yl}-1H-pyrazolo[3,4-d]-pyrimdine;

6-Amino-4-{4-[(4-methoxy-2-methylphenyl)carbamyl]-2-(S)-methylpiperazin-1-yl}-1H-pyrazolo[3,4-d]pyrimidine;

6-Amino-4-{4-[(4-methoxyphenyl)carbamyl]-2-(S)-methylpiperazin-1-yl}-1H-pyrazolo[3,4-d]pyrimidine;

6-Amino-4-{4-[(4-methoxy-2-methylphenyl)carbamyl]-2-(S)-methylpiperazin-1-yl}-1-methylpyrazolo[3,4-d]pyrimidine;]

6-Amino-4-{4-[(4-methoxyphenyl)carbamyl]-2-(S)-methylpiperazin-1-yl}-1-methylpyrazolo[3,4-d]pyrimidine;

6-Amino-4-[4-(indan-5-ylcarbamyl)-2-(S)-methylpiperazin-1-yl]-1-methylpyrazolo[3,4-d]pyrimidine;

6-Amino-4-(4-{[4-(dimethylamino)phenyl]carbamyl}-2-(S)-methylpiperazin-1-yl)-1-methylpyrazolo[3,4-d]pyrimidine;

(3S)-4-(6-Amino-1,3-dimethylpyrazolo[3,4-d]pyrimidin-4-yl)-N-[6-(3,3-difluoroazetidin-1-yl)-2-methylpyridin-3-yl]-3-methylpiperazine-1-carboxamide;

(3S)-4-(6-Amino-1,3-dimethylpyrazolo[3,4-d]pyrimidin-4-yl)-N-(4-methoxy-2-methyl-phenyl)-3-methylpiperazine-1-carboxamide;

(3S)-4-(6-Amino-1,3-dimethylpyrazolo[3,4-d]pyrimidin-4-yl)-N-(6-methoxy-2-methyl-pyridin-3-yl)-3-methylpiperazine-1-carboxamide;

(3R)-4-(6-Amino-1-methylpyrazolo[3,4-d]pyrimidin-4-yl)-N-[6-(3,3-difluoroazetidin-1-yl)-2-methylpyridin-3-yl]-3-(hydroxymethyl)piperazine-1-carboxamide;

(3S)-4-(6-Amino-1-methylpyrazolo[3,4-d]pyrimidin-4-yl)-N-[6-(3,3-difluoroazetidin-1-yl)-2-methylpyridin-3-yl]-3-methylpiperazine-1-carboxamide;

(3S)-4-(6-Amino-1-methylpyrazolo[3,4-d]pyrimidin-4-yl)-N-(6-methoxy-2-methyl-pyridin-3-yl)-3-methylpiperazine-1-carboxamide;

(3R)-4-(6-Amino-1-methylpyrazolo[3,4-d]pyrimidin-4-yl)-N-(4-methoxy-2-methyl-phenyl)-3-methylpiperazine-1-carboxamide;

(3S)-4-[6-Amino-1-methyl-3-(trifluoromethyl)pyrazolo[3,4-d]pyrimidin-4-yl]-N-[6-(3,3-difluoroazetidin-1-yl)-2-methylpyridin-3-yl]-3-methylpiperazine-1-carboxamide;

(3S)-4-[6-Amino-1-methyl-3-(trifluoromethyl)pyrazolo[3,4-d]pyrimidin-4-yl]-N-(6-methoxy-2-methylpyridin-3-yl)-3-methylpiperazine-1-carboxamide;

(3S)-4-[6-Amino-1-methyl-3-(trifluoromethyl)pyrazolo[3,4-d]pyrimidin-4-yl]-N-(4-methoxy-2-methylphenyl)-3-methylpiperazine-1-carboxamide;

(3S)-4-(6-Amino-1-methylpyrazolo[3,4-d]pyrimidin-4-yl)-N-(2, 1,3-benzothiadiazol-4-yl)-3-methylpiperazine-1-carboxamide;

(3S)-4-(6-Amino-1-methylpyrazolo[3,4-d]pyrimidin-4-yl)-N-(1H-indazol-7-yl)-3-methylpiperazine-1-carboxamide;

(3S)-4-(6-Amino-1-methylpyrazolo[3,4-d]pyrimidin-4-yl)-N-(2, 1,3-benzothiadiazol-5-yl)-3-methylpiperazine-1-carboxamide;

(3S)-4-(6-Amino-1-methylpyrazolo[3,4-d]pyrimidin-4-yl)-N-(1H-indol-7-yl)-3-methylpiperazine-1-carboxamide;

(3S)-4-(6-Amino-1-methylpyrazolo[3,4-d]pyrimidin-4-yl)-N-(1H-indol-4-yl)-3-methylpiperazine-1-carboxamide;

(3S)-4-(6-Amino-1-methylpyrazolo[3,4-d]pyrimidin-4-yl)-3-methyl-N-(2-methyl-1H-benzimidazol-4-yl)piperazine-1-carboxamide;

(3S)-4-(6-Amino-1-methylpyrazolo[3,4-d]pyrimidin-4-yl)-3-methyl-N-(1-methylindazol-7-yl)piperazine-1-carboxamide;

(3S)-4-(6-Amino-1-methylpyrazolo[3,4-d]pyrimidin-4-yl)-3-methyl-N-(4-methyl-1H-indazol-7-yl)piperazine-1-carboxamide;

(3S)-4-(6-Amino-1-methylpyrazolo[3,4-d]pyrimidin-4-yl)-N-(6-hydroxy-2-methylpyridin-3-yl)-3-methylpiperazine-1-carboxamide;

(3S)-4-(6-Amino-1-methylpyrazolo[3,4-d]pyrimidin-4-yl)-3-methyl-N-[2-methyl-6-(2,2,2-trifluoroethoxy) pyridin-3-yl]-piperazine-1-carboxamide;

(3S)-4-(6-Amino-1-methylpyrazolo[3,4-d]pyrimidin-4-yl)-N-(1,2-dimethyl-6-oxopyridin-3-yl)-3-methylpiperazine-1-carboxamide;

(3S)-4-(6-Amino-1-methylpyrazolo[3,4-d]pyrimidin-4-yl)-3-methyl-N-[2-methyl-6-(methylamino)pyridin-3-yl]-piperazine-1-carboxamide;

(3S)-4-(6-Amino-1-methylpyrazolo-[3,4-d]pyrimidin-4-yl)-N-[2-(3,3-difluoroazetidin-1-yl)-4-methyl-pyrimidin-5-yl]-3-methylpiperazine-1-carboxamide;

(3S)-4-(6-Amino-1-methylpyrazolo-[3,4-d]pyrimidin-4-yl)-N-[4-(difluoro-methoxy)-2-methylphenyl]-3-methyl-piperazine-1-carboxamide;

(3S)-4-(6-Amino-1-methylpyrazolo-[3,4-d]pyrimidin-4-yl)-N-[2-(dimethyl-amino)-4-methylpyrimidin-5-yl]-3-methylpiperazine-1-carboxamide;

(3S)-4-(6-Amino-1-methylpyrazolo-[3,4-d]pyrimidin-4-yl)-N-[6-(azetidin-1-yl)-2-methylpyridin-3-yl]-3-methyl-piperazine-1-carboxamide;

(3S)-4-(6-Amino-1-methylpyrazolo-[3,4-d]pyrimidin-4-yl)-N-[6-(3,3-difluoroazetidin-1-yl)-4-methylpyridin-3-yl]-3-methylpiperazine-1-carboxamide;

(3S)-4-(6-Amino-1-methylpyrazolo-[3,4-d]pyrimidin-4-yl)-N-[6-(dimethyl-amino)-2-methylpyridin-3-yl]-3-methylpiperazine-1-carboxamide;

(3S)-4-(6-Amino-1-methylpyrazolo-[3,4-d]pyrimidin-4-yl)-N-[6-(dimethyl-amino)-methylpyridin-3-yl]-3-methylpiperazine-1-carboxamide;

(3S)-4-(6-Amino-1,3-dimethyl-pyrazolo[3,4-d]pyrimidin-4-yl)-N-[6-(azetidin-1-yl)-2-methylpyridin-3-yl]-3-methylpiperazine-1-carboxamide;

(3S)-4-(6-Amino-1,3-dimethyl-pyrazolo[3,4-d]pyrimidin-4-yl)-N-[6-(dimethylamino)-4-methylpyridin-3-yl]-3-methylpiperazine-1-carboxamide;

(3S)-4-(6-Amino-1,3-dimethyl-pyrazolo[3,4-d]pyrimidin-4-yl)-N-[6-(dimethylamino)-2-methylpyridin-3-yl]-3-methylpiperazine-1-carboxamide;

(3S)-4-(6-Amino-1,3-dimethylpyrazolo[3,4-d]pyrimidin-4-yl)-N-(4-methoxyphenyl)-3-methylpiperazine-1-carboxamide;

[(3S)-4-(6-Amino-1-methylpyrazolo-[3,4-d]pyrimidin-4-yl)-3-methyl-piperazin-1-yl](2,3-dihydrobenzo-furan-2-yl)methanone;

1-[(3S)-4-(6-Amino-1-methylpyrazolo-[3,4-d]pyrimidin-4-yl)-3-methyl-piperazin-1-yl]-2-phenylethane-1,2-dione;

[(3S)-4-(6-Amino-1-methylpyrazolo-[3,4-d]pyrimidin-4-yl)-3-methyl-piperazin-1-yl](5-methoxybenzofuran-2-yl)methanone;

[(3S)-N-(4-Methoxy-2-methylphenyl)-3-methyl-4-[1-methyl-6-(methylsulfanyl)-pyrazolo[3,4-d]pyrimidin-4-yl]piperazine-1-carboxamide;

(3S)-N-(Indan-5-yl)-3-methyl-4-[1-methyl-6-(methylsulfonyl)pyrazolo[3,4-d]pyrimidin-4-yl]piperazine-1-carboxamide;

(3S)-N-(Indan-5-yl)-4-(6-methoxy-1-methylpyrazolo[3,4-d]pyrimidin-4-yl)-3-methyl-piperazine-1-carboxamide;

(3S)-4-(6-Cyano-1-methylpyrazolo[3,4-d]pyrimidin-4-yl)-N-(indan-5-yl)-3-methyl-piperazine-1-carboxamide;

(3S)-4-[6-(2-Hydroxyethylamino)-1-methylpyrazolo[3,4-d]pyrimidin-4-yl]-N-(4-methoxy-2-methylphenyl)-3-methylpiperazine-1-carboxamide;]

(3S)-4-(6-Amino-1-methylpyrazolo[3,4-d]pyrimidin-4-yl)-3-methyl-N-[2-methyl-4-(trifluoromethoxy)phenyl]piperazine-1-carboxamide;

(3S)-4-(6-Amino-1-methyl-1H-pyrazolo[3,4-d]-pyrimidin-4-yl)-N-[2-fluoro-4-(trifluoromethoxy)-phenyl]-3-methylpiperazine-1-carboxamide;

(3S)-4-(6-Amino-1-methyl-1H-pyrazolo[3,4-d]-pyrimidin-4-yl)-N-[2-chloro-4-(trifluoromethoxy)-phenyl]-3-methylpiperazine-1-carboxamide;

(3S)-4-(6-Amino-1-methyl-1H-pyrazolo[3,4-d]-pyrimidin-4-yl)-N-[3-methoxy-5-(trifluoromethyl)-phenyl]-3-methylpiperazine-1-carboxamide;

(3S)-4-(6-Amino-1-methyl-1H-pyrazolo[3,4-d]-pyrimidin-4-yl)-N-(1-ethyl-1H-indazol-3-yl)-3-methyl-piperazine-1-carboxamide;

(3S)-4-(6-Amino-1-methyl-1H-pyrazolo[3,4-d]-pyrimidin-4-yl)-N-[6-(difluoromethoxy)-2-methyl-pyridin-3-yl]-3-methylpiperazine-1-carboxamide;

(3S)-4-(6-Amino-1-methyl-1H-pyrazolo[3,4-d]-pyrimidin-4-yl)-N-(6-ethoxy-5-fluoropyridin-3-yl)-3-methylpiperazine-1-carboxamide;

(3S)-4-(6-Amino-1-methyl-1H-pyrazolo[3,4-d]-pyrimidin-4-yl)-N-(2-chloro-4-fluoro-5-methylphenyl)-3-methylpiperazine-1-carboxamide;

(3S)-4-(6-Amino-1-methyl-1H-pyrazolo[3,4-d]-pyrimidin-4-yl)-N-(5-fluoro-6-methoxypyridin-3-yl)-3-methylpiperazine-1-carboxamide;

(3S)-4-(6-Amino-1-methyl-1H-pyrazolo[3,4-d]-pyrimidin-4-yl)-N-(6-ethoxy-2-methylpyridin-3-yl)-3-methylpiperazine-1-carboxamide;

(3S)-4-(6-Amino-1-methyl-1H-pyrazolo[3,4-d]-pyrimidin-4-yl)-3-methyl-N-[1-methyl-5-(trifluoro-methyl)-1H-indazol-3-yl]piperazine-1-carboxamide;

(3S)-4-(6-Amino-1-methyl-1H-pyrazolo[3,4-d]-pyrimidin-4-yl)-N-(6-fluoro-1-methyl-1H-indazol-3-yl)-3-methylpiperazine-1-carboxamide;

(3S)-4-(6-Amino-1-methyl-1H-pyrazolo[3,4-d]-pyrimidin-4-yl)-N-(5-fluoro-1-methyl-1H-indazol-3-yl)-3-methylpiperazine-1-carboxamide;

(3S)-4-(6-Amino-1-methyl-1H-pyrazolo[3,4-d]-pyrimidin-4-yl)-N-(imidazo[1,2-a]pyridin-8-yl)-3-methylpiperazine-1-carboxamide;

(3S)-4-(6-Amino-1-methyl-1H-pyrazolo[3,4-d]-pyrimidin-4-yl)-3-methyl-N-(5-methyl-1,2-oxazol-3-yl)-piperazine-1-carboxamide;

(3S)-4-(6-Amino-1-methyl-1H-pyrazolo[3,4-d]-pyrimidin-4-yl)-N-(1,2-benzoxazol-3-yl)-3-methyl-piperazine-1-carboxamide;

(3S)-4-(6-Amino-1-methyl-1H-pyrazolo[3,4-d]-pyrimidin-4-yl)-3-methyl-N-(1-methyl-1H-indazol-3-yl)piperazine-1-carboxamide;

(3S)-4-(6-Amino-1-methyl-1H-pyrazolo[3,4-d]-pyrimidin-4-yl)-N-(6-cyano-2-methylpyridin-3-yl)-3-methylpiperazine-1-carboxamide;

(3S)-4-(6-Amino-1-methyl-1H-pyrazolo[3,4-d]-pyrimidin-4-yl)-3-methyl-N-[2-methyl-4-(methyl-sulfonyl) phenyl]piperazine-1-carboxamide;

(3S)-4-(6-Amino-1-methyl-1H-pyrazolo[3,4-d]-pyrimidin-4-yl)-N-[6-(difluoromethoxy)-4-methyl-pyridin-3-yl]-3-methylpiperazine-1-carboxamide;

(3S)-4-(6-Amino-1-methyl-1H-pyrazolo[3,4-d]-pyrimidin-4-yl)-N-(6-methoxy-5-methylpyridin-3-yl)-3-methylpiperazine-1-carboxamide;

(3S)-4-(6-Amino-1-methyl-1H-pyrazolo[3,4-d]-pyrimidin-4-yl)-N-(6-methoxy-4-methylpyridin-3-yl)-3-methylpiperazine-1-carboxamide;

(3S)-4-(6-Amino-1-methyl-1H-pyrazolo[3,4-d]-pyrimidin-4-yl)-N-(5-methoxy-2-methylphenyl)-3-methylpiperazine-1-carboxamide;

(3S)-4-(6-Amino-1-methyl-1H-pyrazolo[3,4-d]-pyrimidin-4-yl)-N-(3-chloro-4-methylphenyl)-3-methyl-piperazine-1-carboxamide;

(3S)-4-(6-Amino-1-methyl-1H-pyrazolo[3,4-d]-pyrimidin-4-yl)-N-(2,5-dichlorophenyl)-3-methyl-piperazine-1-carboxamide;

(3S)-4-(6-Amino-1-methyl-1H-pyrazolo[3,4-d]-pyrimidin-4-yl)-N-(4-cyano-2-methylphenyl)-3-methyl-piperazine-1-carboxamide;

(3S)-4-(6-Amino-1-methylpyrazolo[3,4-d]pyrimidin-4-yl)-3-ethyl-N-(6-methoxy-2-methylpyridin-3-yl)piperazine-1-carboxamide;

(3S)-4-(6-Amino-1-methylpyrazolo[3,4-d]pyrimidin-4-yl)-N-(6-ethoxy-2-methylpyridin-3-yl)-3-ethylpiperazine-1-carboxamide;

(3S)-4-(6-Amino-1-methylpyrazolo[3,4-d]pyrimidin-4-yl)-N-(2,6-dimethoxypyridin-3-yl)-3-ethylpiperazine-1-carboxamide;

(3S)-4-(6-Amino-1-methylpyrazolo[3,4-d]pyrimidin-4-yl)-3-ethyl-N-(4-methoxy-2-methylphenyl)piperazine-1-carboxamide;

(3S)-4-(6-Amino-1-methylpyrazolo[3,4-d]pyrimidin-4-yl)-N-[6-(3,3-difluoroazetidin-1-yl)-2-methylpyridin-3-yl]-3-ethylpiperazine-1-carboxamide;

(3S)-4-(6-Amino-1-methylpyrazolo[3,4-d]pyrimidin-4-yl)-3-ethyl-N-[2-methyl-4-(trifluoromethoxy)phenyl] piperazine-1-carboxamide;

(3S)-4-(6-Amino-1-methylpyrazolo[3,4-d]pyrimidin-4-yl)-3-ethyl-N-(4-methoxy-3-methylphenyl)piperazine-1-carboxamide;

(3S)-4-(6-Amino-1-methyl-1H-pyrazolo[3,4-d]-pyrimidin-4-yl)-N-(1,2-benzoxazol-3-yl)-3-ethyl-piperazine-1-carboxamide;

(3S)-4-(6-Amino-1-methyl-1H-pyrazolo[3,4-d]-pyrimidin-4-yl)-3-ethyl-N-(1-methyl-1H-indazol-3-yl)-piperazine-1-carboxamide;

(3S)-4-(6-Amino-1-methyl-1H-pyrazolo[3,4-d]-pyrimidin-4-yl)-N-[6-(difluoromethoxy)-4-methyl-pyridin-3-yl]-3-ethylpiperazine-1-carboxamide;

(3S)-4-(6-Amino-1-methyl-1H-pyrazolo[3,4-d]-pyrimidin-4-yl)-3-ethyl-N-(6-methoxy-5-methyl-pyridin-3-yl)piperazine-1-carboxamide;

(3S)-4-(6-Amino-1-methyl-1H-pyrazolo[3,4-d]-pyrimidin-4-yl)-3-ethyl-N-[2-methyl-4-(methyl-sulfonyl) phenyl]piperazine-1-carboxamide;

(3S)-4-(6-Amino-1-methyl-1H-pyrazolo[3,4-d]-pyrimidin-4-yl)-3-ethyl-N-(6-methoxy-4-methyl-pyridin-3-yl)piperazine-1-carboxamide;

(3S)-4-(6-Amino-1-methyl-1H-pyrazolo[3,4-d]-pyrimidin-4-yl)-3-ethyl-N-[1-methyl-5-(trifluoro-methyl)-1H-indazol-3-yl]piperazine-1-carboxamide;

(3S)-4-(6-Amino-1-methyl-1H-pyrazolo[3,4-d]-pyrimidin-4-yl)-3-ethyl-N-(6-fluoro-1-methyl-1H-indazol-3-yl)piperazine-1-carboxamide;

(3S)-4-(6-Amino-1-methyl-1H-pyrazolo[3,4-d]-pyrimidin-4-yl)-3-ethyl-N-(5-fluoro-1-methyl-1H-indazol-3-yl)piperazine-1-carboxamide;

(3S)-4-(6-Amino-1-methyl-1H-pyrazolo[3,4-d]-pyrimidin-4-yl)-N-[6-(difluoromethoxy)-2-methyl-pyridin-3-yl]-3-ethylpiperazine-1-carboxamide;

(3S)-4-(6-Amino-1-methyl-1H-pyrazolo[3,4-d]-pyrimidin-4-yl)-3-ethyl-N-(imidazo[1,2-a]pyridin-8-yl)piperazine-1-carboxamide;

(3S)-4-(6-Amino-1-methyl-1H-pyrazolo[3,4-d]-pyrimidin-4-yl)-N-(6-ethoxy-5-fluoropyridin-3-yl)-3-ethylpiperazine-1-carboxamide;

(3S)-4-(6-Amino-1-methyl-1H-pyrazolo[3,4-d]-pyrimidin-4-yl)-N-(2-chloro-4-fluoro-5-methyl-phenyl)-3-ethylpiperazine-1-carboxamide;

(3S)-4-(6-Amino-1-methyl-1H-pyrazolo[3,4-d]-pyrimidin-4-yl)-3-ethyl-N-(5-fluoro-6-methoxy-pyridin-3-yl) piperazine-1-carboxamide;

(3S)-4-(6-Amino-1-methyl-1H-pyrazolo[3,4-d]-pyrimidin-4-yl)-N-(6-cyano-2-methylpyridin-3-yl)-3-ethylpiperazine-1-carboxamide;

(3S)-4-(6-Amino-1-methyl-1H-pyrazolo[3,4-d]-pyrimidin-4-yl)-N-(4-cyano-2-methylphenyl)-3-ethyl-piperazine-1-carboxamide;

(3S)-4-(6-Amino-1-methyl-1H-pyrazolo[3,4-d]-pyrimidin-4-yl)-N-[4-(difluoromethoxy)-2-methyl-phenyl]-3-ethylpiperazine-1-carboxamide;

(3S)-4-(6-Amino-1-methyl-1H-pyrazolo[3,4-d]-pyrimidin-4-yl)-N-[5-(dimethylamino)-3-methyl-pyrazin-2-yl]-3-ethylpiperazine-1-carboxamide;

(3S)-4-(6-Amino-1-methyl-1H-pyrazolo[3,4-d]pyrimidin-4-yl)-3-methyl-N-(1-methyl-1H-indazol-4-yl)-piperazine-1-carboxamide;

(3S)-4-(6-Amino-1-methyl-1H-pyrazolo[3,4-d]pyrimidin-4-yl)-N-(2-methoxy-6-methylpyridin-3-yl)-3-methylpiperazine-1-carboxamide;

(3S)-4-(6-Amino-1-methyl-1H-pyrazolo[3,4-d]pyrimidin-4-yl)-3-methyl-N-(1-methyl-1H-indol-4-yl)piperazine-1-carboxamide;

(3S)-4-(6-Amino-1-methyl-1H-pyrazolo[3,4-d]pyrimidin-4-yl)-3-methyl-N-(1-methyl-1H-benzotriazol-4-yl) piperazine-1-carboxamide;

(3S)-4-(6-Amino-1-methyl-1H-pyrazolo[3,4-d]pyrimidin-4-yl)-N-(imidazo[1,2-a]pyridin-5-yl)-3-methylpiperazine-1-carboxamide;

(3S)-4-(6-Amino-1-methyl-1H-pyrazolo[3,4-d]pyrimidin-4-yl)-N-(imidazo[1,2-a]pyridin-3-yl)-3-methylpiperazine-1-carboxamide;

(3S)-4-(6-Amino-1-methyl-1H-pyrazolo[3,4-d]-pyrimidin-4-yl)-3-methyl-N-(1-methyl-1H-pyrazolo-[4,3-c] pyridin-4-yl)piperazine-1-carboxamide;

(3S)-4-(6-Amino-1-methyl-1H-pyrazolo[3,4-d]-pyrimidin-4-yl)-N-(3-chloro-5-methoxypyridin-2-yl)-3-methylpiperazine-1-carboxamide;

(3S)-4-(6-Amino-1-methyl-1H-pyrazolo[3,4-d]-pyrimidin-4-yl)-N-(2-chloro-4-methoxyphenyl)-3-methylpiperazine-1-carboxamide;

(3S)-4-(6-Amino-1-methyl-1H-pyrazolo[3,4-d]-pyrimidin-4-yl)-N-[6-methoxy-2-(trifluoromethyl)-pyridin-3-yl]-3-methylpiperazine-1-carboxamide;

(3S)-4-(6-Amino-1-methyl-1H-pyrazolo[3,4-d]-pyrimidin-4-yl)-N-(6-fluoro-1-methyl-1H-indazol-4-yl)-3-methylpiperazine-1-carboxamide;

(3S)-4-(6-Amino-1-methyl-1H-pyrazolo[3,4-d]-pyrimidin-4-yl)-N-(2-ethyl-6-methoxypyridin-3-yl)-3-methylpiperazine-1-carboxamide;

(3S)-4-(6-Amino-1-methyl-1H-pyrazolo[3,4-d]-pyrimidin-4-yl)-N-[5-(dimethylamino)-3-methyl-pyrazin-2-yl]-3-methylpiperazine-1-carboxamide;

(3S)-4-(6-Amino-1-methyl-1H-pyrazolo[3,4-d]-pyrimidin-4-yl)-3-ethyl-N-(1-methyl-1H-pyrazolo[4,3-c] pyridin-4-yl)piperazine-1-carboxamide;

(3S)-4-(6-Amino-1-methyl-1H-pyrazolo[3,4-d]-pyrimidin-4-yl)-N-(2-chloro-4-methoxyphenyl)-3-ethylpiperazine-1-carboxamide;

(3S)-4-(6-Amino-1-methyl-1H-pyrazolo[3,4-d]-pyrimidin-4-yl)-3-ethyl-N-(6-fluoro-1-methyl-1H-indazol-4-yl)piperazine-1-carboxamide;

(3S)-4-(6-Amino-1-methyl-1H-pyrazolo[3,4-d]-pyrimidin-4-yl)-3-ethyl-N-[6-methoxy-2-(trifluoro-methyl) pyridin-3-yl]piperazine-1-carboxamide;

(3S)-4-(6-Amino-1-methyl-1H-pyrazolo[3,4-d]-pyrimidin-4-yl)-3-ethyl-N-(2-ethyl-6-methoxypyridin-3-yl) piperazine-1-carboxamide;

(3S)-4-(6-Amino-1,3-dimethyl-1H-pyrazolo[3,4-d]-pyrimidin-4-yl)-N-[2-(dimethylamino)-4-methyl-pyrimidin-5-yl]-3-methylpiperazine-1-carboxamide;

4-(6-Amino-1-methylpyrazolo[3,4-d]pyrimidin-4-yl)-3-(2-hydroxyethyl)-N-[2-methyl-4-(trifluoromethoxy) phenyl]piperazine-1-carboxamide;

(3R)-4-(6-Amino-1-methyl-1H-pyrazolo[3,4-d]pyrimidin-4-yl)-3-(hydroxymethyl)-N-[2-methyl-4-(trifluoromethoxy)phenyl]piperazine-1-carboxamide;

(3S)-4-(6-Amino-1-methyl-1H-pyrazolo[3,4-d]-pyrimidin-4-yl)-N-(6-methoxy-2-methylpyridin-3-yl)-3-(propan-2-yl)piperazine-1-carboxamide;

(3S)-4-(6-Amino-1-methyl-1H-pyrazolo[3,4-d]-pyrimidin-4-yl)-N-(6-methoxy-2-methylpyridin-3-yl)-3-(2-methylpropyl)piperazine-1-carboxamide;

4-(6-Amino-1-methyl-1H-pyrazolo[3,4-d]-pyrimidin-4-yl)-N-(6-methoxy-2-methylpyridin-3-yl)-3-(2,2,2-trifluoroethyl)piperazine-1-carboxamide;

4-(6-Amino-1-methyl-1H-pyrazolo[3,4-d]-pyrimidin-4-yl)-N-(imidazo[1,2-a]pyridin-8-yl)-3-(2,2,2-trifluoroethyl)piperazine-1-carboxamide;

(3S,5S)-4-(6-Amino-1-methyl-1H-pyrazolo[3,4-d]-pyrimidin-4-yl)-N-(1-ethyl-1H-indazol-3-yl)-3,5-dimethylpiperazine-1-carboxamide;

(3S,5S)-4-(6-Amino-1-methyl-1H-pyrazolo[3,4-d]-pyrimidin-4-yl)-3,5-dimethyl-N-(1-methyl-1H-indazol-3-yl)piperazine-1-carboxamide;

(3S,5S)-4-(6-Amino-1-methyl-1H-pyrazolo[3,4-d]-pyrimidin-4-yl)-N-[5-(dimethylamino)-3-methyl-pyrazin-2-yl]-3,5-dimethylpiperazine-1-carboxamide;

(3S,5S)-4-(6-Amino-1-methyl-1H-pyrazolo[3,4-d]-pyrimidin-4-yl)-N-(imidazo[1,2-a]pyridin-8-yl)-3, 5-dimethylpiperazine-1-carboxamide;

(3S,5S)-4-(6-Amino-1-methyl-1H-pyrazolo[3,4-d]-pyrimidin-4-yl)-3,5-dimethyl-N-[2-methyl-4-(trifluoromethoxy)phenyl]piperazine-1-carboxamide;

(3S,5S)-4-(6-Amino-1-methyl-1H-pyrazolo[3,4-d]-pyrimidin-4-yl)-N-(6-methoxy-2-methylpyridin-3-yl)-3, 5-dimethylpiperazine-1-carboxamide;

4-(6-Amino-1-methyl-1H-pyrazolo[3,4-d]-pyrimidin-4-yl)-N-(6-methoxy-2-methylpyridin-3-yl)-3-(trifluoromethyl)piperazine-1-carboxamide;

4-(6-Amino-1-methyl-1H-pyrazolo[3,4-d]-pyrimidin-4-yl)-N-(4-methoxy-2-methylphenyl)-3-(trifluoromethyl)piperazine-1-carboxamide;

(3S)-4-(6-Amino-1,3-dimethyl-1H-pyrazolo[3,4-d]-pyrimidin-4-yl)-N-(6-fluoro-1-methyl-1H-indazol-3-yl)-3-methylpiperazine-1-carboxamide;

(3S)-4-(6-Amino-1,3-dimethyl-1H-pyrazolo[3,4-d]-pyrimidin-4-yl)-N-(5-fluoro-1-methyl-1H-indazol-3-yl)-3-methylpiperazine-1-carboxamide;

(3S)-4-(6-Amino-1,3-dimethyl-1H-pyrazolo[3,4-d]-pyrimidin-4-yl)-N-[6-(difluoromethoxy)-2-methyl-pyridin-3-yl]-3-methylpiperazine-1-carboxamide;

(3S)-4-(6-Amino-1,3-dimethyl-1H-pyrazolo[3,4-d]-pyrimidin-4-yl)-N-[5-(dimethylamino)-3-methyl-pyrazin-2-yl]-3-methylpiperazine-1-carboxamide; *or*

(3S)-4-(6-Amino-1,3-dimethyl-1H-pyrazolo[3,4-d]-pyrimidin-4-yl)-N-[4-(difluoromethoxy)-2-methyl-phenyl]-3-methylpiperazine-1-carboxamide;

[(3S)-4-[6-Amino-3-(4-fluorophenyl)-1-methylpyrazolo [3,4-d]pyrimidin-4-yl]-N-(4-methoxy-2-methylphenyl)-3-methylpiperazine-1-carboxamide; or (3S)-4-[6-Amino-1-methyl-3-(pyridin-3-yl)pyrazolo[3,4-d]pyrimidin-4-yl]-N-(4-methoxy-2-methylphenyl)-3-methylpiperazine-1-carboxamide;]

or a pharmaceutically acceptable salt of one of the foregoing.

11. A pharmaceutical composition comprising a compound of formula (IA) as defined in claim 1, or a pharmaceutically acceptable salt or solvate thereof, and a pharmaceutically acceptable carrier.

12. A method for the treatment of organ or cell transplant rejection, which comprises administering to a patient in need of such treatment an effective amount of a compound of formula (IA) as defined in claim 1, or a pharmaceutically acceptable salt or solvate thereof.

* * * * *